(12) United States Patent
Larsen et al.

(10) Patent No.: US 6,528,486 B1
(45) Date of Patent: Mar. 4, 2003

(54) PEPTIDE AGONISTS OF GLP-1 ACTIVITY

(75) Inventors: Bjarne Due Larsen, Brønshøj (DK); Jens Damsgaard Mikkelsen, Lyngby (DK); Søren Neve, Lyngby (DK)

(73) Assignee: Zealand Pharma A/S, Glostrup (DK)

( * ) Notice: Subject to any disclaimer, the term of this patent is extended or adjusted under 35 U.S.C. 154(b) by 0 days.

(21) Appl. No.: 09/614,847

(22) Filed: Jul. 12, 2000

Related U.S. Application Data

(60) Provisional application No. 60/143,591, filed on Jul. 12, 1999.

(51) Int. Cl.[7] .............................................. A61K 38/00
(52) U.S. Cl. .............................. 514/12; 514/2; 530/300; 530/303
(58) Field of Search ....................... 514/12, 2; 530/300, 530/303

(56) References Cited

U.S. PATENT DOCUMENTS

| | | | |
|---|---|---|---|
| 5,424,286 A | 6/1995 | Eng ............................... | 514/2 |
| 5,545,618 A | 8/1996 | Buckley et al. ................ | 514/12 |

FOREIGN PATENT DOCUMENTS

| | | | | |
|---|---|---|---|---|
| WO | WO 98/05351 | 2/1998 | | |
| WO | WO 98/08871 | 3/1998 | | |
| WO | WO 98/11126 | * 3/1998 | ........... | C07K/1/107 |
| WO | WO 98/11126 A | 3/1998 | | |
| WO | WO 98/22577 A | 5/1998 | | |
| WO | WO 98/30231 A | 7/1998 | | |
| WO | WO 99/07404 | 2/1999 | | |
| WO | WO 99/25727 | 5/1999 | | |
| WO | WO 99/25728 | 5/1999 | | |
| WO | WO 99/43707 | 9/1999 | | |
| WO | WO 99/43708 | 9/1999 | | |
| WO | WO 99/46283 | 9/1999 | | |

OTHER PUBLICATIONS

J. Eng et al. Isolation and characterization of Exendin–4, an Exendin–3 analogue, from Heloderma suspectum venom. 1992. J. Biol. Chem., 267(11): 7402–05.*
C. Orskov, Diabetologia, 701 (1992).
M. Nauck et al., Horm. Metab. Res., 411 (1997).
Jean–Pierre Raufman, Reg. Peptides 61: 1–18 (1996).
Janet A. Meurer, et al. "Properties of Native and In Vitro Glycosylated Forms Of The Glucagon–Like Peptide–1 Receptor Antagonist Exendin (9–39)", Metabolism, vol. 48, No. 6 (Jun.), 1999, pp 716–724.
M.M. Byrne et al., European Journal of Clinical Investigation, 72 (1998).
C.F. Deacon et al., Diabetologia, 271 (1998).
C. Deacon et al., Diabetes, 764 (1998).
U. Ritzel et al., Journal of Endocrinology, 93 (1998).
R. Pederson et al., Diabetes, 1253 (1998).
R. Goke et al., European Journal of Neuroscience, 2294 (1995).
R. Goke et al., The Journal of Biological Chemistry, 19650 (1993).
M. Pohl et al., The Journal of Biological Chemistry, 9778 (1998).
N.H. Greig et al., Diabetologia, 45 (1999).
Y. Chen et al., The Journal of Biological Chemistry, 4108 (1997).
J.J. Holst, Annu. Rev. Physiol., 257 (1997).
D. A. D'Alessio et al., J. Clin. Invest. (USA) 93 (5):2263–6 (1994).

* cited by examiner

*Primary Examiner*—Lorraine Spector
*Assistant Examiner*—Dong Jiang
(74) *Attorney, Agent, or Firm*—Robert L. Buchanan; Edwards & Angell, LLP

(57) ABSTRACT

The present invention relates to novel peptide conjugates which have increased stability and are useful in the treatment of excess levels of blood glucose.

2 Claims, 8 Drawing Sheets

SEQUENCE LISTING

<160> NUMBER OF SEQ ID NOS: 153

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 1

Lys Lys Lys Lys
 1

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 2

Lys Lys Lys Lys Lys
 1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 3

Xaa Lys Lys Lys Lys
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 4

Lys Xaa Lys Lys Lys
 1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 5

Lys Lys Xaa Lys Lys
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 6

Lys Lys Lys Xaa Lys
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 7

Lys Lys Lys Lys Xaa
 1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 8

Lys Lys Lys Lys Lys Lys
 1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 9

Xaa Lys Lys Lys Lys Lys
 1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence

```
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 10

Lys Xaa Lys Lys Lys Lys
 1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 11

Lys Lys Xaa Lys Lys Lys
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 12

Lys Lys Lys Xaa Lys Lys
 1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 13

Lys Lys Lys Lys Xaa Lys
 1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 14

Lys Lys Lys Lys Lys Xaa
 1               5

<210> SEQ ID NO 15
```

```
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 15

Xaa Xaa Lys Lys Lys Lys
 1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 16

Xaa Lys Xaa Lys Lys Lys
 1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 17

Xaa Lys Lys Xaa Lys Lys
 1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 18

Xaa Lys Lys Lys Xaa Lys
 1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 19
```

Xaa Lys Lys Lys Lys Xaa
 1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 20

Lys Xaa Xaa Lys Lys Lys
 1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 21

Lys Xaa Lys Xaa Lys Lys
 1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 22

Lys Xaa Lys Lys Xaa Lys
 1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 23

Lys Xaa Lys Lys Lys Xaa
 1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: synthetic peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 24

Lys Lys Xaa Xaa Lys Lys
 1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 25

Lys Lys Xaa Lys Xaa Lys
 1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 26

Lys Lys Xaa Lys Lys Xaa
 1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 27

Lys Lys Lys Xaa Xaa Lys
 1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 28

Lys Lys Lys Xaa Lys Xaa
 1               5

```
<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 29

Lys Lys Lys Lys Xaa Xaa
 1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 30

Lys Lys Lys Lys Lys Lys Lys
 1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 31

Xaa Lys Lys Lys Lys Lys Lys
 1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 32

Lys Xaa Lys Lys Lys Lys Lys
 1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 33

Lys Lys Xaa Lys Lys Lys Lys
```

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 34

Lys Lys Lys Xaa Lys Lys Lys
  1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 35

Lys Lys Lys Lys Xaa Lys Lys
  1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 36

Lys Lys Lys Lys Lys Xaa Lys
  1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 37

Lys Lys Lys Lys Lys Lys Xaa
  1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the

```
      sequence may be Ala, Leu, Ser, Thr, Tyr, Asn, Gln, Asp,
      Glu, Arg, His, Met, Orn, Dbu or Dpr

<400> SEQUENCE: 38

Xaa Xaa Lys Lys Lys Lys Lys
 1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 39

Xaa Lys Xaa Lys Lys Lys Lys
 1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 40

Xaa Lys Lys Xaa Lys Lys Lys
 1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 41

Xaa Lys Lys Lys Xaa Lys Lys
 1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 42

Xaa Lys Lys Lys Lys Xaa Lys
 1               5

<210> SEQ ID NO 43
<211> LENGTH: 7
```

```
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 43

Lys Xaa Xaa Lys Lys Lys Lys
 1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 44

Lys Xaa Lys Xaa Lys Lys Lys
 1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 45

Lys Xaa Lys Lys Xaa Lys Lys
 1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 46

Lys Xaa Lys Lys Lys Xaa Lys
 1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 47
```

Lys Lys Xaa Xaa Lys Lys Lys
 1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 48

Lys Lys Xaa Lys Xaa Lys Lys
 1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 49

Lys Lys Xaa Lys Lys Xaa Lys
 1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 50

Lys Lys Lys Xaa Xaa Lys Lys
 1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 51

Lys Lys Lys Xaa Lys Xaa Lys
 1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence

```
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 52

Lys Lys Lys Lys Xaa Xaa Lys
 1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 53

Xaa Xaa Xaa Lys Lys Lys Lys
 1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 54

Xaa Xaa Lys Xaa Lys Lys Lys
 1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 55

Xaa Xaa Lys Lys Xaa Lys Lys
 1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 56

Xaa Xaa Lys Lys Lys Xaa Lys
 1               5

<210> SEQ ID NO 57
```

```
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 57

Xaa Lys Xaa Xaa Lys Lys Lys
 1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 58

Xaa Lys Xaa Lys Xaa Lys Lys
 1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 59

Xaa Lys Xaa Lys Lys Xaa Lys
 1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 60

Xaa Lys Lys Xaa Xaa Lys Lys
 1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 61
```

Xaa Lys Lys Xaa Lys Xaa Lys
 1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 62

Xaa Lys Lys Lys Xaa Lys Xaa
 1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 63

Xaa Lys Lys Xaa Lys Lys Xaa
 1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 64

Xaa Lys Xaa Lys Lys Lys Xaa
 1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 65

Xaa Lys Lys Lys Xaa Xaa Lys
 1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: synthetic -continued peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 66

Lys Xaa Lys Lys Lys Xaa Xaa
  1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 67

Xaa Lys Lys Lys Lys Xaa Xaa
  1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 68

Xaa Lys Lys Lys Xaa Lys Xaa
  1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 69

Xaa Lys Lys Lys Xaa Xaa Lys
  1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 70

Lys Lys Lys Lys Xaa Xaa Xaa
  1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 71

Lys Lys Lys Xaa Xaa Xaa Lys
  1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 72

Lys Lys Lys Xaa Lys Xaa Xaa
  1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 73

Lys Lys Xaa Lys Lys Xaa Xaa
  1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 74

Lys Lys Xaa Xaa Lys Xaa Lys
  1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

```
<400> SEQUENCE: 75

Lys Lys Xaa Xaa Xaa Lys Lys
 1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 76

Lys Lys Xaa Lys Lys Xaa Xaa
 1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 77

Lys Xaa Lys Lys Xaa Xaa Lys
 1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 78

Lys Xaa Lys Xaa Lys Xaa Lys
 1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 79

Lys Xaa Lys Xaa Xaa Lys Lys
 1               5

<210> SEQ ID NO 80
<211> LENGTH: 7
<212> TYPE: PRT
<213> ORGANISM: Artificial Sequence
<220> FEATURE:
```

```
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 80

Lys Xaa Xaa Lys Lys Xaa Lys
 1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 81

Lys Xaa Xaa Lys Xaa Lys Lys
 1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence
<223> OTHER INFORMATION: Xaa at various positions throughout the
      sequence may be Ala, Leu, Ser, Thr, Tyr, Asn, Gln, Asp,
      Glu, Arg, His, Met, Orn, Dbu or Dpr

<400> SEQUENCE: 82

Lys Xaa Xaa Xaa Lys Lys Lys
 1               5

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 83

Lys Glu Lys Glu Lys Glu
 1               5

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 84

Glu Lys Glu Lys Glu Lys
 1               5

<210> SEQ ID NO 85
<211> LENGTH: 6
<212> TYPE: PRT
<213> ORGANISM: Artificial Sequence
<220> FEATURE:
```

```
<223> OTHER INFORMATION: Description of Artificial Sequence: synthetic
      peptide sequence

<400> SEQUENCE: 85

Lys Lys Lys Glu Glu Glu
  1               5

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 86

Glu Glu Glu Lys Lys Lys
  1               5

<210> SEQ ID NO 87
<211> LENGTH: 30
<212> TYPE: PRT
<213> ORGANISM: Artificial Sequence
<220> FEATURE:
<223> OTHER INFORMATION: Description of Artificial Sequence:
      Gly8-GLP-1-(7-36)(Human)-NH2

<400> SEQUENCE: 87

His Gly Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg
             20                  25                  30

<210> SEQ ID NO 88
<211> LENGTH: 36
<212> TYPE: PRT
<213> ORGANISM: Artificial Sequence
<220> FEATURE:
<223> OTHER INFORMATION: Description of Artificial Sequence:
      Gly8-GLP-1-(7-36)(Human)-Lys6-NH2

<400> SEQUENCE: 88

His Gly Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Lys Lys
             20                  25                  30

Lys Lys Lys Lys
         35

<210> SEQ ID NO 89
<211> LENGTH: 38
<212> TYPE: PRT
<213> ORGANISM: Artificial Sequence
<220> FEATURE:
<223> OTHER INFORMATION: Description of Artificial Sequence:
      Gly8Lys37(palmitoyl)-GLP-1-(7-36)(Human)-Lys7-NH2
<221> NAME/KEY: MOD_RES
<222> LOCATION: (31)
<223> OTHER INFORMATION: Lys(palmitoyl)

<400> SEQUENCE: 89

His Gly Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Lys Lys
             20                  25                  30
```

```
Lys Lys Lys Lys Lys Lys
        35

<210> SEQ ID NO 90
<211> LENGTH: 36
<212> TYPE: PRT
<213> ORGANISM: Artificial Sequence
<220> FEATURE:
<223> OTHER INFORMATION: Description of Artificial Sequence:
      Gly8Lys34(palmitoyl)-GLP-1-(7-36)(Human)-Lys6-NH2
<221> NAME/KEY: MOD_RES
<222> LOCATION: (28)
<223> OTHER INFORMATION: Lys(palmitoyl)

<400> SEQUENCE: 90

His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Lys Lys
            20                  25                  30

Lys Lys Lys Lys
        35

<210> SEQ ID NO 91
<211> LENGTH: 44
<212> TYPE: PRT
<213> ORGANISM: Artificial Sequence
<220> FEATURE:
<223> OTHER INFORMATION: Description of Artificial Sequence:
      des Ser39-exendin-4-Lys6-NH2

<400> SEQUENCE: 91

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Lys Lys Lys Lys Lys
        35                  40

<210> SEQ ID NO 92
<211> LENGTH: 45
<212> TYPE: PRT
<213> ORGANISM: Artificial Sequence
<220> FEATURE:
<223> OTHER INFORMATION: Description of Artificial Sequence:
      exendin-4-Lys6-NH2

<400> SEQUENCE: 92

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser Lys Lys Lys Lys Lys
        35                  40                  45

<210> SEQ ID NO 93
<211> LENGTH: 44
<212> TYPE: PRT
<213> ORGANISM: Artificial Sequence
<220> FEATURE:
<223> OTHER INFORMATION: Description of Artificial Sequence:
      des Pro36-exendin-4-Lys6-NH2

<400> SEQUENCE: 93

His Gly Glu Gly Thr Phe Thr Ser Asp Leu Ser Lys Gln Met Glu Glu
 1               5                  10                  15
```

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 94
<211> LENGTH: 44
<212> TYPE: PRT
<213> ORGANISM: Artificial Sequence
<220> FEATURE:
<223> OTHER INFORMATION: Description of Artificial Sequence:
      des Ala35-exendin-4-Lys6-NH2

<400> SEQUENCE: 94

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Pro Pro Pro Ser Lys Lys Lys Lys Lys Lys
        35                  40

<210> SEQ ID NO 95
<211> LENGTH: 44
<212> TYPE: PRT
<213> ORGANISM: Artificial Sequence
<220> FEATURE:
<223> OTHER INFORMATION: Description of Artificial Sequence:
      des Gly34-exendin-4-Lys6-NH2

<400> SEQUENCE: 95

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Ala Pro Pro Pro Ser Lys Lys Lys Lys Lys Lys
        35                  40

<210> SEQ ID NO 96
<211> LENGTH: 46
<212> TYPE: PRT
<213> ORGANISM: Artificial Sequence
<220> FEATURE:
<223> OTHER INFORMATION: Description of Artificial Sequence:
      des Ser39-(Lys40(palmitoyl))exendin-4-Lys7-NH2
<221> NAME/KEY: MOD_RES
<222> LOCATION: (39)
<223> OTHER INFORMATION: Lys(palmitoyl)

<400> SEQUENCE: 96

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Lys Lys Lys Lys Lys Lys Lys
        35                  40                  45

<210> SEQ ID NO 97
<211> LENGTH: 46
<212> TYPE: PRT
<213> ORGANISM: Artificial Sequence
<220> FEATURE:
<223> OTHER INFORMATION: Description of Artificial Sequence:
      des Gly34-(Lys40(palmitoyl))exendin-4-Lys7-NH2
<221> NAME/KEY: MOD_RES

```
<222> LOCATION: (40)
<223> OTHER INFORMATION: Lys(palmitoyl)

<400> SEQUENCE: 97

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Ala Pro Pro Pro Ser Lys Lys Lys Lys Lys Lys Lys
        35                  40                  45

<210> SEQ ID NO 98
<211> LENGTH: 46
<212> TYPE: PRT
<213> ORGANISM: Artificial Sequence
<220> FEATURE:
<223> OTHER INFORMATION: Description of Artificial Sequence:
      des Ala35-(Lys40(palmitoyl))exendin-4-Lys7-NH2
<221> NAME/KEY: MOD_RES
<222> LOCATION: (39)
<223> OTHER INFORMATION: Lys(palmitoyl)

<400> SEQUENCE: 98

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Pro Pro Pro Ser Lys Lys Lys Lys Lys Lys Lys
        35                  40                  45

<210> SEQ ID NO 99
<211> LENGTH: 46
<212> TYPE: PRT
<213> ORGANISM: Artificial Sequence
<220> FEATURE:
<223> OTHER INFORMATION: Description of Artificial Sequence:
      des Pro36-(Lys40(palmitoyl))exendin-4-Lys7-NH2
<221> NAME/KEY: MOD_RES
<222> LOCATION: (39)
<223> OTHER INFORMATION: Lys(palmitoyl)

<400> SEQUENCE: 99

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys Lys
        35                  40                  45

<210> SEQ ID NO 100
<211> LENGTH: 47
<212> TYPE: PRT
<213> ORGANISM: Artificial Sequence
<220> FEATURE:
<223> OTHER INFORMATION: Description of Artificial Sequence:
      Lys40(palmitoyl)exendin-4-Lys7-NH2
<221> NAME/KEY: MOD_RES
<222> LOCATION: (40)
<223> OTHER INFORMATION: Lys(palmitoyl)

<400> SEQUENCE: 100

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30
```

```
Ser Gly Ala Pro Pro Ser Lys Lys Lys Lys Lys Lys Lys
         35              40              45
```

<210> SEQ ID NO 101
<211> LENGTH: 38
<212> TYPE: PRT
<213> ORGANISM: Artificial Sequence
<220> FEATURE:
<223> OTHER INFORMATION: Description of Artificial Sequence:
      des Pro36-exendin-4-NH2

<400> SEQUENCE: 101

```
His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
             20                  25                  30

Ser Gly Ala Pro Pro Ser
         35
```

<210> SEQ ID NO 102
<211> LENGTH: 39
<212> TYPE: PRT
<213> ORGANISM: Homo sapiens
<220> FEATURE:
<223> OTHER INFORMATION: exendin-4-NH2

<400> SEQUENCE: 102

```
His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
             20                  25                  30

Ser Gly Ala Pro Pro Pro Ser
         35
```

<210> SEQ ID NO 103
<211> LENGTH: 36
<212> TYPE: PRT
<213> ORGANISM: Artificial Sequence
<220> FEATURE:
<223> OTHER INFORMATION: Description of Artificial Sequence:
      Gly8Lys26(palmitoyl)-GLP-1-(7-36)(Human)-Lys6-NH2
<221> NAME/KEY: MOD_RES
<222> LOCATION: (20)
<223> OTHER INFORMATION: Lys(palmitoyl)

<400> SEQUENCE: 103

```
His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Lys Lys
             20                  25                  30

Lys Lys Lys Lys
         35
```

<210> SEQ ID NO 104
<211> LENGTH: 38
<212> TYPE: PRT
<213> ORGANISM: Artificial Sequence
<220> FEATURE:
<223> OTHER INFORMATION: Description of Artificial Sequence:
      des Ser39-exendin-4-NH2

<400> SEQUENCE: 104

```
His Gly Glu Gly Thr Phe Thr Ser Asp Leu Ser Lys Gln Met Glu Glu
 1               5                  10                  15
```

Glu Ala Val Arg Leu Phe Ile Glu Trp Leu Lys Asn Gly Gly Pro Ser
            20                  25                  30

Ser Gly Ala Pro Pro Pro
        35

<210> SEQ ID NO 105
<211> LENGTH: 38
<212> TYPE: PRT
<213> ORGANISM: Artificial Sequence
<220> FEATURE:
<223> OTHER INFORMATION: Description of Artificial Sequence:
      des Ala35-exendin-4-NH2

<400> SEQUENCE: 105

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Pro Pro Pro Ser
        35

<210> SEQ ID NO 106
<211> LENGTH: 38
<212> TYPE: PRT
<213> ORGANISM: Artificial Sequence
<220> FEATURE:
<223> OTHER INFORMATION: Description of Artificial Sequence:
      des Gly34-exendin-4-NH2

<400> SEQUENCE: 106

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Ala Pro Pro Pro Ser
        35

<210> SEQ ID NO 107
<211> LENGTH: 39
<212> TYPE: PRT
<213> ORGANISM: Artificial Sequence
<220> FEATURE:
<223> OTHER INFORMATION: Description of Artificial Sequence:
      des Ser39-(Lys40 (palmitoyl))exendin-4-NH2
<221> NAME/KEY: MOD_RES
<222> LOCATION: (39)
<223> OTHER INFORMATION: Lys(palmitoyl)

<400> SEQUENCE: 107

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Lys
        35

<210> SEQ ID NO 108
<211> LENGTH: 39
<212> TYPE: PRT
<213> ORGANISM: Artificial Sequence
<220> FEATURE:
<223> OTHER INFORMATION: Description of Artificial Sequence:
      des Gly34-(Lys40 (palmitoyl))exendin-4-NH2
<221> NAME/KEY: MOD_RES

```
<222> LOCATION: (39)
<223> OTHER INFORMATION: Lys(palmitoyl)

<400> SEQUENCE: 108

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Ala Pro Pro Pro Ser Lys
        35

<210> SEQ ID NO 109
<211> LENGTH: 39
<212> TYPE: PRT
<213> ORGANISM: Artificial Sequence
<220> FEATURE:
<223> OTHER INFORMATION: Description of Artificial Sequence:
      des Ala35-(Lys40 (palmitoyl))exendin-4-NH2
<221> NAME/KEY: MOD_RES
<222> LOCATION: (39)
<223> OTHER INFORMATION: Lys(palmitoyl)

<400> SEQUENCE: 109

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Pro Pro Pro Ser Lys
        35

<210> SEQ ID NO 110
<211> LENGTH: 39
<212> TYPE: PRT
<213> ORGANISM: Artificial Sequence
<220> FEATURE:
<223> OTHER INFORMATION: Description of Artificial Sequence:
      des Pro36-(Lys40 (palmitoyl))exendin-4-NH2
<221> NAME/KEY: MOD_RES
<222> LOCATION: (39)
<223> OTHER INFORMATION: Lys(palmitoyl)

<400> SEQUENCE: 110

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Ser Lys
        35

<210> SEQ ID NO 111
<211> LENGTH: 31
<212> TYPE: PRT
<213> ORGANISM: Artificial Sequence
<220> FEATURE:
<223> OTHER INFORMATION: Description of Artificial Sequence:
      Gly8Lys37N-palmitoyl-GLP-1 (7-36)
<221> NAME/KEY: MOD_RES
<222> LOCATION: (31)
<223> OTHER INFORMATION: Lys(N-palmitoyl)

<400> SEQUENCE: 111

His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Lys
            20                  25                  30
```

<210> SEQ ID NO 112
<211> LENGTH: 30
<212> TYPE: PRT
<213> ORGANISM: Artificial Sequence
<220> FEATURE:
<223> OTHER INFORMATION: Description of Artificial Sequence:
      Gly8Lys34N-palmitoyl-GLP-1 (7-36)
<221> NAME/KEY: MOD_RES
<222> LOCATION: (28)
<223> OTHER INFORMATION: Lys(N-palmitoyl)

<400> SEQUENCE: 112

His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 113
<211> LENGTH: 30
<212> TYPE: PRT
<213> ORGANISM: Artificial Sequence
<220> FEATURE:
<223> OTHER INFORMATION: Description of Artificial Sequence:
      Gly8Lys26N-palmitoyl-GLP-1 (7-36)
<221> NAME/KEY: MOD_RES
<222> LOCATION: (20)
<223> OTHER INFORMATION: Lys(N-palmitoyl)

<400> SEQUENCE: 113

His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 114
<211> LENGTH: 30
<212> TYPE: PRT
<213> ORGANISM: Homo sapiens
<220> FEATURE:
<223> OTHER INFORMATION: GLP-1(7-36)

<400> SEQUENCE: 114

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 115
<211> LENGTH: 36
<212> TYPE: PRT
<213> ORGANISM: Artificial Sequence
<220> FEATURE:
<223> OTHER INFORMATION: Description of Artificial Sequence:
      Ser8-GLP-1(7-36)-Lys6

<400> SEQUENCE: 115

His Ser Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Lys Lys
            20                  25                  30

Lys Lys Lys Lys
        35

<210> SEQ ID NO 116

```
<211> LENGTH: 36
<212> TYPE: PRT
<213> ORGANISM: Artificial Sequence
<220> FEATURE:
<221> NAME/KEY: MOD_RES
<222> LOCATION: (2)
<223> OTHER INFORMATION: Aib
<223> OTHER INFORMATION: Description of Artificial Sequence:
      Aib8-GLP-1(7-36)-Lys6

<400> SEQUENCE: 116

His Xaa Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Lys Lys
             20                  25                  30

Lys Lys Lys Lys
         35

<210> SEQ ID NO 117
<211> LENGTH: 37
<212> TYPE: PRT
<213> ORGANISM: Artificial Sequence
<220> FEATURE:
<223> OTHER INFORMATION: Description of Artificial Sequence:
      Gly8-GLP-1(7-36)-Lys7

<400> SEQUENCE: 117

His Gly Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Lys Lys
             20                  25                  30

Lys Lys Lys Lys Lys
         35

<210> SEQ ID NO 118
<211> LENGTH: 42
<212> TYPE: PRT
<213> ORGANISM: Artificial Sequence
<220> FEATURE:
<223> OTHER INFORMATION: Description of Artificial Sequence:
      Lys6-Gly8-GLP-1(7-36)-Lys6

<400> SEQUENCE: 118

Lys Lys Lys Lys Lys Lys His Gly Glu Gly Thr Phe Thr Ser Asp Val
  1               5                  10                  15

Ser Ser Tyr Leu Glu Gly Gln Ala Ala Lys Glu Phe Ile Ala Trp Leu
             20                  25                  30

Val Lys Gly Arg Lys Lys Lys Lys Lys
         35                  40

<210> SEQ ID NO 119
<211> LENGTH: 36
<212> TYPE: PRT
<213> ORGANISM: Artificial Sequence
<220> FEATURE:
<223> OTHER INFORMATION: Description of Artificial Sequence:
      Lys6-Gly8-GLP-1(7-36)

<400> SEQUENCE: 119

Lys Lys Lys Lys Lys Lys His Gly Glu Gly Thr Phe Thr Ser Asp Val
  1               5                  10                  15

Ser Ser Tyr Leu Glu Gly Gln Ala Ala Lys Glu Phe Ile Ala Trp Leu
             20                  25                  30

Val Lys Gly Arg
```

-continued

```
                  35

<210> SEQ ID NO 120
<211> LENGTH: 38
<212> TYPE: PRT
<213> ORGANISM: Artificial Sequence
<220> FEATURE:
<223> OTHER INFORMATION: Description of Artificial Sequence:
      Gly8-GLP-1(7-36)-Lys8

<400> SEQUENCE: 120

His Gly Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Lys Lys
             20                  25                  30

Lys Lys Lys Lys Lys Lys
             35

<210> SEQ ID NO 121
<211> LENGTH: 40
<212> TYPE: PRT
<213> ORGANISM: Artificial Sequence
<220> FEATURE:
<223> OTHER INFORMATION: Description of Artificial Sequence:
      Gly8-GLP-1(7-36)-Lys10

<400> SEQUENCE: 121

His Gly Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Lys Lys
             20                  25                  30

Lys Lys Lys Lys Lys Lys Lys Lys
             35                  40

<210> SEQ ID NO 122
<211> LENGTH: 37
<212> TYPE: PRT
<213> ORGANISM: Artificial Sequence
<220> FEATURE:
<223> OTHER INFORMATION: Description of Artificial Sequence:
      Gly8-GLP-1(7-37)-Lys6

<400> SEQUENCE: 122

His Gly Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Gly Lys
             20                  25                  30

Lys Lys Lys Lys Lys
             35

<210> SEQ ID NO 123
<211> LENGTH: 31
<212> TYPE: PRT
<213> ORGANISM: Artificial Sequence
<220> FEATURE:
<223> OTHER INFORMATION: Description of Artificial Sequence:
      Gly8-GLP-1(7-37)

<400> SEQUENCE: 123

His Gly Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Gly
             20                  25                  30
```

<210> SEQ ID NO 124
<211> LENGTH: 31
<212> TYPE: PRT
<213> ORGANISM: Homo sapiens
<220> FEATURE:
<223> OTHER INFORMATION: GLP-1(7-37)

<400> SEQUENCE: 124

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30

<210> SEQ ID NO 125
<211> LENGTH: 28
<212> TYPE: PRT
<213> ORGANISM: Artificial Sequence
<220> FEATURE:
<223> OTHER INFORMATION: Description of Artificial Sequence:
      GLP-1(9-36)(Human)

<400> SEQUENCE: 125

Glu Gly Thr Phe Thr Ser Asp Val Ser Ser Tyr Leu Glu Gly Gln Ala
 1               5                  10                  15

Ala Lys Glu Phe Ile Ala Trp Leu Val Lys Gly Arg
            20                  25

<210> SEQ ID NO 126
<211> LENGTH: 39
<212> TYPE: PRT
<213> ORGANISM: Artificial Sequence
<220> FEATURE:
<223> OTHER INFORMATION: Description of Artificial Sequence:
      [Tyr39]exendin-4

<400> SEQUENCE: 126

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Tyr
        35

<210> SEQ ID NO 127
<211> LENGTH: 30
<212> TYPE: PRT
<213> ORGANISM: Homo sapiens
<220> FEATURE:
<223> OTHER INFORMATION: exendin-4 (1-31)

<400> SEQUENCE: 127

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30

<210> SEQ ID NO 128
<211> LENGTH: 30
<212> TYPE: PRT
<213> ORGANISM: Homo sapiens
<220> FEATURE:
<223> OTHER INFORMATION: exendin4 (9-39)

<400> SEQUENCE: 128

```
Leu Ser Lys Gln Met Glu Glu Ala Val Arg Leu Phe Ile Glu Trp
 1               5                  10                  15

Leu Lys Asn Gly Gly Pro Ser Ser Gly Ala Pro Pro Pro Ser
                20                  25                  30
```

<210> SEQ ID NO 129
<211> LENGTH: 38
<212> TYPE: PRT
<213> ORGANISM: Artificial Sequence
<220> FEATURE:
<223> OTHER INFORMATION: Description of Artificial Sequence:
      des Ser39-exendin-4

<400> SEQUENCE: 129

```
His Gly Glu Gly Thr Phe Thr Ser Asp Leu Ser Lys Gln Met Glu
 1               5                  10                  15

Glu Ala Val Arg Leu Phe Ile Glu Trp Leu Lys Asn Gly Gly Pro Ser
                20                  25                  30

Ser Gly Ala Pro Pro Pro
            35
```

<210> SEQ ID NO 130
<211> LENGTH: 37
<212> TYPE: PRT
<213> ORGANISM: Artificial Sequence
<220> FEATURE:
<223> OTHER INFORMATION: Description of Artificial Sequence:
      des-Pro36,Pro37-exendin-4

<400> SEQUENCE: 130

```
His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
                20                  25                  30

Ser Gly Ala Pro Ser
            35
```

<210> SEQ ID NO 131
<211> LENGTH: 43
<212> TYPE: PRT
<213> ORGANISM: Artificial Sequence
<220> FEATURE:
<223> OTHER INFORMATION: Description of Artificial Sequence:
      des-Pro36,Pro37-exendin-4-Lys6

<400> SEQUENCE: 131

```
His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
                20                  25                  30

Ser Gly Ala Pro Ser Lys Lys Lys Lys Lys
            35                  40
```

<210> SEQ ID NO 132
<211> LENGTH: 36
<212> TYPE: PRT
<213> ORGANISM: Artificial Sequence
<220> FEATURE:
<223> OTHER INFORMATION: Description of Artificial Sequence:
      des-Pro36,Pro37, Pro38-exendin-4

<400> SEQUENCE: 132

```
His Gly Glu Gly Thr Phe Thr Ser Asp Leu Ser Lys Gln Met Glu Glu
 1               5                  10                  15
```

Glu Ala Val Arg Leu Phe Ile Glu Trp Leu Lys Asn Gly Gly Pro Ser
            20                  25                  30

Ser Gly Ala Ser
        35

<210> SEQ ID NO 133
<211> LENGTH: 42
<212> TYPE: PRT
<213> ORGANISM: Artificial Sequence
<220> FEATURE:
<223> OTHER INFORMATION: Description of Artificial Sequence:
      des-Pro36,Pro37, Pro38-exendin-4-Lys6

<400> SEQUENCE: 133

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Ser Lys Lys Lys Lys Lys
        35                  40

<210> SEQ ID NO 134
<211> LENGTH: 42
<212> TYPE: PRT
<213> ORGANISM: Artificial Sequence
<220> FEATURE:
<223> OTHER INFORMATION: Description of Artificial Sequence:
      Lys6-des-Pro36 ,Pro37, Pro38-exendin-4

<400> SEQUENCE: 134

Lys Lys Lys Lys Lys Lys His Gly Glu Gly Thr Phe Thr Ser Asp Leu
 1               5                  10                  15

Ser Lys Gln Met Glu Glu Glu Ala Val Arg Leu Phe Ile Glu Trp Leu
            20                  25                  30

Lys Asn Gly Gly Pro Ser Ser Gly Ala Ser
        35                  40

<210> SEQ ID NO 135
<211> LENGTH: 48
<212> TYPE: PRT
<213> ORGANISM: Artificial Sequence
<220> FEATURE:
<223> OTHER INFORMATION: Description of Artificial Sequence:
      Lys6-des-Pro36 ,Pro37, Pro38-exendin-4-Lys6

<400> SEQUENCE: 135

Lys Lys Lys Lys Lys Lys His Gly Glu Gly Thr Phe Thr Ser Asp Leu
 1               5                  10                  15

Ser Lys Gln Met Glu Glu Glu Ala Val Arg Leu Phe Ile Glu Trp Leu
            20                  25                  30

Lys Asn Gly Gly Pro Ser Ser Gly Ala Ser Lys Lys Lys Lys Lys
        35                  40                  45

<210> SEQ ID NO 136
<211> LENGTH: 48
<212> TYPE: PRT
<213> ORGANISM: Artificial Sequence
<220> FEATURE:
<223> OTHER INFORMATION: Description of Artificial Sequence:
      Asn(Glu)5-des-Pro36,Pro37, Pro38-exendin-4-Lys6

<400> SEQUENCE: 136

Asn Glu Glu Glu Glu Glu His Gly Glu Gly Thr Phe Thr Ser Asp Leu

```
                1               5                  10                 15
Ser Lys Gln Met Glu Glu Ala Val Arg Leu Phe Ile Glu Trp Leu
                        20                 25                 30

Lys Asn Gly Gly Pro Ser Ser Gly Ala Ser Lys Lys Lys Lys Lys
        35                  40                 45

<210> SEQ ID NO 137
<211> LENGTH: 42
<212> TYPE: PRT
<213> ORGANISM: Artificial Sequence
<220> FEATURE:
<223> OTHER INFORMATION: Description of Artificial Sequence:
      Asn(Glu)5-des-Pro36,Pro37, Pro38-exendin-4

<400> SEQUENCE: 137

Asn Glu Glu Glu Glu Glu His Gly Glu Gly Thr Phe Thr Ser Asp Leu
 1               5                  10                 15

Ser Lys Gln Met Glu Glu Ala Val Arg Leu Phe Ile Glu Trp Leu
                 20                 25                 30

Lys Asn Gly Gly Pro Ser Ser Gly Ala Ser
         35                  40

<210> SEQ ID NO 138
<211> LENGTH: 40
<212> TYPE: PRT
<213> ORGANISM: Homo sapiens
<220> FEATURE:
<223> OTHER INFORMATION: Exendin-4 (1-40)

<400> SEQUENCE: 138

His Gly Glu Gly Thr Phe Thr Ser Asp Leu Ser Lys Gln Met Glu Glu
 1               5                  10                 15

Glu Ala Val Arg Leu Phe Ile Glu Trp Leu Lys Asn Gly Gly Pro Ser
                 20                 25                 30

Ser Gly Ala Pro Pro Pro Ser Gly
         35                  40

<210> SEQ ID NO 139
<211> LENGTH: 39
<212> TYPE: PRT
<213> ORGANISM: Artificial Sequence
<220> FEATURE:
<223> OTHER INFORMATION: Description of Artificial Sequence:
      des-Pro36-exendin-4 (1-40)

<400> SEQUENCE: 139

His Gly Glu Gly Thr Phe Thr Ser Asp Leu Ser Lys Gln Met Glu Glu
 1               5                  10                 15

Glu Ala Val Arg Leu Phe Ile Glu Trp Leu Lys Asn Gly Gly Pro Ser
                 20                 25                 30

Ser Gly Ala Pro Pro Ser Gly
         35

<210> SEQ ID NO 140
<211> LENGTH: 37
<212> TYPE: PRT
<213> ORGANISM: Artificial Sequence
<220> FEATURE:
<223> OTHER INFORMATION: Description of Artificial Sequence:
      des-Pro36,Pro37, Pro38-exendin-4 (1-40)

<400> SEQUENCE: 140

His Gly Glu Gly Thr Phe Thr Ser Asp Leu Ser Lys Gln Met Glu Glu
```

```
                1               5              10              15
           Glu Ala Val Arg Leu Phe Ile Glu Trp Leu Lys Asn Gly Gly Pro Ser
                        20              25              30
           Ser Gly Ala Ser Gly
                   35
```

<210> SEQ ID NO 141
<211> LENGTH: 6
<212> TYPE: PRT
<213> ORGANISM: Artificial Sequence
<220> FEATURE:
<223> OTHER INFORMATION: Description of Artificial Sequence:
      Synthetic Peptide Sequence

<400> SEQUENCE: 141

```
Asn Glu Glu Glu Glu Glu
 1               5
```

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence:
      Synthetic Peptide Sequence

<400> SEQUENCE: 142

```
Asn Glu Glu Glu Glu Glu Glu
 1               5
```

<210> SEQ ID NO 143
<211> LENGTH: 6
<212> TYPE: PRT
<213> ORGANISM: Artificial Sequence
<220> FEATURE:
<223> OTHER INFORMATION: Description of Artificial Sequence:
      Synthetic Peptide Sequence

<400> SEQUENCE: 143

```
Gln Glu Glu Glu Glu Glu
 1               5
```

<210> SEQ ID NO 144
<211> LENGTH: 6
<212> TYPE: PRT
<213> ORGANISM: Artificial Sequence
<220> FEATURE:
<223> OTHER INFORMATION: Description of Artificial Sequence:
      Synthetic Peptide Sequence

<400> SEQUENCE: 144

```
Asn Asp Asp Asp Asp Asp
 1               5
```

<210> SEQ ID NO 145
<211> LENGTH: 6
<212> TYPE: PRT
<213> ORGANISM: Artificial Sequence
<220> FEATURE:
<223> OTHER INFORMATION: Description of Artificial Sequence:
      Synthetic Peptide Sequence

<400> SEQUENCE: 145

```
Gln Asp Asp Asp Asp Asp
 1               5
```

-continued

<210> SEQ ID NO 146
<211> LENGTH: 138
<212> TYPE: DNA
<213> ORGANISM: Artificial Sequence
<220> FEATURE:
<223> OTHER INFORMATION: Description of Artificial Sequence: Synthetic
      cDNA

<400> SEQUENCE: 146
atgcatggtg agggtacatt cacatctgat ttgtctaagc aaatggagga ggaggctgtt      60
cgtttgttca ttgagtggtt gaagaatggt ggtccatctt ctggtgctcc accatctaag     120
aagaagaaga agaagtaa                                                   138

<210> SEQ ID NO 147
<211> LENGTH: 32
<212> TYPE: PRT
<213> ORGANISM: Artificial Sequence
<220> FEATURE:
<221> NAME/KEY: MOD_RES
<222> LOCATION: (32)
<223> OTHER INFORMATION: Lys(palmitoyl)
<223> OTHER INFORMATION: Description of Artificial Sequence:
      Gly8-Glp-1(7-36)-Lys37(palmitoyl)(Human)

<400> SEQUENCE: 147

His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly Lys
            20                  25                  30

<210> SEQ ID NO 148
<211> LENGTH: 31
<212> TYPE: PRT
<213> ORGANISM: Artificial Sequence
<220> FEATURE:
<223> OTHER INFORMATION: Description of Artificial Sequence:
      Y31-exendin-4 (1-31)(Human)

<400> SEQUENCE: 148

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Lys
            20                  25                  30

<210> SEQ ID NO 149
<211> LENGTH: 44
<212> TYPE: PRT
<213> ORGANISM: Artificial Sequence
<220> FEATURE:
<223> OTHER INFORMATION: Description of Artificial Sequence:
      Lys6-des-Pro36-exendin-4

<400> SEQUENCE: 149

Lys Lys Lys Lys Lys Lys His Gly Glu Gly Thr Phe Thr Ser Asp Leu
 1               5                  10                  15

Ser Lys Gln Met Glu Glu Glu Ala Val Arg Leu Phe Ile Glu Trp Leu
            20                  25                  30

Lys Asn Gly Gly Pro Ser Ser Gly Ala Pro Pro Ser
        35                  40

<210> SEQ ID NO 150
<211> LENGTH: 50
<212> TYPE: PRT
<213> ORGANISM: Artificial Sequence

```
<220> FEATURE:
<223> OTHER INFORMATION: Description of Artificial Sequence:
      Lys6-des-Pro36-exendin-4-Lys6

<400> SEQUENCE: 150

Lys Lys Lys Lys Lys Lys His Gly Glu Gly Thr Phe Thr Ser Asp Leu
 1               5                  10                  15

Ser Lys Gln Met Glu Glu Glu Ala Val Arg Leu Phe Ile Glu Trp Leu
            20                  25                  30

Lys Asn Gly Gly Pro Ser Ser Gly Ala Pro Pro Ser Lys Lys Lys Lys
        35                  40                  45

Lys Lys
     50

<210> SEQ ID NO 151
<211> LENGTH: 40
<212> TYPE: PRT
<213> ORGANISM: Artificial Sequence
<220> FEATURE:
<221> NAME/KEY: MOD_RES
<222> LOCATION: (40)
<223> OTHER INFORMATION: Lys(palmitoyl)
<223> OTHER INFORMATION: Description of Artificial Sequence:
      (Lys40(palmitoyl)exendin-4 (1-39)

<400> SEQUENCE: 151

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 152
<211> LENGTH: 39
<212> TYPE: PRT
<213> ORGANISM: Artificial Sequence
<220> FEATURE:
<221> NAME/KEY: MOD_RES
<222> LOCATION: (39)
<223> OTHER INFORMATION: Lys(palmitoyl)
<223> OTHER INFORMATION: Description of Artificial Sequence:
      [Des pro36, Lys40(palmitoyl)]exendin-4(1-40)(Human)

<400> SEQUENCE: 152

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Ser Lys
        35

<210> SEQ ID NO 153
<211> LENGTH: 37
<212> TYPE: PRT
<213> ORGANISM: Artificial Sequence
<220> FEATURE:
<223> OTHER INFORMATION: Description of Artificial Sequence:
      Gly8Lys37(palmitoyl)-Glp-1-(7-36)(Human)-Lys6

<400> SEQUENCE: 153

His Gly Glu Gly Thr Phe Thr Ser Asp Val Ser Ser Tyr Leu Glu Gly
 1               5                  10                  15
```

―continued

```
Gln Ala Ala Lys Glu Phe Ile Ala Trp Leu Val Lys Gly Arg Lys Lys
             20                  25                  30
Lys Lys Lys Lys Lys
         35
```

PEPTIDE AGONISTS OF GLP-1 ACTIVITY

This application claims benefit of U.S. Provisional application Ser. No. 60/143,591, filed on Jul. 12, 1999.

FIELD OF THE INVENTION

The present invention relates to novel peptide agonists of GLP-1 activity. More specifically the invention relates to novel peptides that lower blood glucose levels comprising variants of the exendin-4 polypeptide sequence and peptide conjugates comprising variants of the GLP-1 or the exendin-4 polypeptide sequences which are pharmacologically active and stable, and as agonists of GLP-1 activity are useful in the treatment of diseases that benefit from regulation or excess levels of blood glucose and/or regulation of gastric emptying, such as diabetes and eating disorders. The present invention also relates to methods of preparing said novel peptides, a composition, e.g., a pharmaceutical composition, comprising a peptide of the invention and a physiologically acceptable carrier, to said peptide for use in therapy, a method of treating a disorder and to the use of said peptide for the manufacture of a pharmaceutical composition for use in therapy.

BACKGROUND OF THE INVENTION

A number of hormones that lower blood glucose levels are released from the gastrointestinal mucosa in response to the presence and absorption of nutrients in the gut. These include gastrin, secretin, glucose-dependent insulinotropic polypeptide (GIP) and glucagon-like peptide-1 (GLP-1). The most potent substance known is GLP-1 (Øorskov, 1992, Diabetologia 35:701–711). Glucagon-like peptide 1 (GLP-1) is a product of proglucagon, a 180 amino acid peptide (Drucker, 1998 Diabetes 47:159–169). The overall sequence of proglucagon contains the 29-amino acid sequences of glucagon, the 36 or 37 amino acid sequence of GLP-1 and the 34 amino acid sequence of glucagon-like peptide-2 (GLP-2), an intestinotrophic peptide. GLP-1 has a number of functions. It is a physiological hormone that enhances the effect on insulin secretion in normal humans and is therefore an incretin hormone. In addition, GLP-1 also lowers glucagon concentrations, slows gastric emptying, stimulates (pro) insulin biosynthesis, and enhances insulin sensitivity (Nauck, 1997, Horm. Metab. Res. 47:1253–1258). The peptide also enhances the ability for the β-cells to sense and respond to glucose in subjects with imparted glucose tolerance (Byrne, 1998, Eur. J. Clin. Invest. 28:72–78). The insulinotropic effect of the GLP-1 in humans increases the rate of glucose disappearance partly because of increased insulin levels and partly because of enhanced insulin sensitivity (D'Alessio, 1994, Eur. J. Clin. Invest. 28:72–78). This has placed GLP-1 as a promising agent for treatment of type II diabetes. Active fragments of GLP-1 have been found to be GLP-1(7–36) and GLP-1(7–37). However, a major pharmacological problem with native GLP-1 is its short half-life. In humans and rats, GLP-1 is rapidly degraded by dipeptidyl peptidase-IV (DPP-IV) into GLP-1(9–36)amide, acting as an endogenous GLP-1 receptor antagonist (Deacon, 1998, Diabetologia 41:271–278). Several strategies circumventing this problem have been proposed, some using inhibitors of DPP-IV and other DPP-IV resistant analogues of GLP-1 (7–36)amide (Deacon, 1998, Diabetologia 41:271–287; Deacon et al., 1998, Diabetes 47:764–769; Ritzel, 1998, J. Endocrinol. 159:93–102; U.S. Pat. No. 5,545,618; Pederson, 1998, Diabetes 47:1253–1258).

Exendins, another group of peptides that lower blood glucose levels have some sequence similarity (53%) to GLP-1[7–36]NH$_2$ (Goke et al., 1993, J. Biol. Chem. 268:19650–55). The exendins are found in the venom of Helodermatidae or beaded lizards (Raufman, 1996, Reg. Peptides 61:1–18). Exendin-3 is present in the venom of *Heloderma horridum*, the Mexican beaded lizard and exendin-4 is present in the venom of *Heloderma suspectum*, the Gila monster. Exendin-4 differs from exendin-3 at just positions two and three. The cDNA encoding the exendin-4 precursor protein, a 47 amino acid peptide fused to the amino terminus of exendin-4 has been cloned and sequenced (Pohl et al., 1998, J. Biol. Chem. 273:9778–9784 and WO98/35033). Both exendin-3 and exendin-4 stimulate an increase in cellular cAMP production in guinea pig pancreatic acinar cells by interacting with exendin receptors (Raufman, 1996, Reg. Peptides 61:1–18). Exendin-3 causes a biphasic increase in cellular cAMP production, but a monophasic increase in amylase release in pancreatic acinar cells. In contrast, exendin-4 causes a monophasic increase in cAMP production and does not alter amylase release.

Exendin-4 is a strong GLP-1 receptor agonist on isolated rat insulinoma cells (Goke et al., 1993, J. Biol. Chem. 268:19650–55). This is expected as the (His Ala) domain of GLP-1 recognised by DPP-IV is not present in exendin-4 (Goke et al., 1993, J. Biol Chem. 268:19650–55). Binding of [$^{125}$I]GLP-1 to the nucleus of the solitary tract was inhibited concentration-dependently by unlabelled GLP-1 and [Tyr39]exendin-4 with Ki values of 3.5 and 9.4 nM respectively, and similar values are found in cell lines (Goke et al., 1995, Eur. J. Neurosci. 7:2294–2300 and Goke et al., 1993, J. Biol. Chem. 268:19650–55). Further, exendin-4 given systemically lowers blood glucose levels by 40% in diabetic db/db mice (WO/99/07404). Recently, Grieg et al. (1999, Diabetologia 42:45–50) has shown a long lasting blood glucose lowering effect of once daily intraperitoneal injection of exendin-4 to diabetic ob/ob mice). U.S. Pat. No. 5,424,286 discloses that a considerable portion of the N-terminal sequence is essential in order to preserve insulinotropic activity (exendin-4(1–31) and Y$^{31}$-exendin-4 (1–31)) whereas an N-terminally truncated exendin (exendin-4(9–39) has inhibitory properties.

The use of exendin-3, exendin-4 and exendin agonists has been proposed for the treatment of diabetes mellitus, reducing gastric motility and delaying gastric emptying and the prevention of hyperglycemia (U.S. Pat. No. 5,424,286, WO98/0535) as well as for the reduction of food intake (WO98/30231). There has been proposed ways of obtaining novel compounds by modifying the native exendin sequences. One way is to attach lipophilic substituents to the molecule, e.g. as described in WO 99/43708 which discloses derivatives of exendin with just one lipophilic substituent attached to the C-terminal amino acid residue.

A major approach has been to devise exendin analogues characterised by amino acid substitutions and/or C-terminal truncation of the native exendin-4 sequence. This approach is represented by the compounds of WO99/07404, WO 99/25727 and WO 99/22728. WO99/07404 discloses exendin agonists having a general formula I that defines a peptide sequence of 39 amino acid residues with Gly Thr in positions 4–5, Ser Lys GLn in positions 11–13, Glu Glu Glu Ala Val Arg Leu in positions 15–21, Leu Lys Asn Gly Gly in positions 26–30, Ser Ser Gly Ala in positions 32–35, and wherein the remaining positions may be occupied by wild-type exendin amino acid residues or may be occupied by specified amino acid substitutions. The formula I does not cover any exendin agonists or analogues having specific amino acid deletions and/or being conjugates as described herein, such as the novel compounds desPro$^{36}$-exendin-4

(1–39), exendin-4(1–39)-K$_6$ or desPro$^{36}$-exendin-4(1–39)-K$_6$. WO 99/25727 discloses exendin agonists having a general formula I that defines a peptide sequence of from 28 to 38 amino acid residues with Gly in position 4 and Ala in position 18, and wherein the remaining positions may be occupied by wild-type exendin amino acid residues or may be occupied by specified amino acid substitutions. Formula I does not comprise a peptide sequence having Ser as the C-terminal amino acid and exendin agonists or analogues having specific amino acid deletions and/or being conjugates as described herein, such as the novel compounds desPro$^{36}$-exendin-4(1–39), exendin-4(1–39)-K$_6$ or desPro$^{36}$-exendin-4)1–39)-K$_6$. Further, formula II of WO 99/25727 defines a peptide sequence similar to formula I, but including exendin derivatives having a C(1–10)alkanoyl or cycloalkylalkanoyl substituent on lysine in position 27 or 28. When treating inappropriate post-prandial blood glucose levels the compounds are administered frequently, for example one, two or three times a day. WO 99/25728 discloses exendin agonists having a general formula I that defines a peptide sequence of from 28 to 39 amino acid residues with fixed Ala in position 18, and wherein the remaining positions may be occupied by wild-type exendin amino acid residues or may be occupied by specified amino acid substitutions. Said exendin agonists all correspond to a truncated exendin analogues having a varying degree of amino acid substitutions. Peptide sequences of from 34 to 38 amino acid residues do not have Ser C-terminally. A peptide sequence of 39 amino acid residues may have either Ser or Tyr C-terminally, but no further residues. Exendin agonist or analogues having specific amino acid deletions and/or being conjugates according to the invention described herein are not comprised by formula I. Further, formula II defines a peptide sequence similar to formula I, but including exendin derivatives having a C(1–10)alkanoyl or cycloalkylalkanoyl substituent on lysine in position 27 or 28.

WO 99/46283 (published 16.09.99) discloses peptide conjugates comprising a pharmacologically active peptide X and a stabilising peptide sequence Z of 4–20 amino acid residues covalently bound to X, where said conjugates are characterised in having an increased half-life compared to the half-life of X. X may be exendin-4 or exendin-3.

OBJECTIVE OF THE INVENTION

There is a need for compounds that lower blood glucose levels in mammals, and are stable and effective. Therefore, it is an objective of the invention to provide novel compounds that lower blood glucose levels in mammals. Ideally, these should be effective when administered orally. It is a further object of the invention to provide novel peptide agonists of GLP-1 activity and/or exendin-4 activity. It is a still further purpose of the invention to provide peptide agonists of GLP-1 activity and/or exendin-4 activity having an increased half-life and/or a decreased clearance.

SUMMARY OF THE INVENTION

The invention is directed to a peptide conjugate comprising a peptide X selected from the group consisting of
(a) an exendin having at least 90% homology to exendin-4;
(b) a variant of said exendin wherein said variant comprises a modification selected from the group consisting of between one and five deletions at positions 34–39 and contains a Lys at position 40 having a lipophilic substituent; or
(c) GLP-1 (7–36) or GLP-1 (7–37) having at least one modification selected from the group consisting of:

(i) substitution of D-alanine, glycine or alpha-amino isobutyric acid for alanine at position 8 and
(ii) a lipophilic substituent;

and Z, a peptide sequence of 4–20 amino acid units covalently bound to said variant, wherein each amino acid unit in said peptide sequence, Z is selected from the group consisting of Ala, Leu, Ser, Thr, Tyr, Asn, Gln, Asp, Glu, Lys, Arg, His, Met, Orn, and amino acid units of the general formula I

$$—NH—C(R^1)(R^2)—C(=O)— \quad (I)$$

wherein R$^1$ and R$^2$ are selected from the group consisting of hydrogen, C$_{1-6}$-alkyl, phenyl, and phenyl-methyl, wherein C$_{1-6}$-alkyl is optionally substituted with from one to three substituents selected from halogen, hydroxy, amino, cyano, nitro, sulfono, and carboxy, and phenyl and phenyl-methyl is optionally substituted with from one to three substituents selected from C$_{1-6}$-alkyl, C$_{2-6}$-alkenyl, halogen, hydroxy, amino, cyano, nitro, sulfono, and carboxy, or R$^1$ and R$^2$ together with the carbon atom to which they are bound form a cyclopentyl, cyclohexyl, or cycloheptyl ring, e.g., 2,4-diaminobutanoic acid and 2,3-diaminopropanoic acid, with the proviso that X is not exendin-4 or exendin-3.

The peptide X is further characterised in being effective in improving glucose tolerance in a diabetic mammal.

Furthermore, the invention is directed to a novel variant of a parent exendin, wherein said parent exendin has an amino acid sequence having at least an 90% homology to exendin-4 and wherein said variant lowers the blood glucose level in a mammal, binds to a GLP-1 receptor and has at least one modification selected from the group consisting of (a) between one and five deletions at positions 34–38, and (b) contains a Lys at position 40 having a lipophilic substituent attached to the epsilon amino group of said lysine.

DETAILED DESCRIPTION OF THE INVENTION

Figure 1:
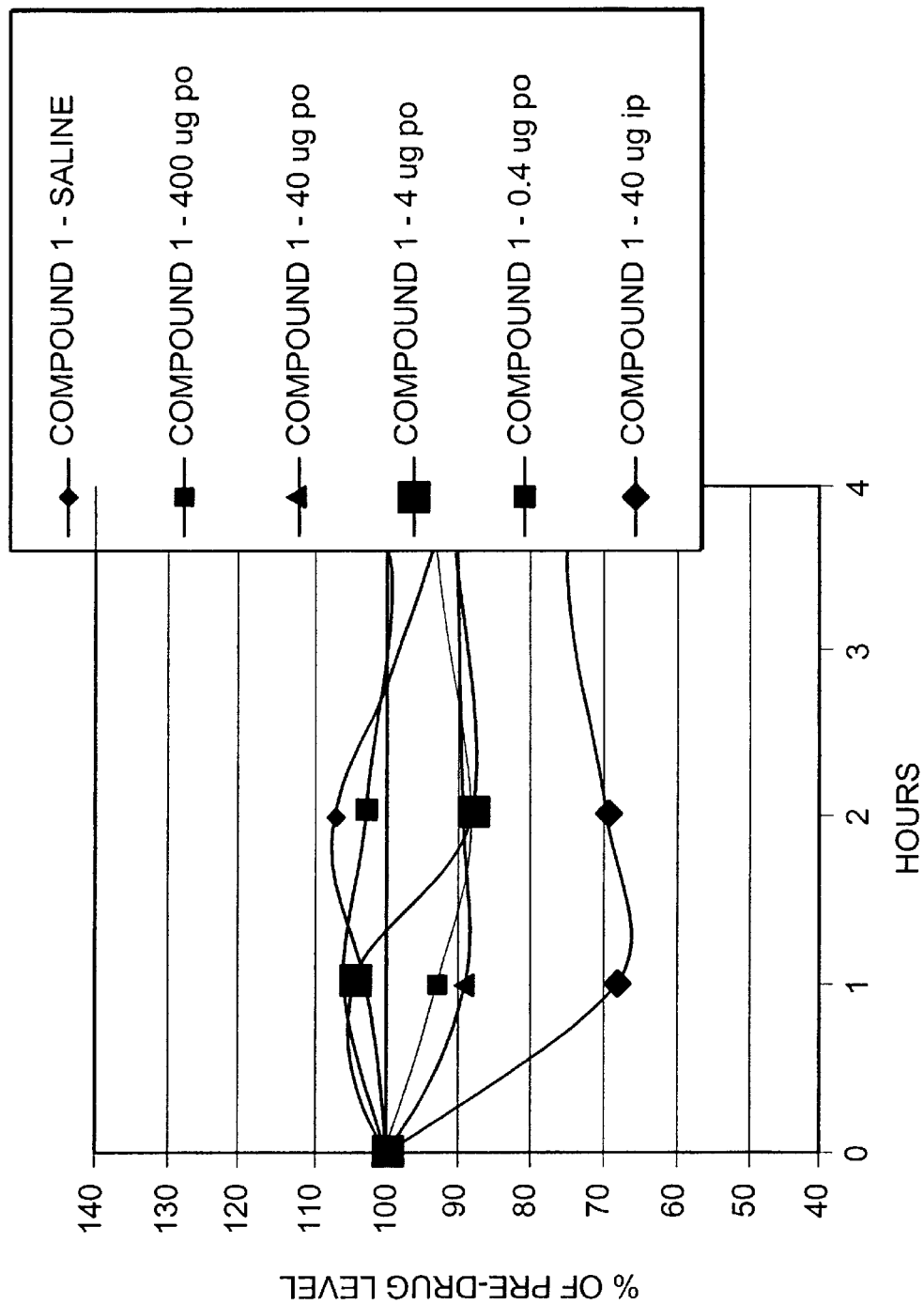
FIG. 1 shows the effect of Compound 1 (SEQ ID NO:101) (des PRO$^{36}$-exendin-4(1–39)-NH$_2$) on blood glucose levels of mice, cf. Example 25.

The compounds of the present invention include hitherto unknown deletion variants of a parent exendin. In contrast to know substitution and/or truncation variants of exendin-4 (1–39) the novel compounds are believed to exhibit a stabilised alpha-helix structure with superior stability properties and unreduced or enhanced binding properties. Moreover, conjugation of the novel variants, modified GLP-1(7–36)-NH$_2$, and modified GLP-1-(7–37) to specific short peptide sequences (Z) render stability to these compounds without compromising the pharmacological properties. These conjugations confer in vivo stability and hydrophilicity to the peptide molecule. The Z is composed of 10 amino-acid residues, and has alone no structural characteristics in terms of α-helix conformation. However, from studies using both circular dichroism and nuclear magnetic resonance (NMR) spectroscopy, addition of Z dramatically alters the structural characteristics of some peptides as evidenced by the increased amount of α-helix conformation in the peptide. For example, circular dichroism, demonstrated that a Z-modified (Gly$^8$)-GLP-1 had much more α-helix conformation than (Gly$^8$)-GLP-1. Together with the pharmacological results, the structural analyses suggest that Z is modifying the conformation of the peptide leading to higher enzyme-stability, but without losing its potency. Also the physical and chemical properties of peptides may be altered considerably by Z-modification with resulting impact on pharmacological formulation strategy.

Exendin Variants

The exendin variant of the present invention is a variant of a parent exendin peptide having at least about 90% homology and most preferably at least about 95% to exendin-4, which have exendin activity, e.g., lowers the blood glucose level in a mammal and binds to a GLP-1 receptor. In a preferred embodiment, the parent exendin peptide has an amino acid sequence which differs by five amino acids, preferably by four amino acids, more preferably by three amino acids, even more preferably by two amino acids, and still more preferably by one amino acid residue from the amino acid sequence of exendin-4)1–39).

In one embodiment, the exendin variant comprises between one and five deletions at positions 34–38. Preferably the variant comprises between 1 and 4 deletions at positions 34–38, more preferably between 1 and 3 deletions at positions 36–38. Preferably the parent exendin is exendin-4, and a preferred variant included as peptide X in the peptide conjugates herein has an amino acid sequence wherein 1, 2 or 3 of the Pro residues in positions 36, 37 and 38 have been deleted from the amino acid sequence of exendin-4 and preferably from the amino acid sequence of exendin-4(1–39).

Coupling of a Z sequence to the X peptide herein is believed to increase the stability of these compounds. Proline is a rigid amino acid that may interfere with the effect of Z to stabilise the structure of the X peptide. Deletion of one, two or all of the proline amino acids in positions 36, 37 and 38 of the exendin backbone is therefore preferred in the peptide conjugates comprising a variant of a parent exendin according to the invention, as long as the efficacy of said conjugates as measured in, e.g. an oral glucose tolerance test (OGTT) in diabetic db/db mice, is not negatively affected.

In another embodiment, the variant comprises an additional residue at position 40, a lysine residue which comprises a lipophilic substituent bound to the epsilon amino group of lysine via an amide bond. The lipophilic substituent may be the acyl group of a straight-chain or branched fatty acid or a straight-chain or branched alkane α,ω-dicarboxylic acid. The acyl group may have the formula $CH_3(CH_2)_nCO-$, wherein n is a integer from 4–38 and preferably from 4–24. In a specific embodiment, the acyl group is selected from the group consisting of $CH_3(CH_2)_6CO-$, $CH_3(CH_2)_8CO-$, $CH_3(CH_2)_{10}CO-$, $CH_3(CH_2)_{12}CO-$, $CH_3(CH_2)_{14}CO-$, $CH_3(CH_2)_{16}CO-$, $CH_3(CH_2)_{18}CO-$, $CH_3(CH_2)_{20}CO-$, and $CH_3(CH_2)_{22}CO-$. The acyl group may have the formula $HOOC(CH_2)_mCO-$, wherein n is an integer from 4–38 and preferably from 4–24. In a specific embodiment, the acyl group is selected from the group consisting of $HOOC(CH_2)_{14}CO-$, $HOOC(CH_2)_{16}CO-$, $HOOC(CH_2)_{18}CO-$, $HOOC(CH_2)_{20}CO-$ and $HOOC(CH_2)_{22}CO-$. In a more specific embodiment, the lipophilic substituent is selected from the group consisting of tetradecanoyl, ω-carboxynonadecanoyl, 7-deoxycholoyl, choloyl, palmitoyl and lithocholoyl. In a most specific embodiment, the lipophilic substituent is palmitoyl.

Alternatively, the liphophilic substituent may have an NH group. Specific embodiments include but are not limited to the formulae $CH_3(CH_2)_a((CH_2)_bCOOH)CHNHCO(CH_2)_2CO-$ wherein a and b are integers and a+b is an integer of from 8 to 33, preferably from 12 to 28;

$CH_3(CH_2)_cCONHCH(COOH)(CH_2)_2CO-$ wherein c is an integer of from 10 to 24;

$CH_3(CH_2)_dCONHCH(CH_2)_2(COOH)CO-$ wherein d is an integer of from 8 to 24;

$COOH(CH_2)_eCO-$ wherein e is an integer of from 8 to 24;

$-NHCH(COOH)(CH_2)_4NHCO(CH_2)_fCH_3$ wherein f is a integer of from 8 to 18;

$-NHCH(COOH)(CH_2)_4NHCOCH(CH_2)_2COOH)NHCO(CH_2)_gCH_3$ wherein g is an integer of from 10 to 16; and $-NHCH(COOH)(CH_2)_4NHCO)CH_2)_2CH(COOH)NHCO(CH_2)_hCH_3$ wherein h is an integer of 0 or from 1 to 22 and preferably from 10 to 16.

The exendin variants having a lysine residue at position 40 carrying a lipophilic substituent optionally further comprise between one and five deletions, preferably between one and three deletions, at positions 34 to 39, preferably at positions 34–38, such as [des Ser$^{39}$, Lys$^{40}$ (palmitoyl)] exendin-4(1–39), [des Pro$^{36}$, Lys$^{40}$ (palmitoyl)]exendin-4(1–39) and [des Pro$^{36}$, Lys$^{40}$ (palmitoyl)]exendin-4(1–40).

The variant may be in a most specific embodiment selected from the group consisting of:

Compound 1: des Pro$^{36}$-exendin-4(1–39)-NH$_2$ (SEQ ID NO:101), des Pro$^{36}$-exendin-4(1–40)-NH$_2$, Compound 14: des Pro$^{36}$, Pro$^{37}$, Pro$^{38}$exendin-4(1–39)-NH$_2$, des Pro$^{36}$, Pro$^{37}$, Pro$^{38}$-exendin-4(1–40)-NH$_2$, des Pro$^{36}$, Pro$^{37}$-exendin-4(1–39)-NH$_2$, des Ala$^{35}$-exendin-4(1–39)-NH$_2$ (SEQ ID NO:105), des Gly$^{34}$-exendin-4(1–39)-NH$_2$ (SEQ ID NO:106), des Ser$^{39}$-(Lys$^{40}$ (palmitoyl))exendin-4(1–39)-NH$_2$ (SEQ ID NO:107), des Gly$^{34}$-(Lys$^{40}$ (palmitoyl))exendin-4(1–39)-NH$_2$ (SEQ ID NO:108), des Ala$^{35}$-(Lys$^{40}$ (palmitoyl))exendin-4(1–39)-NH$_2$ (SEQ ID NO:109), des Pro$^{36}$-(Lys$^{40}$ (palmitoyl))exendin-4(1–39)-NH$_2$ (SEQ ID NO:110), and the free acid thereof and a pharmaceutically acceptable salt thereof.

Modified GLP-1

A preferred modified GLP-1 included as peptide X in the peptide conjugates herein has an amino acid sequence of GLP-1 (7–36)-NH$_2$ or GLP-1 (7–37) having a substitution of glycine for alanine at position 8. Alternatively, a preferred modified GLP-1 has an amino acid sequence of GLP-1 (7–36) or GLP-1 (7–37) having a substitution of glycine for alanine at position 8 and a lipophilic substituent, preferably palmitoyl, on one lysine residue at position 26, 34 or 37. The lipophilic substituent is preferably attached to the epsilon amino group of said lysine and includes the specific embodiments described above for the exendin variants. The modified GLP-1(7–36) or GLP-1(7–37) used as X in the conjugates of the invention may be those cited in WO 99/43707 and WO 98/08871 comprising a lipophilic substituent or, more preferably those GLP-1 analogues having a glycine substitution at position 8. Preferred peptides X are
Gly$^8$-GLP-1(7–36),
Gly$^8$-GLP-1(*7–37), and
Gly$^8$-GLP-1(7–36)-Lys$^{37}$ (palmitoyl).

The compounds of the invention having a lipophilic substituent would have a more protracted profile of action than the parent peptides as demonstrated for GLP-1 derivatives in WO 98/08871.

Peptide conjugates

The peptide sequence Z may be bound to the C-terminal or the N-terminal of the peptide sequence, X or two peptide sequences may be bound individually to both the C- and N-terminal of X. In case the native peptide X possesses a free C-terminal carboxylic acid, the peptide sequence Z may be attached to either the C-terminal of the peptide X or to the N-terminal of the peptide X, or the C- and N-terminal of X may both be bound to each individual peptide sequence Z. Alternatively, Z may be bound to the nitrogen atom on the side chain of lysine, histidine or arginine or a carbonyl function on the side chain of glutamic acid or aspartic acid anywhere with the peptide sequence X. In one embodiment, Z may be attached to X within the sequence and to the N- and/or C-terminal of X. Whether the sequence should be attached to the peptide sequence X as its C-terminal, at its N-terminal, or both, or within the peptide sequence X depends on the specific peptide X and can be easily determined by the person skilled in the art. Preferably, X is bound to Z via a peptide bond and preferably at the C-terminal of X.

One aspect of the invention is directed to a peptide conjugate comprising a peptide X which reduces the blood glucose level in a mammal, wherein X is (a) an exendin having at least 90% homology to exendin-4: (b) a variant of said exendin wherein said variant comprises a modification selected from the group consisting between One and five deletions at positions 34–39 and contains a Lys at position 40 having a lipophilic substituent; or (c) GLP-1 (7–36) or GLP-1 (7–37) having at least one modification selected from the group consisting of: (i) substitution of D-alanine, glycine or alpha-amino isobutyrel acid (Aib) for alanine at position 8 and (ii) a lipophilic substituent; and Z, a peptide sequence of 4–20 amino acid units covalently bound to X, wherein each amino acid unit in said peptide sequence Z is selected from the group consisting of Ala, Leu, Ser, Thr, Tyr, Asn, Gln, Asp, Glu, Lys, Arg, His, Met, Orn, and amino acid units of the general formula I

—NH—C(R$^1$)(R$^2$)—C(=O)— (I)

wherein R$^1$ and R$^2$ are selected from the group consisting of hydrogen, $C_{1-6}$-alkyl, phenyl, and phenyl-methyl, wherein $C_{1-6}$-alkyl is optionally substituted with from one to three substituents selected from halogen, hydroxy, amino, cyano, nitro, sulfono, and carboxy, and phenyl and phenyl-methyl is optionally substituted with from one to three substituents selected from $C_{1-6}$-alkyl, $C_{2-6}$-alkenyl, halogen, hydroxy, amino, cyano, nitro, sulfono, and carboxy, or R$^1$ and R$^2$ together with the carbon atom to which they are bound form a cyclopentyl, cyclohexyl, or cycloheptyl ring, e.g., 2,4-diaminobutanoic acid and 2,3-diaminopropanoic acid. Preferably, X binds to a GLP-1 receptor and does not include exendin-4 or exendin-3.

Z is typically a peptide sequence of 4–20 amino acid residues, e.g., in the range of 4–15, more preferably in the range of 4–10 in particular in the range of 4–7 amino acid residues, e.g., of 4, 5, 6, 7, 8 or 10 amino acid residues, where 6 amino acid residues are preferred. Preferably, Z contains at least one Lys residue. In a preferred embodiment of the invention each of the amino acid residues in the peptide sequence Z are independently selected from the group consisting of Ala, Leu, Ser, Thr, Tyr, Asn, Gln, Asp, Glu, Lys, Arg, His, Met, Orn, diaminobutanoic acid and diaminopropanoic acid. Preferably, the amino acid residues are selected from Glu, Lys, and Met, especially Lys, or the amino acid resides are selected from the group consisting of Asn, Glu and Lys. The above-mentioned amino acids may have either D- or L-configuration, but preferably the above-mentioned amino acids have an L-configuration. In a preferred embodiment of the invention Z contains at least 1 lysine residue or when Z is attached via a peptide bond to the N-terminal of said peptide X then Z has an amino acid sequence selected from the group consisting of As-(Glu)n wherein n is an integer from 3 to 7.

Thus, illustrative examples of the peptide sequence Z are: Lys-Lys-Lys-Lys (SEQ ID NO:1), Xaa-Lys-Lys-Lys, Lys-Xaa-Lys-Lys, Lys-Lys-Xaa-Lys, Lys-Lys-Lys-Xaa, Xaa-Xaa-Lys-Lys, Xaa-Lys-Xaa-Lys, Xaa-Lys-Lys-Xaa, Lys-Xaa-Xaa-Lys, Lys-Xaa-Lys-Xaa, Lys-Lys-Xaa-Xaa, Xaa-Xaa-Xaa-Lys, Xaa-Xaa-Lys-Xaa, Xaa-Lys-Xaa-Xaa, Lys-Xaa-Xaa-Xaa, Xaa-Xaa-Xaa-Xaa (SEQ ID NO:2), Lys-Lys-Lys-Lys-Lys (SEQ ID NO:3), Xaa-Lys-Lys-Lys-Lys (SEQ ID NO:4), Lys-Xaa-Lys-Lys-Lys (SEQ ID NO:5), Lys-Lys-Xaa-Lys-Lys (SEQ ID NO:6), Lys-Lys-Lys-Xaa-Lys (SEQ ID NO:7), Lys-Lys-Lys-Lys-Xaa, Xaa-Xaa-Lys-Lys-Lys, Xaa-Lys-Xaa-Lys-Lys, Xaa-Lys-Lys-Xaa-Lys, Xaa-Lys-Lys-Lys-Xaa, Lys-Xaa-Xaa-Lys-Lys, Lys-Xaa-Lys-Xaa-Lys, Lys-Lys-Xaa-Xaa-Lys, Lys-Xaa-Lys-Lys-Xaa, Lys-Lys-Xaa-Lys-Xaa, Lys-Lys-Lys-Xaa-Xaa, Lys-Lys-Xaa-Xaa-Xaa, Lys-Xaa-Xaa-Xaa-Xaa, Lys-Xaa-Lys-Xaa-Xaa, Lys-Xaa-Xaa-Lys-Xaa, Xaa-Xaa-Lys-Xaa, Lys-Xaa-Xaa-Xaa-Lys, Xaa-Lys-Xaa-Xaa, Xaa-Xaa-Lys-Xaa-Xaa, Xaa-Xaa-Lys-Xaa-Lys, Xaa-Lys-Xaa-Xaa-Xaa, Xaa-Xaa-Xaa-Lys-Xaa, Xaa-Xaa-Xaa-Xaa-Lys, Xaa-Xaa-Lys-Xaa-Xaa, Xaa-Xaa-Lys-Lys-Lys, Xaa-Xaa-Xaa-Lys-Lys, Lys-Xaa-Xaa-Xaa-Xaa, Xaa-Xaa-Lys-Xaa-Xaa, Xaa-Lys-Xaa-Xaa-Xaa, Xaa-Lys-Xaa-Xaa, Xaa-Xaa-Lys-Xaa-Xaa, Xaa, Xaa-Xaa-Lys-Xaa, Xaa-Xaa-Xaa-Xaa-Lys, Xaa-Xaa-Xaa-Xaa-Xaa (SEQ ID NO8), Lys-Lys-Lys-Lys-Lys-Lys (SEQ ID NO:9), Xaa-Lys-Lys-Lys-Lys-Lys (SEQ ID NO:10), Lys-Xaa-Lys-Lys-Lys-Lys (SEQ ID NO:11), Lys-Lys-Xaa-Lys-Lys-Lys (SEQ ID NO:12), Lys-Lys-Lys-Xaa-Lys-Lys (SEQ ID NO:13), Lys-Lys-Lys-Lys-Xaa-Lys (SEQ ID NO:14), Lys-Lys-Lys-Lys-Lys-Xaa (SEQ ID NO:15), Xaa-Xaa-Lys-Lys-Lys-Lys (SEQ ID NO:16), Xaa-Lys-Xaa-Lys-Lys-Lys (SEQ ID NO:17), Xaa-Lys-Lys-Xaa-Lys-Lys (SEQ ID NO:18), Xaa, Lys-Lys-Lys-Xaa-Lys (SEQ ID NO:19), Xaa-Lys-Lys-Lys-Lys-Xaa (SEQ ID NO:20), Lys-Xaa-Xaa-Lys-Lys-Lys (SEQ ID NO:21), Lys-Xaa-Lys-Xaa-Lys-Lys (SEQ ID NO:22), Lys-Xaa-Lys-Lys-Xaa-Lys (SEQ ID NO:23), Lys-Xaa-Lys-Lys-Lys-Xaa (SEQ ID NO:24), Lys-Lys-Xaa-Xaa-Lys-Lys (SEQ ID NO:25), Lys-Lys-Xaa-Lys-Xaa-Lys (SEQ ID NO:26), Lys-Lys-Xaa-Lys-Lys-Xaa (SEQ ID NO:27), Lys-Lys-Lys-Xaa-Xaa-Lys (SEQ ID NO:28), Lys-Lys-Lys-Xaa-Lys-Xaa (SEQ ID NO:29), Lys-Lys-Lys-Xaa-Xaa, Xaa-Xaa-Xaa-Lys-Lys-Lys, Xaa-Xaa-Lys-Xaa-Lys-Lys, Xaa-Xaa-Lys-Lys-Xaa-Lys, Xaa-Xaa-Lys-Lys-Lys-Xaa, Xaa-Xaa-Lys-Lys-Xaa, Xaa-Lys-Xaa-Xaa-Lys-Lys, Xaa-Lys-Xaa-Lys-Xaa-Lys, Xaa-Lys-Xaa-Lys-Lys-Xaa, Xaa-Lys-Lys-Xaa-Xaa-Lys, Xaa-Lys-Lys-Xaa-Lys-Xaa, Xaa-Lys-Lys-Lys-Xaa-Xaa, Lys-Xaa-Xaa-Xaa-Lys-Lys, Lys-Xaa-Xaa-Lys-Xaa-Lys, Lys-Xaa-Xaa-Lys-Lys-Xaa, Lys-Xaa-Lys-Xaa-Xaa-Lys, Lys-Xaa-Lys-Xaa-Lys-Xaa, Lys-Lys-Xaa-Xaa-Xaa-Lys, Lys-Xaa-Lys-Lys-Xaa-Xaa, Lys-Xaa-Lys-Xaa-Lys-Xaa, Lys-Xaa-Lys-Xaa-Xaa-Lys Lys-Xaa-Xaa-Lys-Lys-Xaa, Lys-Xaa-Xaa-Lys-Xaa-Lys, Lys-Xaa-Xaa-Xaa-Lys-Lys, Lys-Lys-Xaa-Xaa-Xaa-Xaa, Lys-Xaa-Lys-Xaa-Xaa-Xaa, Lys-Xaa-Xaa-Lys-Xaa-Xaa- Lys, Lys-Xaa-Xaa-Xaa-Lys-Xaa-Lys, Lys-Xaa-Xaa-Xaa-Xaa-Lys-Lys, Xaa-Lys-Lys-Xaa-Xaa-Xaa, Xaa-Lys-Xaa-Lys-Xaa-Xaa, Xaa-Lys-Xaa-Xaa-Lys-Xaa, Xaa-Lys-Xaa-Xaa-Xaa-Lys, Xaa-Xaa-Lys-Lys-Xaa-Xaa, Xaa-Xaa-Lys-Xaa-Lys-Xaa, Xaa-Xaa-Lys-Xaa-Xaa-Lys, Xaa-Xaa-Xaa-Lys-Lys-Xaa, Xaa-Xaa-Xaa-Lys-Xaa-Lys, Xaa-Xaa-Xaa-Xaa-Lys-Lys, Lys-Xaa-Xaa-Xaa-Xaa-Xaa, Xaa-Lys-Xaa-Xaa-Xaa-Xaa, Xaa-Xaa-Lys-Xaa-Xaa-Xaa, Xaa-Xaa-Xaa-Xaa-Lys-Xaa, Xaa-Xaa-Xaa-Xaa-Xaa-Lys, Xaa-Xaa-Xaa-Xaa-Xaa-Xaa, Lys-Lys-Lys-Lys-Lys-Lys-Lys (SEQ ID NO:30), Xaa-Lys-Lys-Lys-Lys-Lys-Lys (SEQ ID NO:31), Lys-Xaa-Lys-Lys-Lys-Lys-Lys (SEQ ID NO:32), Lys-Lys-Xaa-Lys-Lys-Lys-Lys (SEQ ID NO:33), Lys-Lys-Lys-Xaa-Lys-Lys-Lys (SEQ ID NO:34), Lys-Lys-Lys-Lys-Xaa-Lys-Lys (SEQ ID NO:35), Lys-Lys-Lys-Lys-Lys-Xaa-Lys (SEQ ID NO:36), Lys-Lys-Lys-Lys-Lys-Lys-Xaa (SEQ ID NO:37), Xaa-Xaa-Lys-Lys-Lys-Lys-Lys (SEQ ID NO:38), Xaa-Lys-Xaa-Lys-Lys-Lys-Lys (SEQ ID NO:39), Xaa-Lys-Lys-Xaa-Lys-Lys-Lys (SEQ ID NO:40), Xaa-Lys-Lys-Lys-Xaa-Lys-Lys (SEQ ID NO:41), Xaa-Lys-Lys-Lys-Lys-Xaa-Lys (SEQ ID NO:42), Lys-Xaa-Xaa-Lys-Lys-Lys-Lys (SEQ ID NO:43), Lys-Xaa-Lys-Xaa-Lys-Lys-Lys (SEQ ID NO:44), Lys-Xaa-Lys-Lys-Xaa-Lys-Lys (SEQ ID NO:45); Lys-Xaa-Lys-Lys-Xaa-Lys-Lys (SEQ ID NO:46), Lys-Lys-Xaa-Xaa-Lys-Lys-Lys (SEQ ID NO:47), Lys-Lys-Xaa-Lys-Xaa-Lys-Lys (SEQ ID NO:48), Lys-Lys-Xaa-Lys-Lys-Xaa-Lys (SEQ ID NO:49), Lys-Lys-Lys-Xaa-Xaa-Lys-Lys (SEQ ID NO:50), Lys-Lys-Lys-Xaa-Lys-Xaa-Lys (SEQ ID NO:51), Lys-Lys-Lys-Lys-Xaa-Xaa-Lys (SEQ ID NO:52), Xaa-Xaa-Xaa-Lys-Lys-Lys-Lys (SEQ ID NO:53), Xaa-Xaa-Lys-Xaa-Lys-Lys-Lys (SEQ ID NO:54), Xaa-Xaa-Lys-Lys-Xaa-Lys-Lys (SEQ ID NO:55), Xaa-Xaa-Lys-Lys-Lys-Xaa-Lys (SEQ ID NO56), Xaa-Lys-Xaa-Xaa-Lys-Lys-Lys (SEQ ID NO:57), Xaa-Lys-Xaa-Lys-Xaa-Lys-Lys (SEQ ID NO:58), Xaa-Lys-Xaa-Lys-Lys-Xaa-Lys (SEQ ID NO:59), Xaa-Lys-Lys-Xaa-Xaa-Lys-Lys (SEQ ID NO:60), Xaa-Lys-Lys-Xaa-Lys-Xaa-Lys (SEQ ID NO:61), Xaa-Lys-Lys-Lys-Xaa-Lys-Xaa (SEQ ID NO:62), Xaa-Lys-Lys-Xaa-Lys-Xaa-Xaa (SEQ ID NO:63), Xaa-Lys-Lys-Lys-Xaa-Lys-Xaa (SEQ (D NO:64), Xaa-Lys-Lys-Lys-Xaa-Xaa-Lys (SEQ ID NO:65), Lys-Xaa-Lys-Lys-Lys-Xaa-Xaa (SEQ ID NO:66), Xaa-Lys-Lys-Lys-Xaa-Xaa-Xaa (SEQ ID NO:67), Xaa-Lys-Lys-Lys-Xaa-Xaa-Xaa (SEQ ID NO:68), Xaa-Lys-Lys-Lys-Xaa-Xaa-Lys (SEQ ID NO:69), Lys-Lys-Lys-Lys-Xaa-Xaa-Xaa (SEQ ID NO:70), Lys-Lys-Lys-Xaa-Xaa-Lys-Xaa (SEQ ID NO:71), Lys-Lys-Lys-Xaa-Lys-Xaa-Xaa (SEQ ID NO:72), Lys-Xaa-Lys-Xaa-Xaa-Lys-Xaa (SEQ ID NO:73), Lys-Xaa-Lys-Xaa-Xaa-Lys-Lys (SEQ ID NO:74), Lys-Xaa-Xaa-Xaa-Lys-Lys-Lys (SEQ ID NO:75), Lys-Lys-Lys-Xaa-Xaa-Lys-Xaa (SEQ ID NO:76), Lys-Xaa-Lys-Xaa-Xaa-Lys-Lys (SEQ ID NO:77), Lys-Xaa-Xaa-Lys-Lys-Xaa-Lys (SEQ ID NO:78), Lys-Xaa-Xaa-Xaa-Lys-Lys-Lys (SEQ ID NO:79), Lys-Xaa-Xaa-Lys-Lys-Lys-Lys (SEQ ID NO:80), Lys-Xaa-Xaa-Xaa-Lys-Lys-Lys (SEQ ID NO:81), Lys-Xaa-Xaa-Xaa-Lys-Lys-Lys (SEQ ID NO:82), Lys-Lys-Xaa-Xaa-Xaa-Xaa-Lys, Lys-Xaa-Lys-Xaa-Xaa-Xaa-Lys, Lys-Xaa-Xaa-Lys-Xaa-Xaa-Lys, Lys-Xaa-Xaa-Xaa-Lys-Xaa-Lys, Lys-Xaa-Xaa-Xaa-Xaa-Xaa-Lys, Xaa-Lys-Lys-Xaa-Xaa-Xaa-Lys, Xaa-Lys-Xaa-Lys-Xaa-Xaa-Lys, Xaa-Xaa-Lys Xaa-Lys-Xaa-Xaa-Lys-Xaa-Lys, Xaa-Lys-Xaa-Xaa-Xaa-Lys-Lys, Xaa-Xaa-Lys-Lys-Xaa-Xaa-Lys, Xaa-Xaa-Lys-Xaa-Lys-Xaa-Lys, Xaa-Xaa-Lys-Xaa-Xaa-Lys-Lys, Xaa-Xaa-Xaa-Lys,Lys-Xaa-Lys Xaa-Xaa-Xaa-Lys-Xaa-Lys-Lys, Xaa-Xaa-Xaa-Xaa-Lys-Lys-Lys, Lys-Xaa-Xaa-Xaa-Xaa-Xaa-Lys, Xaa-Lys-Xaa-Xaa-Xaa-Xaa-Lys, Xaa-Lys-Xaa-Xaa-Xaa-Xaa Lys Xaa-Xaa-Lys-Xaa-Xaa-Lys, Xaa-Xaa-Xaa-Xaa-Lys-Xaa-Lys, Xaa-Xaa-Xaa-Xaa-Xaa-Lys-Lys, Lys-Xaa-Xaa-Xaa-Xaa-Xaa, Xaa-Xaa-Xaa-Xaa-Lys-Xaa, Xaa-Lys-Xaa-Xaa-Xaa-Xaa-Xaa, Xaa-Xaa-Lys-Xaa-Xaa-Xaa, Xaa-Xaa-Xaa-Xaa-Lys-Xaa, Xaa-Xaa-Xaa-Xaa-Xaa-Xaa-Xaa, wherein each Xaa is independently selected from the group consisting of Ala, Lei, Ser, Thr, Tyr, Asn, Gln, Asp, Glu, Arg, His, Met, Orn, and amino acids of the formula I as defined herein, e.g., Dbu or Dpr.

As indicated above, the amino acid residues of Z may of course all be different or all be identical. However, in interesting embodiments of the present invention, the amino acid residues in Z are selected from two or three different amino acids, or are identical amino acids. Examples of suitable peptide sequences, wherein the amino acid residues in Z are identical are e.g., $(Lys)_n$, wherein n is an integer in the range from 4 to 15, preferably in the range from 4 to 10, such as in the range from 4 to 8, e.g., in the range from about 4 to 7, e.g., $Lys_4$ (SEQ ID NO:1), $Lys_5$ (SEQ ID NO2), $Lys_6$ (SEQ ID NO:8), $Lys_7$ (SEQ ID NO:30). Preferred is $(Lys)_6$ bound via a peptide bond to the C-terminal of X.

Examples of suitable peptide sequences, wherein the amino acid residues in Z are selected from about two different amino acids are e.g., $(Lys-Xaa)_m$ or $(Xaa-Lys)_m$, wherein m is an integer in the range from about 2 to 7, preferably in the range from 2 to 5, such as in the range from 2 to 4, e.g., 3, and Xaa is independently selected from the group consisting of Ser, Thr, Tyr, Asn, Gln, Asp, Glu, Arg, His, Orn, 2,4-diaminobutanoic acid, 2,3-diaminopropanoic acid and Met. More preferably such peptide sequences are e.g., $(Lys-Xaa)_3$ or $(Xaa-Lys)_3$, wherein Xaa is defined above, such as $(Lys-Glu)_3$ (SEQ ID NO:83) or $(Glu-Lys)_3$ (SEQ ID NO:84). Other examples of suitable peptide sequences, wherein the amino acid residues in Z are selected from about two amino acid residues are e.g., $Lys_p$–$Xaa_q$ or $Xaa_p$–$Lys_1$, wherein p and q are integers in the range from 1 to 14, with the proviso that p+q is in the range from 4 to 15, preferably in the range from 4 to 10, such as in the range from 4 to 8, e.g., in the range from 4 to 6, e.g., 4, 5 or 6, and Xaa is independently selected from the group consisting of Ser, Thr, Tyr, Asn, Gln, Asp, Glu, Arg, His and Met. More preferably such peptide sequences are e.g., $Lys_3$-$Xaa_3$ or $Xaa_3$-$Lys_3$, wherein Xaa is as defined above, such as $Lys_3$-$Glu_3$ (SEQ ID No:85) or $Glu_3$-$Lys_3$ (SEQ ID NO:86). More preferred Z sequences consists of a sequence of amino acid residues selected from Asn and Gln together with 4–7 amino acid residues selected from Glu and Asp, such Asn-$(Glu)_5$, Asn-$(Glu)_6$, Gln-$(Glu)_5$, Asn-$(Asp)_5$, and Gin-$(Asp)_5$, which is the N-terminal part of the peptide conjugate of the invention.

Examples of suitable peptide sequences, wherein the amino acid residues in Z are selected from three different amino acids are e.g., $Xaa^1(Lys)_x$-$(Xaa^2)_y$, $Xaa^1$-$(Xaa^2)_x$-$(Lys)_y$, $(Lys)_x$-$(Xaa^2)_y$-$Xaa^1$, $(Xaa^1)_x(Lys)_y$-$Xaa^2$, $(Lys)_x$-$Xaa^1$-$(Xaa^2)_y$, $(Xaa^1)_x$-$Xaa^2$-$(Lys)_y$, $Xaa^1$-Lys-$Xaa^2$ -Lys, Xaa$^1$Lys-Xaa$^2$-Lys-Xaa$^2$, Xaa$^1$Lys-Xaa$^2$-Lys-Xaa$^2$-Lys, Xaa$^1$-Xaa$^2$-Lys-Xaa$^2$, Xaa$^1$-Xaa$^2$-Lys-Xaa$^2$-Lys, Xaa$^1$-Xaa$^1$-Lys-Xaa$^2$-Lys-Xaa$^2$, Lys-Xaa$^2$-Lys-Xaa$^1$-Lys-Xaa$^2$-Lys-Xaa$^2$-Xaa$^1$, Lys-Xaa$^2$-Lys-Xaa$^2$-Lys-Xaa$^1$, Xaa$^2$-Lys-Xaa$^2$-Xaa$^1$, Xaa$^2$-Lys-Xaa$^2$ Lys-Xaa$^1$, Xaa$^2$-Lys-Xaa$^1$-Lys-Xaa$^2$-Xaa$^1$, etc., wherein x and y are integers in the range from about 1 to 5 with the provisor that x+y is at the most 6, and Xaa$^1$ and Xaa$^2$ is independently selected from about the group consisting of Ala, Leu, Ser, Thr, Tyr, Asn, Gln, Asp, Glu, Arg, His, Met, Orn, 2,3-diaminopropanoic acid, 2,4-diaminobutanoic acid and amino acids of the formula I as defined herein.

In preferred embodiments of the invention the ratio between the minimum effective oral dose of said peptide conjugate and the minimum effective dose of the peptide, X is at least 1:5.

A most preferred embodiment of the invention is directed to a novel peptide conjugate comprising a peptide X being an agonist of GLP-1 and/or exendin-4 activity selected from the group consisting of:

des Pro$^{36}$-exendin-4(1–39)-NH$_2$(SEQ ID NO:101),
des pro$^{36}$-exendin-4(1–40)-NH$_2$,
des Pro$^{36}$-des Pro$^{37}$ exendin-4(1–39)-NH$_2$,
des Pro$^{36}$-des Pro$^{37}$-des Pro$^{38}$-exendin-4(1–39)-NH$_2$,
des Pro$^{36}$-des Pro$^{37}$-des Pro$^{38}$-exendin-4(1–40)-NH$_2$,
des Ala$^{35}$-exendin-4(1–39)-NH$_2$ (SEQ ID NO:105),
des Gly$^{34}$-exendin-4(1–39)-NH$_2$ (SEQ ID NO:106),
des Gly$^{34}$-(Lys$^{40}$ (palmitoyl))exendin-4(1–39)-NH$_2$ (SEQ ID NO:108),
des Ala$^{35}$-(Lys$^{40}$ (palmitoyl))exendin-4(1–39)-NH$_2$ (SEQ ID NO:109),
des Pro$^{36}$-(Lys$^{40}$ (palmitoyl))exendin-4(1–39)-NH$_2$ (SEQ ID NO:110),
Compound (iii) Gly$^8$-GLP-1(7–36)-NH$_2$, Gly$^8$-GLP-1 (7–37), and
Gly$^8$-GLP-1(7–36)-Lys$^{37}$ (palmitoyl)-NH$_2$, and being C-terminally bound via a peptide bond to a peptide sequence Z selected from the group consisting of (Lys)$_n$ where n is an integer from 4 to 8, preferably n is 6.

It should be understood that the peptide conjugates of the invention might also be in the preferred amide (NH$_2$) or in the free acid (OH) form or in the form of a salt thereof. Exemplary peptide conjugates of the invention are Gly$^8$-GLP-1(7–36)Lys$_6$-NH$_2$ (SEQ ID NO:88),
(Gly$^8$, Lys$^{37}$(palmitoyl)-GLP-1(7–36)(Human)-Lys$_7$-NH$_2$ (SEQ ID NO:89),
des Ser$^{39}$-exendin-4(1–39)-(Lys)$_6$-NH$_2$ (SEQ ID NO:91),
exendin-4(1–39)-Lys$_6$-NH$_2$ (SEQ ID NO:92),
des Pro$^{36}$-exendin-4(1–39)-Lys$_6$-NH$_2$ (SEQ ID NO:93),
des Ala$^{35}$-exendin-4(1–39)-Lys$_6$-NH$_2$ (SEQ ID NO:94),
des Gly$^{34}$-exendin-4(1–39)-Lys$_6$-NH$_2$ (SEQ ID NO:95),
des Ser$^{39}$-(Lys$^{40}$ (palmitoyl))exendin-4(1–39)-Lys$_7$-NH$_2$ (SEQ ID NO:96),
des Gly$^{34}$-(Lys$^{40}$ (palmitoyl))exendin-4(1–39)-Lys$_7$-NH$_2$ (SEQ ID NO:97),
des Ala$^{35}$-(Lys$^{40}$ (palmitoyl))exendin-4(1–39)-Lys$_7$-NH$_2$ (SEQ ID NO:98),
des Pro$^{36}$-(Lys$^{40}$ (palmitoyl))exendin-4(1–39)-Lys$_7$-NH$_2$ (SEQ ID NO:99),
Lys$^{40}$ (palmitoyl)exendin-4(1–39)-Lys$_7$)NH$_2$(SEQ ID NO:100),
des Pro$^{36}$,Pro$^{37}$-exendin-4(1–39)-Lys$_6$-NH$_2$,
Lys$_6$-des Pro$^{36}$, Pro$^{37}$, Pro$^{38}$-exendin-4(1–39)-NH$_2$
Asn(Glu)$_5$-des Pro$^{36}$,Pro$^{37}$, Pro$^{38}$-exendin-4(1–39)-NH$_2$,
Lys$_6$-des Pro$^{36}$, Pro$^{37}$, Pro$^{38}$-exendin-4(1–39)-Lys$_6$-NH$_2$,
Asn(Glu)$_5$-des Pro$^{36}$, Pro$^{37}$, Pro$^{38}$-exendin-4(1–39)-Lys$_6$-NH$_2$,
des Pro$^{36}$, Pro$^{37}$, Pro$^{38}$-exendin-4(1–39)-Lys$_6$-NH$_2$,
Ser$^8$-GLP-1 (7–36)-Lys$_6$-NH$_2$,
Aib$^8$-GLP-1 (7–36)-Lys$_6$-NH$_2$,
Lys$_6$-Gly$^8$-GLP-1 (7–36)-NH$_2$,
Lys$_6$-Gly$^8$-GLP-1 (7–36)-NH$_2$,
(Gly$^8$,Lys$^{26}$(palmitoyl)-GLP-1(7–36)(Human)-Lys$_6$-NH$_2$,
(Gly$^8$, Lys$^{34}$(palmitoyl)-GLP-1(7–36)(Human)-Lys$_6$-NH$_2$,
Gly$^8$-GLP-1 (7–36)-Lys$_8$-NH$_2$,
Gly$^8$-GLP-1 (7–36)-Lys$_{10}$-NH$_2$,
Gly$^8$-GLP-1 (7–37)-Lys$_6$-NH$_2$,
and the free acid thereof and a pharmaceutically acceptable salt thereof Among the Preferred conjugates are
des Pro$^{36}$-exendin-4(1–39)-Lys$_6$-NH$_2$ (SEQ ID NO:93),
Gly$^8$-GLP-1 (7–36)-Lys$_6$-NH$_2$ (SEQ ID NO:88),
des Pro$^{36}$, Pro$^{37}$, Pro$^{38}$-exendin-4(1–39)-Lys$_6$-NH$_2$, and their salts as defined herein.

In a most specific embodiment, the conjugates are selected from the group consisting of Gly$^8$-GLP-1(7–36) (Human)-NH$_2$, Gly$^8$-GLP-1-(7–36)(Human)-Lys$_6$-NH$_2$, Gly$^8$Lys$^{37}$ (palmitoyl) -GLP-1(7–36)(Human)-Lys$_7$-NH$_2$, Gly$^8$Lys$^{34}$(palmitoyl)-GLP-1-(7–36)(Human)-Lys$_6$-NH$_2$, des Ser$^{39}$-exendin-4(1–39)-Lys$_6$-NH$_2$, exendin-4(1–39)-Lys$_6$-NH$_2$, des Pro$^{36}$-exendin-4(1–39)-Lys$_6$-NH$_2$, des Ala$^{36}$-exendin-4(1–39)-Lys$_6$-NH$_2$, des Gly$^{34}$-exendin-4(1–39)-Lys$_6$-NH$_2$, des Ser$^{39}$-(Lys$^{40}$ (palmitoyl))exendin-4(1–39)-Lys$_7$-NH$_2$, des Gly$^{34}$-(Lys$^{40}$ (palmitoyl))exendin-4(1–39-Lys$_7$-NH$_2$, des Ala$^{35}$-(Lys$^{40}$ (palmitoyl))exendin-4(1–39)-Lys$_7$-NH$_2$, des Pro$^{36}$-(Lys$^{40}$ (palmitoyl))exendin-4(1–39)-Lys$_7$-NH$_2$ and Lys$^{40}$ (palmitoyl)exendin-4(1–39)-Lys$_7$-NH$_s$.

The provision of the peptide conjugates of the present invention enables blood glucose lowering peptides, such as GLP-1 and exendin and their active analogues to be administrated orally. The herein preferred terminal peptide fragments Z are chosen so as to induce an alpha-helical structure to the peptide X without significantly affecting the desired activity of X. Said helical structure stabilises the peptide chain, e.g. against degradation, as evidenced by the increased half life of from 2 to 3 times of the conjugated peptide compared to the unconjugated peptide, cf. table 5 below. The peptide sequence Z is the part of the peptide conjugate responsible for introducing of a curtains structure into the molecule so that the minimum effective dose is lowered at least five fold. Preferably the minimum effective dose is lowered at least tenfold, more preferably 25 fold, even more preferably 40 fold, and most preferably 50 fold. Therefore, the present invention also relates to the use of a peptide sequence (Z) as defined above for the preparation of a said peptide conjugates as defined above.

Thus the invention also relates to a novel peptide conjugate comprising a peptide X as defined herein and wherein X reduces the blood glucose level in a mammal where the ratio between the minimum effective oral dose of said peptide conjugate and the minimum effective oral dose of the peptide X is at least 1:5.

Specifically, the invention is directed to a method for stimulating insulin release in a mammal comprising administering an effective insulinotropic amount of the peptide conjugate of the present invention, a method of lowering blood glucose level in a mammal comprising administering an amount of the peptide conjugate of the present invention effective to lower blood glucose level in said mammal, a method of reducing gastric motility in a mammal in an amount of the peptide conjugate of the present invention effective to reduce gastric motility, a method of delaying gastric emptying in a mammal in an amount of the peptide conjugate of the present invention effective to delay gastric emptying, a method of inhibiting food uptake in a mammal in an amount of the peptide conjugate of the present invention effective to inhibit food uptake and a method of lowering plasma lipid level in a mammal comprising administering an amount of peptide conjugate of the present invention effective to lower plasma lipid level in said mammal. Specifically, the peptide conjugate of the present invention may be used in treatment of diabetes type 1 or type 2, obesity, eating disorders, hyperglycemia, metabolic disorders, gastric disease and insulin resistance syndrome.

The present invention also relates to methods for the preparation of said peptide conjugate, by means of recombinant DNA technology comprising the steps of (a) introducing a nucleic acid sequence encoding said conjugate into a host cell and (b) culturing said host cell and (c) isolating said conjugate from the culture or (a) culturing a recombinant host cell comprising a nucleic acid sequence encoding said conjugate under conditions permitting the production of said conjugate and (b) isolating said conjugate from the culture.

The method also relates to methods for the preparation of said peptide conjugate in which peptide X is obtained via recombinant DNA methods by isolating said peptide. X is then conjugated to Z which is attached to a solid support or has been prepared by solid phase synthetic methods. Furthermore, the invention relates to the preparation of the peptide conjugate of the present invention by peptide synthetic methods. Furthermore, the invention relates to the preparation of the peptide conjugate of the present invention by peptide synthetic methods.

The conjugates of the invention comprising an N-terminal sequence of from 33 to 39, preferably from 36 to 38, amino acid residues having a substantial homology to the native exendin-4 N-terminal sequence thought to be essential for receptor binding (insulinotropic activity) and a C-terminal sequence Z posses as a further advantage improved stability compared to native exendins and C-terminally truncated forms of exendin. Likewise, the GLP-1 peptide conjugate Compound 4 shows improved stability compared to the unconjugated Compound (iii).

Compositions

The invention also concerns a composition comprising the exendin variant or the peptide conjugate of the present invention in combination with a physiologically acceptable carrier. Such compositions may be in a form adapted to oral, parenteral (including subcutaneous (s.c.), intravenous (i.v.), intramuscular (i.m.), epidural, direct brain and intraperitoneal (i.p.)), rectal, intratracheal, intranasal, dermal, vaginal, buccal, ocularly, or pulmonary administration, preferably in a form adapted to subcutaneous or oral administration, and such compositions may be prepared in a manner well-known to the person skilled in the art, e.g., as generally described in "Remington's Pharmaceutical Sciences", 17. Ed. Alfonso R. Gennaro (Ed.), Mark Publishing Company, Easton, Pa., U.S.A., 1985 and more recent editions and in the monographs in the "Drugs and the Pharmaceutical Sciences" series, Marcel Dekker. The compositions may appear in conventional forms, for example, capsules, tablets, aerosols, topical application forms, liquid or semiliquid forms, such as solutions, suspensions, dispersions, emulsions, micelles or liposomes. Preferred are liquid compositions suitable for s.c., administration. In a preferred embodiment, the compositions of the present invention are administered subcutaneously. In an alternative preferred embodiment, the compositions of the present invention are administered orally, and in such cases one preferred administration form is a tablet or capsule.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium sterate, stearic acid or lower alkyl ethers of cellulose. Examples of liquid carriers are syrup, peanut oil, olive oil, phospholipids, sterols, fatty acids, fatty acid amines, polyoxyethylene, isotonic buffer solutions and water. Similarly, the carrier or diluent may include any sustained release material known in the art, such as glyceryl monosterate or glyceryl disterate, alone or mixed with a wax. If a solid carrier is used for oral administration, the preparation may be tabletted, placed in a hard gelatin capsule in power or pellet form or it can be in the form of a troche or lozenge. The amount of solid carrier will vary widely but will usually be from about 25 mg to about 1 g.

A typical tablet which may be prepared by conventional tabletting techniques may contain:

Core: active compound (as free compound of the invention or salt thereof) 100 mg; colloidal silicon dioxide (Aerosil) 1.5 mg; cellulose, microcryst. (Avicel) 70 mg; modified cellulose gum (Ac-Di-Sol) 7.5 mg: magnesium sterate.

Coating: HPMC aprox. 9 mg; *Mywacett 9–40 T approx. 0.9 mg; *acylated monoglyceride used as plasticizer for film coating.

If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of the present invention, preferably a conjugate, dissolved or suspended in a liquid carrier, in particular, an aqueous carrier, for aerosol application. The carrier may contain additives such as solubilizing agents, e.g., propylene glycol, surfactants such as bile acid salts or polyoxyethylene higher alcohol ethers, absorption enhancers such as lecithin (phosphatidylchlorine) or cyclodextrin, or preservatives such as parabines.

The composition may also be in a form suited for local or systemic injection or infusion and may, as such, be formulated with sterile water or an isotonic saline or glucose solution. The compositions may be sterilized by conventional sterilization techniques which are well known in the art. The resulting aqueous solutions may be packaged for use or filtered under aseptic conditions and lyophilized, the lyophilized preparation being combined with the sterile aqueous solution prior to administration. Preferably, the formulation to be used for intravenous, subcutaneous and oral dosing will be a solution of the active compound in buffer. The preparation may be produced immediately before use from active drug substance and sterile buffer solution. One preferred method of sterilization may be sterile filtration of a solution made immediately prior to use. The composition may contain pharmaceutically acceptable auxiliary substances as required to approximate physiological conditions, such as buffering agents, tonicity adjusting agents and the like, for instance sodium acetate, sodium lactate, sodium chloride, potassium chloride, calcium chloride, etc.

The compounds of the invention possess valuable pharmacological properties, e.g. stability towards proteolytic enzymes. In vitro stability studies with the present peptides and peptide conjugates in the presence of selected proteolytic enzymes show increased half lives of the novel peptides compared to prior art peptides. Thus, the compounds of the invention exhibit considerably extended duration of action in vivo compared to GLP-1 and other Glp-1 agonist. Furthermore, the compounds of the invention stimulate cAMP formation. This effect may be demonstrated in a cAMP assay, e.g. as described in WO 98/08871.

The peptide compounds of the present invention are agonists of GLP-1 activity and/or exendin-4 activity and improves blood glucose tolerance in diabetic mammals as determined by assays known in the art for a particular peptide. Examples of such an assay are described herein. Thus, the invention also concerns the exendin variants and peptide conjugates as defined above for use in therapy, and the use of the peptide conjugates as defined above for the manufacture of a pharmaceutical composition for use in therapy, e.g., in the treatment of diabetes type 1 or type 2, obesity, eating disorders and insulin resistance syndrome.

In specific embodiments, the exendin variants and peptide conjugates of the invention may be used to stimulate insulin release, lower blood glucose level, reduce gastric motility, delay gastric emptying, inhibit food uptake, e.g. by suppression of appetite, or lower the plasma lipid level in a vertebrate or a mammal. The novel compounds of the invention may also be used generally in the treatment of diabetes mellitus associated with a risk for hypoglycemia, i.e. where insulin sensitivity is decreased with stress, myocardia infection, stroke and infections, or in cases of insulin resistance during pregnancy. The novel compounds may also be used in the treatment of other types of diabetes, such as cases where diabetes may be secondary to other endocrine diseases such as acromegaly, Cushing's syndrome, pheochromocytoma, glucagonoma, somatostatinoma, primary aldosteronism, or secondary to administration of certain hormones causing hyperglycemia, or secondary to certain drugs (antihypertensive drugs, thiazide diuretics, preparations containing estrogen, psychoactive drugs, sympathomimetric agents. Furthermore, the novel compounds of the invention may be used generally in the treatment of diseases and conditions associated with a risk for hypoglycemia, i.e. where endogenous glucose production is decreased, as following alcohol ingestion, or in cases where the sensitivity to insulin is increased in patients with hypopituitarism or primary adrenocortical insufficiency, or where insulin clearance is devreased as with progressive renal insufficiency. Other specific therapeutic uses are described in WO 99/40788 (relating to the inotropic and diuretic effects of exendin and GLP-1) WO 98/39022 (relating to a method of sedating a mammalian subject having increased activation of the central or peripheral nervous system comprising administering exendin or GLP-1 or an agonist of exendin or GLP-1 to the subject to produce a sedative or anxiolytic effect on the subject), WO 93/18786 (relating to the treatment of diabetes using GLP-1(7-37) or GLP-1(7-36)amide in a regimen which additionally comprises treatment with an oral hypoglycaemic agent, such as sulfonylurea, producing a strong synergistic effect), WO 98/19698 (relating to the use of GLP-1 analogs for the regulation of obesity), WO 98/08531 (relating to the use of GLP-1 or analogs in a method of reducing mortality and morbidity after myocardial infarction), WO 98/08873 (relating to the use of GLP-1 or analogs in a method of attenuating post-surgical catabolic changes and hormonal responses to stress). Besides, the compounds of the invention are suitable in a combination therapy with other antidiabetic agents, such as insulin, metformin, sulfonyl urease and thiazolindinediones, or in combination therapy with other antiobesity agents, such as leptin, dexphenfluramine, amphetamin etc..

Definitions

A "peptide" as used herein is any compound produced by amide formation between a carboxyl group of one amino acid and an amino group of another. The amide bonds in peptides may be called peptide bonds. The word peptide usually applies to compounds whose amide bonds are formed between C-1 of one amino acid and N-2 of another (sometimes called eupeptide bonds), but it includes compounds with residues linked by other amide bonds (sometimes called isopeptide bonds). Peptides with fewer than about 10–20 residues may also be called oligopeptides; those with more, polypeptides. Polypeptides of specific sequence of more than about 50 residues are usually known as proteins. A "natural polypeptide sequence"as used herein refers t a polypeptide sequence consisting of natural L-amino acid residues and which is capable of being expressed by a recombinant host cell. The X compounds herein are all peptide sequences of 40 amino acid residues or less.

"GLP-1" as used herein includes GLP-1(7-37)-OH, GLP-1(7-37)-$NH_2$, GLP-1(7-36)-OH, and GLP-1(7-36)-$NH_2$.

"Agonist" refers to an endogenous substance or a drug that can interact with a receptor and initiate a physiological or a pharmacological response characteristic of that receptor (contraction, relaxation, secretion, enzyme activation, etc.).

"Antagonist" refers to a drug or a compound that opposes the physiological effects of another. At the receptor level, it is a chemical entity that opposes the receptor-associated responses normally induced by another bioactive agent.

"Partial agonist" refers to an agonist which is unable to induce maximal activation of a receptor population, regardless of the amount of drug applied. A "partial agonist" may be termed "agonist with intermediate intrinsic efficacy" in a given tissue. Moreover, a partial agonist may antagonize the effect of a full agonist that acts on the same receptor.

"Receptor" refers to a molecule or a polymeric structure in or on a cell that specifically recognizes and binds a compound acting as a molecular messenger (neurotransmitter, hormone, lymphokine, lectin, drug, etc.).

By "exendin variant" of the present invention is to be understood a variant of a parent exendin peptide having at least about 90% homology to exendin-4 and most preferably having at least about 95% homology to exendin-4(1-39), which has exendin activity, e.g., lowers the blood glucose level in a mammal and binds to a GLP-1 receptor. "Exendin-4" as used herein refers to exendin-4(1-39) the amino acid sequence of which is disclosed in U.S. Pat. No. 5,424,286, SEQ ID NO:1, and exendin-4(1-40) as disclosed by Chen & Drucker in The Journal of Biological Chemistry, Vol. 272, No. 7, pp. 4108–15 which differs only in having glycine in position 40 as C-terminal amino acid residue. The homology of the parent exendin is determined as the degree of identity between two protein sequences indicating a derivation of the first sequence form the second. The homology may suitably be determined by means of computer programs known in the are such as GAP provided in the GCG program package (Program Manual for the Wisconsin Package, Version 8, Aug. 1994, Genetics Computer Group, 575 Science Drive, Madison, Wis., USA 53711) (Needleman, S. B. and Wunsch, C. D., (1970), J. Mol. Biol. 48:443–453). The following settings for polypeptide sequence comparison may be used: GAP creation penalty of 3.0 and GAP extension penalty of 0.1.

"Salts" includes pharmaceutically acceptable salts, such as acid addition salts and basic salts. Examples of acid addition salts are hydrochloride salts, sodium slats, hydrobromide slats, etc. Examples of basic salts are salts where the cation is selected from alkali metals, such as sodium and potassium, alkaline earth metals, such as calcium, and ammonium ions +$N(R^3)_3(R^4)$, and $R^3$ and $R^4$ independently designates optionally substituted $C_{1-6}$-alkyl, optionally substituted $C_{2-6}$-alkyenyl, optionally substituted aryl, or optionally substituted heteroaryl. Other examples of pharmaceutically acceptable salts are; e.g., those described in "Reminton's Pharmaceutical Sciences" 17. Ed, Alfonso R. Gennaro (Ed.), Mark Publishing Company, Easton, Pa., U.S.A., 1985 and more recent editions, and in Encyclopedia of Pharmaceutical Technology.

Preparation of Variants and Conjugates

The exendin variants and the peptide conjugates of the invention may be prepared by methods known per se in the art. Thus, the variants and the peptides sequences X and Z may be prepared by standard peptide-preparation techniques such as solution synthesis or Merrifield-type solid phase synthesis. It is believed that the Bod (tert.butyloxycarbonyl) as well as the Fmoc (9-fluorenylemthyloxycarbonyl) strategies are applicable.

In one possible synthesis strategy, the peptide conjugates of the invention may be prepared by solid phase synthesis by first constructing the peptide sequence Z using well-known standard protection, coupling and deprotection procedures, thereafter sequentially coupling the peptide sequence X on Z in a manner similar to the construction of Z, and finally cleaving off the entire peptide conjugate from the carrier. This strategy yields a peptide conjugate, wherein the peptide sequence Z is covalently bound to the peptide X at the C-terminal carbonyl function of X. IF the desired peptide conjugate, however, is a peptide conjugate, wherein two stabilising sequences Z are covalently and independently bound to both the C- and the N- terminal of the peptide X, the above strategy is also applicable but, as will be understood by the person skilled in the art, before cleaving the off the C-terminal bound peptide conjugate from the solid support, it is necessary to sequentially couple the second peptide sequence Z to the N-terminal of X in a manner similar to the procedure described above. This strategy may also be used to attache Z to the carbonyl function on the side chain of Giu or Asp. A possible strategy for the preparation of peptide conjugates, wherein the peptide sequence Zis covalently bound to the N-terminal nitrogen atom or covalently bound to the nitrogen atom on the side chain of Lys, Arg or His of X is analogous with the method described above, i.e, said peptide conjugates may be prepared by solid phase synthesis by first constructing the peptide sequence X using well-known standard protection, coupling and deprotection procedures, thereafter sequentially coupling the peptide sequence Z on X in a manner similar to the construction of X, and finally cleaving off the entire peptide conjugate from the carrier. Another possible strategy is to prepare one or both of the two sequences X and Z (or parts thereof) separately by solution synthesis, solid phase synthesis, recombinant techniques, or enzymatic synthesis, followed by coupling of the two sequences by well-known segment condensation procedures, either in solution or using solid phase techniques or a combination thereof. In one embodiment, X may be prepared by recombinant DNA methods and Z may be prepared by solid phase synthesis. The conjugation of X and Z may be carried out by using chemical ligation. This technique allows for the assembling of totally unprotected peptide segments in a highly specific manner (Liu et al., 1996, J. Am. Chem. Soc. 118:307–312 and Dawson et al., 1996, 226:776). The conjugate can also be performed by protease-catalysed peptide bond formation, which offers a highly specific technique to combine totally unprotected peptide segments via a peptide bond (W. Kullmann, 1987, Enzymatic Peptide Synthesis, CRC Press, Boca Raton, Fla., pp. 41–59).

Side chain derivatization of Lys, Arg, His, Trp, Ser, Thr, Cys, Tyr, Asp and Glu with the peptide sequence, Z, can be carried out by traditional convergent peptide synthesis using suitable orthogonal protecting schemes as known in the art, or by using the equally well known general solid phase method with suitable orthogonal removable chain protection.

Furthermore, it is envisaged that a combination of the above-mentioned strategies may be especially applicable where a modified peptide sequence, e.g., from a peptide X comprising isomeric bonds such as reduced peptide bonds, is to be coupled to a peptide sequence Z. In this case, it may be advantageous to prepare the immobilized fragment of Z by successive coupling of amino acids, and then couple a complete peptide sequence X (prepared in solution or fully or partially using solid phase techniques or by means of recombinant techniques) to the fragment.

Examples of suitable solid support materials (SSM) are elg., functionalised resins such as polystyrene, polyacrylamide, polydimethylacryalminde, polyethyleneglyucol, cellulose, polyethylene, polyethyleneglycol grafted on polystyrene, latex, dynabeads, etc. It should be understood that it may be necessary or desirable that the C-terminal amino acid of the peptide sequence Z or the C-terminal amino acid of the peptide X is attached to the solid support material by means of a common linker such as 2,4-dimethoyx-4'-hydroxy-benzophenone, 4-(4-hydroxy-methyl-3-methoxyphenoxy)-butyric acid, 4-hydroxy-methylbenzoic acid, 4-hydroxymethyl-phenoxyacetic acid, 3-(4-hydroxymethylphenoxy)propionic acid, and p-[(R,S)-a [1-(9H-fluoren-9-yl)methoxyformamido]-2,4-dimethoxybenzyl]-phenoxy-acetic acid.

The variants and the peptide conjugates of the invention may be cleaved from the solid support material by means of an acid such as trifluoracetic acid, trifluoromethanesulfonic acid, hydrogen bromide, hydrogen chloride, hydrogen fluoride, etc. optionally in combination with one or more "scabengers" suitable for the purpose, e.g., ethanedithiol, triisopropylsilane, phenol, thioanisole, etc., or the peptide conjugate of the invention may be cleaved from the solid support by means of a base such as ammonia, hydrazine, an alkoxide, such as sodium ethoxide, an hydroxide, such as sodium hyroxide, etc.

Thus, the present invention also relates to a method for the preparation of a pharmacologically active peptide conjugate, wherein Z is covalently bound to X, preferably via a peptide bond. A method for the preparation of a peptide conjugate of formula I(X-2), comprises the steps of:

a) coupling an amino acid or dipeptide having suitable protecting groups, including an N-α-protecting group, in the activated form to an immobilized peptide sequence H-Z-SSM, thereby forming an immobilized N-α-protected peptide fragment, b) removing said N-α-protecting group, thereby forming an immobilized protected peptide fragment having an unprotected N-terminal, c) coupling an additional amino acid or dipeptide having suitable protecting groups including an N-α-protecting group in the carboxyl activated form to the N-terminal of the immobilized peptide fragment, and repeating the removal/coupling step procedure in step b) and c) until the desired peptide sequence X is obtained, and then d) cleaving off the peptide conjugate from the solid support material.

A method for the preparation of a peptide conjugate of formulate II(Z-X), comprises the steps of:

a) coupling an amino acid or dipeptide having suitable protecting groups, including an N-α-protecting group, in the activated form to a solid support material (SSM), thereby forming an immobilised protected amino acid or a protected dipeptide, b) removing said N-α-protecting group, thereby forming an immobilised amino acid or peptide fragment having an unprotected N-terminal, c) coupling an additional amino acid or dipeptide having suitable protecting groups, including an N-α-protecting group, in the carboxyl activated form to the N-terminal of the immobilised amino acid or peptide fragment, and repeating the removal/coupling step procedure in step b) and c) until the desired peptide sequence X is obtained, d) coupling an additional amino acid or dipeptide having suitable protecting groups, including an N-α-protecting group, in the carboxyl activated form to the N-terminal of the immobilised peptide fragment, and repeating the removal/coupling step procedure in step b) and d) until the desired peptide sequence Z is obtained, and then e) cleaving off the peptide conjugate from the solid support material.

Furthermore, a method for the preparation of a peptide conjugate of formula III(Z-X-Z), comprises the steps of:

a) coupling an amino acid or dipeptide having suitable protecting groups, including an N-α-protecting group, in the carboxyl activated form to an immobilised peptide sequence H-A-SSM, thereby forming an immobilised N-α-protected peptide fragment, b) removing said N-α-protecting group, thereby forming an immobilised peptide fragment having an unprotected N-terminal, c) coupling an additional amino acid or dipeptide having suitable protecting groups, including an N-α-protecting group, in the carboxyl activated form to the N-terminal of the immobilised peptide fragment, and repeating the removal/coupling step procedure in step b) and c) until the desired peptide sequence X is obtained, and then d) coupling an additional amino acid or dipeptide having suitable protecting groups, including an N-α-protecting group, in the carboxyl activated form to the N-terminal of the immobilised peptide fragment, and repeating the removal/coupling step procedure in step b) and d) until the desired peptide sequence Z is obtained, and then e) cleaving off the peptide conjugate from the solid support material.

The coupling, removal and cleavage steps are performed by methods known to the person skilled in the art taking into consideration the protection strategy and the selected solid phase material. In general, however, it is believed that the Boc (tert.butyloxycarbonyl) as well as the Fmoc (9-fluorenylemthyloxycarbonyl) protection strategies are applicable and that peptide bonds may be formed using the various activation procedures known to the person skilled in the art, e.g., by reacting a C-terminal activated derivative (acid halide, acid anhydride, activated ester e.g., HObt-ester, etc.) of the appropriate amino acid or peptide with the amino group of the relevant amino acid or peptide as known to a person skilled in peptide chemistry. Furthermore, it may be necessary or desirable to include side-chain protection groups when using amino acid residues carrying functional groups which are reactive under the prevailing conditions. The necessary protection scheme will be known to the person skilled in the art (cf., e.g., M. Bodanszky and A. Bodanszky, "The Practice of Peptide Synthesis", 2. Ed, Springer-Verlag, 1994, J. Jones, "The Chemical Synthesis of Peptides", Clarendon Press, 1991, and Dryland et al., 1986, J. Chem. Soc., Perkin Trans. 1:125–137).

The peptides and peptide conjugates of the invention may also be prepared by means of recombinant DNA technology using general methods and principles known to the person skilled in the art. A nucleic acid sequence encoding the peptides and peptide conjugates may be prepared synthetically by established standard methods, e.g., the phosphoamidite method described by S. L. Beaucage and M. H. Caruthers, Tetrahedron Letters 22, 1981, pp. 1859–1869, or the method described by Matthes et al., EMBO Journal 3, 1984, pp. 801–805. According to the phosphoamidite method, oligonucleotides are synthesized, e.g., in an automatic DNA synthesizer, purified, annealed, ligated and cloned in suitable vectors. The technique used to isolate or clone a nucleic acid sequence encoding peptide X are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural feature. See, e.g., Innis et al., 1990, A Guide to Methods and Application, Academic Press, N.Y. Other nucleic acid amplification procedures such as ligase chain reaction (LCR), ligated activated transcription (LAT) and nucleic acid sequence-based amplification (NASBA) may be used. It can then be ligated to a nucleic acid sequence encoding Z.

The nucleic acid sequence encoding the peptides and peptide conjugates is then inserted into a recombinant expression vector which may be any vector which may conveniently be subjected to recombinant DNA procedures. The choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid. Alternatively, the vector may be one which, when introduced into a host cell, is integrated into the host cell genome and replicated together with the chromosome(s) into which it has been integrated.

In the vector, the nucleic acid sequence encoding the peptides and peptide conjugates of the present invention should be operably connected to a suitable promoters sequence. The promoter may be any nucletic acid sequence which shows transcriptional activity in the host cell of choice and may be derived from genes encoding said proteins either homologous or heterologous to the host cell. Examples of suitable promoters for directing the transcription of the nucleic acid sequence encoding said peptides and peptide conjugates in mammalian cells are the SV 40 promoter (Subramani et al., Mol. Cell Biol. 1, 1981, pp 854–864), the MT-1 (metallothionein gene) promoter (Palmiter et. al., Science 222, 1983, pp. 809–814) or the adenovirus 2 major late promoter, a Rous sarcoma virus (RVS) promoter, cytomegalovirus (CMV) promoter (Boshart et al., 1981, Cell 41:521–530) and a bovine papilloma virus promoter (BPV). A suitable promoter for use in insect cells is the polyhedrin promoter (Vasuvedan et al., FEBS Lett. 311, 1992, pp. 7–11).

Examples of suitable promoters for directing the transcription of the nucleic acid sequence encoding the peptides and peptide conjugates, especially in a bacterial host cell, are the promoters obtained from the *E. coli* lac operon, the *Streptomyces coelicolor* agarase gene (dagA), The *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha amylase gene (amyQ), the *Bacillus licheniformis* penicillinase gene (penP), the *Bacillus subtilis* xylA and xylB genes, and the procaryotic beta-lactamase gene (Villa-Kamaroff et al., 1978, Proceedings of the National Academy of Sciences USA 75:3727–3731), as well as the tac promoter (DeBoer et al., 1983, Proceedings of the National Academy of Sciences USA 80:21 25). Further promoters are described in "Useful proteins from recombinant bacteria" in Scientific American, 1980, 242:74–94; and in Sambrook et al., 1989, supra. Examples of suitable promoters for directing the transcription of the nucleic acid sequence encoding the peptides and peptide conjugates in a filamentious fungal host cell are promoters obtained form the genes encoding *Aspergillus oryzae* TAKA amylase, *Rhizomucor miehei* aspartic proteinase, *Aspergillus niger* neutral alpha-amulase, *Aspergullus niger* acid stable alpha-amylase, *Aspergillus niger* or *Aspergillus awamori* glucoamylase(glaA), *Rhizomucor miehei* lipase, *Aspergillus oryzae* alkaline protease, *Aspergillus oryzae* triose phosphate isomerase, Aspergillus nidulans acetamidase, *Fusarium oxysporum* trypsin-like protease (as described in U.S. Pat. No. 4,288,627, which is incorporated herein by reference), and hybrids thereof. Particularly preferred promoters for use in filamentous fungal host cells are the TAKA amylase, NA2-tpi (a hybrid of the promoters from the genes encoding *Aspergillus niger* neutral a amylase and *Aspergillus oryzae* triose phosphate isomerase), and glaA promoters. In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, Yeast 8:423–488.

The nucleic acid sequence encoding said peptides and peptide conjugates may also be operably connected to a suitable terminator, such as the human growth hormone terminator (Palmiter et al., op. cit.) Preferred terminators for filamentious fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Preferred terminators for yeast host cells are obtained from the genes encoding *Saccharomyces cerevisiae* enolase, *Saccharomyces cerevisiae* cytochrome C (CYC1), or *Saccharomyces cerevisiae* glyceraldehyde-3-phosphate dehydrogenase. Other useful terminator for yeast host cells are described by Romanos et al., 1992, supra.

The vector may further comprise elements such as polyadenylation signals (e.g., from SV 40 or the adenovirus 5 Elb region), transcriptional enhancer sequences (e.g., the SV 40 enhancer) and translational enhancer sequences (e.g., the ones encoding adenovirus VA RNAs). Furthermore, preferred polyadenylation sequences for filamentous fungal host cells are obtained from the genes encoding *Aspergillus oryzae* TAKA amylase, *Aspergilus niger* glucoamylase, *Aspergilus nidulans* anthranilate synthase, and *Aspergillus niger* alpha-glucosidase. Useful polyadenylation sequences for yeast host cells are described by Guo and Sherman, 1995, Molecular Cellular Biology 15:5983–5990/

The recombinant expression vector may further comprise a DNA sequence enabling the vector to replicate in the host cell in question. Examples of such a sequence (when the host cell is a mammalian cell) is the SV 40 or polyoma origin of replication. Examples of bacterial origins of replication are the originals of replication of plasmids pBR322, pUC19, pACYC177, pACYC184, pUB110, pE194, pTA1060, and pAMB1. Examples of origin of replications for use in a yeast host cell are the 2 micron origin of replication, the combination of CEN6 and ARS4, and the combination of CEN3d and ARS1. The origin of replication may be one having a mutation to make its function temperature-sensitive in the host cell (see, e.g., Ehrlich, 1978, Proc. Natl. Acad. Sci. USA 75:1433).

The vector may also comprise a selectable marker, e.g., a gene the product of which complements a defect in the host cell, such as the gene coding for digydrofolate reducase (DHFR) or one which confers resistance to a drug, e.g., neomycin, geneticin, ampicillin, or hygromycin. Suitable markers for yeast host cells are ADE2, HIS3, LEU2, LYS2, MET3, TRP1, and URA3. A selectable market for use in a filamentous fungal host cell mayb e selected from the group including, but not limited to, amdS (acetamidase), argB (ornithine carbamoyltransferase), bar (phosphinothriein acetyltransferase), hygB (hygromycin phosphotransferase), niaD (nitrate reductase), pyrG (orotidine-5=-phosphate decarboxylase), sC (sulfate adenyltransferase), trpC (anthranilate synthase), and glufosinate resistance markers, as well as equivalens from other species. Preferred for use in an Aspergillus cell are the amdS and pyrG markers of *Aspergillus nidulans* or *Aspergillus oryzae* and the bar marker of *Streptomyces hygroscopicus*. Furthermore, selection may be accomplished by cotransformation, e.g., as described in WO 91/17243, where the selectable marker is on a separate vector.

The procedures used to ligate the nucleic acid sequences coding for the peptides and peptide conjugates, the promoter and the terminator, respectively, and to insert them into suitable vectors containing the information necessary for replication, are well known to persons skilled in the art (cf., for instances, Sambrook et al., op.cit.).

The host cell into which the expression vector is introduced may be any cell which is capable of producing the peptides and peptide conjugates and is may be a eukaryotic cell, such as invertebrate (insect) cells or vertebrate cells, e.g., *Xenopus laevis* oocytes or mammalian cells, in particular insect and mammalian cells. Examples of suitable mammalian cell lines are the COS (e.g., ATCC CRL 1650), BHK (e.g., ATCC CRL 1632, ATCC CCL 10) or CHO (e.g., ATCC CCL 61) cell lines. Methods for transfecting mammalian cells and expressing DNA sequences introduced in the cells are described in e.g., Kaufman and Sharp, 1982, J. Mol. Biol. 159:601–621; Southern and Berg, 1982, J. Mol. Appl. Genet. 1:327–341; Loyter et al., 1982, Proc. Natl. Acad. Sci. USA 79:422–426; Wigler et al., 1978, Cell 14:725; Corsaro and Pearson, 1981, Somatic Cell Genetics 7:603, Graham and van der Eb, 1973, Virology 52:456; Fraley et al., 1980, JBC 225:10431; Capecchi, 1980, Cell 22:479; Wiberg et al., 1983, NAR 11:7287; and Neumann et al., 1982EMBO J.1:841–845. The host cell may also be a unicellular pathogen, e.g., a prokaryote, or a non-unicellular pathogen, e.g., a eukaryote. Useful unicellular cells are bacterial cells such as gram positive bacterial including, but not limited to, a Bacillus cell, e.g, *Bacillus alkalophilus, Bacillus amyloliquefaciens, Bacillus brevis, Bacillus circulans, Bacillus coagulans, Baccillus lautus, Bacillus lentus, Bacillus licheniformis, Bacillus megaterium, Bacillus stearothermophilus, Bacillus subtilis*, and *Bacillus thuringiensis*; or a Streptomyces cell, e.g., *Streptomyces lividans* or *Streptomyces murinus*, or gram negative bacteria such as *E. coli* and Pseudomonas sp. In a preferred embodiment, the bacterial host cell is a *Bacillus lentus, Bacillus licheniformis, Bacillus stearothermophilus* or *Bacillus subtilis* cell. The transformation of a bacterial host cell may, for instance, be effected by protoplast transformation (see, e.g., Chang and Cohen, 1979, Molecular General genetics 168:111–115), by using competent cells (see, e.g., Yound and Spizizin, 1961, Journal of Bacteriology 81:823–829, or Dubnar and Davidoff Abelson, 1971, Journal of Molecular Biology 56:209–221), by electroporation (see, e.g., Shigekawa and Dower, 1988, Biotechniques 6:742–751), or by conjugation (see, e.g., Koehler and Thorne, 1987, Journal of Bacteriology 169:5771–5278). The host cell may be a fungal cell. The fungal host cell may also be a yeast cell. "Yeast" as used herein includes ascosporogenous yeast (Endomycetales), basidiosporogenous yeast, and yeast belonging to the Fungi Imperfecti (Blastomycetes).

The medium used to culture the cells may be any conventional medium suitable for growing mammalian cells, such as a serum-containing or serum-free medium containing appropriate supplements, or a suitable medium for growing insect, yeast or fungal cells. Suitable media are available from commercial suppliers or may be prepared according to published recipes (e.g., in catalogues of the American Type Culture Collection).

Thus, the invention also relates to a method for producing the exendin variants and peptide conjugates of the invention having a natural polypeptide sequence, comprising a) introducing a nucleic acid sequence encoding a polypeptide sequence comprising the peptide sequence of the exendin variant or the peptide conjugate of the invention and a selectable marker contained within a nucleic acid construct or a vector into a host cell to obtain a recombinant host cell;

b) selecting said recombinant host cell;

c) culturing said recombinant host cells under conditions permitting the production of said polypeptide sequence;

d) isolating said polypeptide sequence from the culture; and e) optionally cleaving said polypeptide sequence using an appropriate protease to obtain said peptide conjugate.

The variants and peptide conjugates of the invention having a natural polypeptide sequence thus produced by the cells may then be recovered from the culture medium by conventional procedures including separating the host cells from the medium by centrifugation or filtration, precipitating the proteinaceous components of the supernatant or filtrate by means of a salt, e.g., ammonium sulphate, purification by a variety of chromatographic procedures, e.g., ion exchange chromatography, affinity chromatography, or the like. The lipophilic substitutent(s) may be attached to the peptide of the present invention using procedures known in the art. In one embodiment, the lipophilic substitutent may be attached by incorporating an amino acid with the lipophilic substituent already attached in the standard synthesis method (see, for example, synthesis of compound 7 in the Examples section). Alternatively, the substituent may be attached after the peptide has been synthesized and isolated as, for example, described in WO98/09971.

The invention is further illustrated by the following examples.

EXAMPLES

Peptide Synthesis, General Procedures
Apparatus and synthetic strategy

Peptides are synthesized batchwise in a polyethylene vessel equipped with a polypropylene filter for filtration using 9-fluorenylemthyloxycarbonyl (Fmoc) as the N-α- amino protecting group and suitable common protection groups for side-chain functionalities (Dryland et al., 1986, J. Chem. Soc., Perkin Trans, 1:125–137).
Solvents Solvent DMF (N,N-dimethylformamide, Riedel de-Häen, Germany) is purified by passing it through a column packed with a strong cation exchange resin (Lewatit S 100 MB/H strong acid, Bayer AG Leverkusen, Germany) and analysed for free amines prior to use by addition of 3,4-dihydro-3-hydroxy-4-oxo-1,2,3-benzotriazine (Dhbt-OH) giving rise to a yellow color (Dhbt-O-anion) if free amines are present. Solvent DCM (dichloromethane, analytical grade, Riedel de-Häen, Germany) is used directly without purification. THF (tetrahydrofuran, analytical grade, Riedel de-Haen, Germany) is used directly without further purification.
Amino acids Fmoc-protected amino acids are purchased from MilliGen (UK) and from PerSeptive Biosystems GmbH Hamburg, Germany in suitable side-chain protected forms. FmocLys (palmitoyl)-OH is purchased from Bachem (Switzerland).
Linker (4-hydroxymethylphenoxy)acetic acid (HMPA), Novabiochem, Switzerland is coupled to the resin either as a preformed or in situ generated 1-hydroxybenzotriazole (HObt) ester by means of DIC.
Coupling reagents Coupling reagent diisopropylcarbodiimide (DIC) is purchased from (Riedel de-Häen, Germany) and distilled prior to use, dicyclohexylcarbodiimide (DCC) is purchased from Merck-Schuchardt, München, Germany, and purified by distillation.
Solid supports Peptides synthesized according to the Fmoc-strategy are synthesized on the following types of solid support using 0.05M or higher concentrations of Fmoc-protected activated amino acid in DMF, TentaGel S resins 0.22–0.31 mmol/g (TentaGel S-Ram, TentaGel S RAM-Lys(Boc)Fmoc; Rapp polymere, Germany).
Catalysts and other reagents Diisopropylethylamine (DIEA) is purchased from Aldrich, Germany, and ethylenediamine from Fluka, piperdine and pyridine from Riedel-de Häen, Frankfurt, Germany. 4-(N,N-di-methylamino)pyridine (DMAP) is purchased from Fluka, Switzerland and used as a catalyst in coupling reactions involving symmetrical anhydrides. Ethanedithiol is purchased from Riedel-de Häen, Frankfurt, Germany. 3,4-dihydro-3-hydroxy-4-oxo-1,2,3-benzotriazine (Dhbt-OH) and 1-hydroxybenzotriazole (HObt) are obtained from Fluka, Switzerland.
Coupling procedures The first amino acid is coupled as a symmetrical anhydride in DMF generated from the appropriate N-α-protected amino acid by means of DIC or DCC. The following amino acids are coupled as performed HObt esters made from appropriate N-α-protected amino acids and HObt by means of DIC and DMF. Acylations are checked by the ninhydrin test performed at 80° C. in order to prevent Fmoc deprotection during the test (Larsen, B. D. and Holm, A., 1994, Int. J. Peptide Protein Res. 43:1–9).
Coupling as HObt-ester Method a. 3 eq. N-α-amino protected amino acid is dissolved in DMF together with 3 eq. HObt and 3 eq DIC. The solution is left at r.t. for 10 minutes and then added to the resin, which had been washed with a solution of 0.2% Dhbt-OH in DMF prior to the addition of the preactivated amino acid. Method b. 3 eq. N-α-amino protected amino acid is dissolved in DMF together with 3 eq. HObt 3 eq DIC are added just prior to use. The final solution is added to the resin.

Preformed symmetrical anhydride 6 eq. N-α-amino protected amino acid is dissolved in DCM and cooled to 0° C. DCC or DIC (3 eq.) is added and the reaction continued for 10 min. The solvent is removed in vacuo and the residue dissolved in DMF. The DMF-solution is filtered in case of using DCC and immediately added to the resin followed by 0.1 eq. of DMAP.

Deprotection of the N-α-amino Fmoc protecting group

Deprotection of the Fmoc group is performed by treatment with 20% piperdine in DMF (1×5 and 1×10 min.), followed by wash with DMF until no yellow colour (Dhbt-O-) could be detected after addition of Dhbt-OH to the drained DMF.

Cleavage of peptide from resin with acid

Method a. Peptides are cleaved from the resins by treatment with 95% trifluoroacetic acid (TFA, Riedel-de Häen, Frankfurt, Germany)-water v/v or with 95% TFA and 5% ethanedithiol v/v at r.t. for 2 h. The filtered resins are washed with 95% TFA-water and filtrates and washings are diluted by adding 10% acetic acid. The resulting mixture is extracted 3 times with ether and finally freeze dried. The crude freeze dried product is analysed by high-performance liquid chromatography (HPLC) and identified by mass spectrometry (MS).

Batchwise peptide synthesis on TentaGel S-RAM

TentaGel S-RAM resin (100–1000 mg, 0.22–0.31 mmol/g) is placed in a polyethylene vessel equipped with a polypropylene filter for filtration. The resin is swelled in DMF (5–10 ml), and the Fmoc group is removed according to the procedure described above. The following amino acids according to the sequence are coupled as Fmoc-protected HObt esters (3 eq.) generated in situ by means of DIC as described above. The couplings are continued for 3 h, unless otherwise specified. The resin is drained and washed with DMF (4×5–10 ml, 2 min each) in order to remove excess reagent. All acylations are checked by the ninhydrin test performed at 80° C. After completion of the synthesis, the peptide-resin is washed with DMF (3×5–10 ml,, 5 min each), DCM (3×5–10 ml, 1 min each) and finally diethyl ether (3×5–10 ml, 1 min each) and dried in vacuo.

HPLC conditions

Isocratic HPLC analysis is preformed on a Shimadzu system consisting of an LC-6A pump, an MERCK HITACHI L-4000 UV detector operated at 215 nm and a Rheodyne 7125 injection valve with a 20 μl loop. the column used for isocratic analysis is a Spherisorb ODS-2(100×3 mm; 5-μm particles) (MicroLab, Aarhus, Denmark). HPLC analysis using gradients is performed on a MERCH-HITACHI L-6200 Intelligent pump, an MERCK HITACHI L-4000 UV detector operated at 215 nm and a Rheodyne 7125 injection valve with a 20 μl loop, or on a Waters 600 E instrument equipped with a Waters 996 photodiode array detector. The columns used are a Rescorce™ RPC 1 ml (Waters) or a LiChroCART 125–4, LiChrospher 100 RP-18 (5 μm) (Merck). Buffer A is 0.1 vol % TFA in water and buffer B 90 vol% acetonitrile, 9.9 vol% water and 0.1 vol% TFA. The buffers are pumped through the columns at a flow rate of 1.3–1.5 ml/min using either of the following gradients for peptide analysis 1) Linear gradient from 0 %–100% B (30 min) or 2) 0% B (2 min) linear gradient from 0–50% B (23 min) 50 –100% B (5 min). For Preparative HPLC, purification is performed on a Waters 600 E instrument equipped with a Waters 996 photodiode array detector. The column used is a Waters Delta-Pak C-18 15 μm, 100 Å, 25×100 mm. Gradient "2)" is used with a flow rate of 9 ml/min.

Mass spectroscopy

Mass spectra are obtained on a Finnigan Mat LCQ instrument equipped with an electrospray (ESI) probe (ES-MS) and on a TofSpec E, Fisons Instrument (MALDI-TOF) using β-cyano-p-hydroxycinnamic acid as matrix. Alternatively, spectra may be obtained by a Micromass LCT instrument.

Peptide Synthesis of Prior Art Peptides (i) Peptide synthesis of Compound (i), H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$(exendin-4 (1–39)-NH$_2$)(SEQ ID NO: 102) on TentaGel S-RAM.

Dry TentaGel S-RAM resin (0.25 mmol/g, 1000 mg) is placed in a polyethylene vessel equipped with a polypropylene filter for filtration and swelled for two hours in DMF (5 ml). The Fmoc group is removed according to the procedure described above, and the peptide according to the sequence is assembled as described under "Batchwise peptide synthesis on TentaGel S-RAM resins". After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin according to method a as described above and freeze dried from acetic acid. The crude peptide is purified by preparative HPLC using the procedure described above. The purified product is found to be homogeneous and the purity is found to be better than 90%. The identity of the peptide is confirmed by ES-MS. Yield 17%.

(ii) Peptide synthesis of Compound (ii), H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-NH$_2$(des Ser$^{39}$ exendin-4(1–39)-NH$_2$)f on TentaGel S-RAM.

Dry TentaGel S-RAM resin (0.25 mmol/g, 1000 mg) is placed in a polyethylene vessel equipped with a polypropylene filter for filtration and swelled for two hours in DMF (5 ml). The Fmoc group is removed according to the procedure described above, and the peptide according to the sequence is assembled as described under "Batchwise peptide synthesis on TentaGel S-RAM resins". After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin according to method a as described above and freeze dried from acetic acid. The crude peptide is purified by preparative HPLC using the procedure described above. The purified product is found to be homogeneous and the purity is found to be better than 97%. The identity of the peptide is confirmed by ES-MS. Yield 22%.

(iii) Peptide synthesis of Compound (iii) H-His-Gly-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-NH$_2$(Gly$^8$-GLP1-(7–36) (human_-NH$_2$) (SEQ ID NO: 87) on TentaGel S-RAM.

Dry TentaGel S-RAM resin (0.25 mmol/g, 1000 mg) is placed in a polyethylene vessel equipped with a polypropylene filter for filtration and swelled for two hous in DMF (5 ml). The Fmoc group is removed according to the procedure described above, and the peptide according to the sequence is assembled as described under "Batchwise peptide synthesis on Tenta-Gel S-RAM resins". After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin according to method a as described above and freeze dried from acetic acid. The crude peptide is purified by preparative HPLC using the procedure described above. The purified product is found to be homogeneous and the purity is found to be better than 95%. The identity of the peptide is confirmed by ES-MS. Yield 9%.

Synthesis of Peptide Sequences of the Invention

1. Peptide synthesis of Compound 1, H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-$NH_2$(des $Pro^{36}$-exendin-4 (1–39)-$NH_2$)(SEQ ID NO: 101) on TentaGel S-RAM.

Dry TentaGel S-RAM resin (0.25 mmol/g, 1500 mg) is placed in a polyethylene vessel equipped with a polypropylene filter for filtration and swelled for two hours in DMF (5 ml). The Fmoc group is removed according to the procedure described above, and the peptide according to the sequence is assembled as described under "Batchwise peptide synthesis on TentaGel S-RAM resins". After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin according to method a as described above and freeze dried from acetic acid. The crude peptide is purified by preparative HPLC using the procedure described above. The purified product is found to be homogeneous and the purity is found to be better than 95%. The identity of the peptide is confirmed by ES-MS. Yield 18.3%.

2. Peptide synthesis of Compound 2, H-His-Gly-Glu-Gly-thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-$(Lys)_6$-$NH_2$(des $Pro^{36}$-exendin-4(1–39)-$Lys_6$-$NH_2$)(SEQ ID NO: 93) on TentaGel S-RAM-Lys(Boc)Fmoc.

Dry TentaGel S-RAM-Lys(Boc)Fmoc resin (0.22 mmol/g, 1500 mg) is placed in a polyethylene vessel equipped with a polypropylene filter for filtration and swelled for two hours in DMF (5 ml). The Fmoc group on the first lysine is removed as described above and the synthesis is continued until finishing the peptide sequence as described under "Batchwise peptide synthesis on TentaGel S-Ram-Lys(Boc) Fmoc". After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin according to method a as described above and freeze dried from acetic acid. The crude freeze dried product is purified by preparative HPLC using the procedure described above. The purified product is found to be homogeneous and the purity is found to be better than 95%. The identity of the peptide is confirmed by ES-MS. Yield 22.1%

3. Peptide synthesis of Compound 3, H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-$(Lys)_6$-$NH_2$(exendin-4(1–39)-$Lys_6$-$NH_2$) (SEQ ID NO: 92) on TentaGel S-RAM-Lys(Boc)Fmoc.

Dry TentaGel S-RAM-Lys(Boc)Fmoc resin (0.22 mmol/g, 1000 mg) is placed in a polyethylene vessel equipped with a polypropylene filter for filtration and swelled for two hours in DMF (5 ml). The Fmoc group on the first lysine is removed as described above and the synthesis is continued until finishing the peptide sequence as described under "Batchwise peptide synthesis on TentaGel S-Ram-Lys(Boc) Fmoc". After completion of the synthesis, the peptide-resin is washed with DMF (3×5, 1 min each), DCM (3×5 ml, 1 min each), diethyl ether (3×5 ml, 1 min each) and dried in vacuo. The peptide is cleaved from the resin according to method a as described above and freeze dried from acetic acid. The crude freeze dried product is purified by preparative HPLC using the procedure described above. The purified product is found to be homogeneous and the purity is found to be better than 90%. The identity of the peptide is confirmed by ES-MS. Yield 20.5%.

4. Peptide synthesis of Compound 4, H-His-Gly-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-$(Lys)_6$-$NH_2$($Gly^8$-GLP1-(7–36) (Human)-$Lys_6$-$NH_2$) (SEQ ID NO. 88) on TentaGel S-RAM-Lys(Boc)Fmoc.

Dry TentaGel S-RAM-Lys(Boc)Fmoc resin (0.22 mmol/g, 1000 mg) is placed in a polyethylene vessel equipped with a polypropylene filter for filtration and swelled for two hours in DMF (5 ml). The Fmoc group on the first lysine is removed as described above and the synthesis is continued until finishing the peptide sequence as described under "Batchwise peptide synthesis on TentaGel S-Ram-Lys(Boc) Fmoc". After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin according to method a as described above and freeze dried from acetic acid. The crude freeze dried product is purified by preparative HPLC using the procedure described above. The purified product is found to be homogeneous and the purity is found to be better than 95%. The identity of the peptide is confirmed by ES-MS. Yield 11.7%.

4a. Peptide synthesis of Compound 4, H-His-Gly-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Lys-Lys-Lys-Lys-Lys-Lys-$NH_2$([$Gly^8$]hGLP-1(7–36)-$(Lys)_6$-$NH_2$) (SEQ ID NO: 88) on TentaGel S-RAM-Lys(Boc)Fmoc.

Dry TentaGel S-RAM-Lys(Boc)Fmoc resin (0.22 mmol/g, 2013 mg) is placed in a glass vessel equipped with a polypropylene filter for filtration and swelled for two hours in DMF (5 ml). The Fmoc group on the first lysine is removed as described above and the synthesis is continued until finishing the peptide sequence as described under "Batchwise peptide synthesis on TentaGel S-Ram-Lys(Boc) Fmoc". After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin according to method a as described above and freeze dried from acetic acid. The crude freeze dried product is purified by preparative HPLC using the procedure described above. The purified product is found to be homogeneous and the purity is found to be better than 90%. The identity of the peptide is confirmed by ES-MS. Yield 13%.

5. Peptide synthesis of Compound 5, H-His-Gly-Gly-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Lys(palmitoyl)-$(Lys)_6$-$NH_2$([$Gly^8$, $Lys^{37}$(palmitoyl)]GLP1 (7–36)(Human)-$(Lys)_7$-$NH_2$) (SEQ ID NO: 89) on TentaGel S-RAM-Lys(Boc)Fmoc.

Dry TentaGel S-RAM-Lys(Boc)Fmoc resin (0.22 mmol/g, 1000 mg) is placed in a polyethylene vessel equipped with a polypropylene filter for filtration and swelled for two hours in DMF (5 ml). The Fmoc group on the first lysine is removed as described above and the synthesis is continued until finishing the peptide sequence as described under "Batchwise peptide synthesis on TentaGel S-Ram-Lys(Boc) Fmoc". The reagent Fmoc-Lys(palmitoyl)-OH is coupled in a slightly modified manner due to its poor solubility in DMF. Approximately 400 mg of Fmoc-Lys(palmitoyl)-OH is dissolved in approximately 6 ml THF rather than DMF. After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin according to method b as described above and freeze dried from acetic acid. The crude freeze dried product is purified by preparative HPLC using the procedure describe above. The purified product is found to be homogeneous and the purity is found to be better than 95%. The identity of the peptide is confirmed by ES-MS. Yield 9.3%.

6. Peptide synthesis of Compound 6, H-His-Gly-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys(palmitoyl)-Gly-Arg-(Lys)$_6$-NH$_2$([Gly$^8$Lys$^{34}$(palmitoyl)]GLP1-(7–36)(Human)-(Lys)$_6$-NH$_2$) (SEQ ID NO: 90) on TentaGel S-RAM-Lys(Boc)Fmoc.

Dry TentaGel S-RAM-Lys(Boc)Fmoc resin (0.22 mmol/g, 1000 mg) is placed in a polyethylene vessel equipped with a polypropylene filter for filtration and swelled for two hours in DMF (5 ml). The Fmoc group on the first lysine is removed as described above and the synthesis is continued until finishing the peptide sequence as described under "Batchwise peptide synthesis on TentaGel S-Ram-Lys(Boc)Fmoc". The reagent Fmoc-Lys(palmitoyl)-OH is coupled in a slightly modified manner due to its poor solubility in DMF. Approximately 400 mg of Fmoc-Lys(palmitoyl-OH is dissolved in approximately 6 ml THF rather than DMF. After completion of the synthesis, the peptide-resin is washed with DMF (3×5 ml, 1 min each), DCM (3×5 ml, 1 min each), diethyl ether (3 ×5 ml, 1 min each) and dried in vacuo. The peptide is cleaved from the resin according to method a as described above and freeze dried from acetic acid. The crude freeze dried product is purified by preparative HPLC using the procedure described above. The purified product is found to be homogeneous and the purity is found to be better than 90%. The identity of the peptide is confirmed by ES-MS. Yield 4.2%.

7. Peptide synthesis of Compound 7, H-His-Gly-Glu-Gly-Thr-Phe-Thr-Ser-Asp-Val-Ser-Ser-Tyr-Leu-Glu-Gly-Gln-Ala-Ala-Lys(palmitoyl)-Glu-Phe-Ile-Ala-Trp-Leu-Val-Lys-Gly-Arg-(Lys)$_6$-NH$_2$([Gly$^8$, Lys$^{26}$(palmitoyl)]GLP1-(7–36)(Human)-(Lys)$_6$-NH$_2$) (SEQ ID NO: 103) on TentaGel S-RAM-Lys(Boc)Fmoc.

Dry TentaGel S-RAM-Lys(Boc)Fmoc resin (0.22 mmol/g, 1000 mg) is placed in a polyethylene vessel equipped with a polypropylene filter for filtration and swelled for two hours in DMF (5 ml). The Fmoc group on the first lysine is removed as described above and the synthesis is continued until finishing the peptide sequence as described under "Batchwise peptide synthesis on TentaGel S-Ram-Lys(Boc)Fmoc". The reagent Fmoc-Lys(palmitoyl)-OH is coupled in a slightly modified manner due to its poor solubility in DMF. Approximately 400 mg of Fmoc-Lys(palmitoyl)-OH is dissolved in approximately 6 ml THF rather than DMF. After completion of the synthesis, the peptide-resin is washed with DMF (3×5 ml, 1 min each), DCM (3×5 ml, 1 min each), diethyl ether (3 ×5 ml, 1 min each) and dried in vacuo. The peptide is cleaved from the resin according to method a as described above and freeze dried from acetic acid. The crude freeze dried product is purified by preparative HPLC using the procedure described above. The purified product is found to be homogeneous and the purity is found to be better than 90%. The identity of the peptide is confirmed by ES-MS. Yield 2.2%.

8. Peptide synthesis of Compound 8, H-Lys-Lys-Lys-Lys-Lys-Lys-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-NH$_2$ (H-(Lys)$_6$-des Pro$^{36}$exendin-4)1–39)-NH$_2$) on TentaGel S-RAM-Fmoc.

Dry TentaGel S-RAM-Fmoc resin (0.23 mmol/g, 1000 mg) is placed in a poly-ethylene vessel equipped with a polypropylene filter for filtration and swelled for two hours in DMF (5 ml). The Fmoc group on the resin is removed as described above and the synthesis is continued until finishing the peptide sequence as described under "Batchwise peptide synthesis on TentaGel S-Ram-Fmoc". After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin according to method a as described above and freeze dried from acetic acid. The crude freeze dried product is purified by preparative HPLC using the procedure described above. The purified product is found to be homogeneous and the purity is found to be better than 95%. The identity of the peptide is confirmed by ES-MS. Yield 26%.

9. Peptide synthesis of Compound 9, H-Lys$_6$-His-Gly-Glu-Gly-Thr-Phe-Thr-Ser-Asp-Leu-Ser-Lys-Gln-Met-Glu-Glu-Glu-Ala-Val-Arg-Leu-Phe-Ile Glu-Trp-Leu-Lys-Asn-Gly-Gly-Pro-Ser-Ser-Gly-Ala-Pro-Pro-Ser-(Lys)$_6$-NH$_2$ (H-Lys$_6$-des Pro$^{36}$exendin-4(1–39)-Lys$_6$-NH$_2$) on TentaGel S-RAM-Lys(Boc)Fmoc.

Dry TentaGel S-RAM-Lys(Boc)Fmoc resin (0.72 mmol/g, 1000 mg) is placed in a polyethylene vessel equipped with a polypropylene filter for filtration and swelled for two hours in DMF (5 ml). The Fmoc group on the first lysine is removed as described above and the synthesis is continued until finishing the peptide sequence as described under "Batchwise peptide synthesis on TentaGel S-Ram-Lys(Boc)Fmoc". After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin according to method a as described above and freeze dried from acetic acid. The crude freeze dried product is purified by preparative HPLC using the procedure described above. The purified product is found to be homogeneous and the purity is found to be better than 90%. The identity of the peptide is confirmed by ES-MS. Yield 32%.

10. Peptide synthesis of Compound 10, H-Lys-Lys-Lys-Lys-Lys-Lys-His-Gly-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Lys-Lys-Lys-Lys-Lys-Lys-NH$_2$ (H-(Lys)$_6$([Gly$^8$]hGLP-1(7–36)-(Lys)$_6$-NH$_2$) on TentaGel S-RAM-Lys(Boc)Fmoc.

Dry TentaGel S-RAM-Lys(Boc)Fmoc resin (0.22 mmol/g, 1000 mg) is placed in a polyethylene vessel equipped with a polypropylene filter for filtration and swelled for two hours in DMF (5 ml). The Fmoc group on the first lysine is removed as described above and the synthesis is continued until finishing the peptide sequence as described under "Batchwise peptide synthesis on TentaGel S-Ram-Lys(Boc)Fmoc". After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin according to method a as described above and freeze dried from acetic acid. The crude freeze dried product is purified by preparative HPLC using the procedure described above. The purified product is found to be homogeneous and the purity is found to be better than 90%. The identity of the peptide is confirmed by ES-MS. Yield 18%.

11. Peptide synthesis of Compound 11, H-Lys-Lys-Lys-Lys-Lys-Lys-His-Gly-Glu-Gly-Thr-Phe-Thr-Ser-Asp-Val-Ser- Ser-Thr-Leu-Glu-Gly-Gln-Ala-Ala-Lys-Glu-Phe-Ile-Ala-Trp-Leu-Val-Lys-Gly-Arg-NH$_2$ (H-(Lys)$_6$-[Gly$^8$]hGLP-1(7–36)-NH$_2$) on TentaGel S-RAM-Lys(Boc)Fmoc.

Dry TentaGel S-RAM-Fmoc resin (0.23 mmol/g, 1000 mg) is placed in a poly-ethylene vessel equipped with a polypropylene filter for filtration and swelled for two hours in DMF (5 ml). The Fmoc group on the resin is removed as described above and the synthesis is continued until finishing the peptide sequence as described under "Batchwise peptide synthesis on TentaGel S-Ram-Fmoc". After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin according to method a as described above and freeze dried from acetic acid. The crude freeze dried product is purified by preparative HPLC using the procedure described above. The purified product is found to be homogeneous and the purity is found to be better than 98%. The identity of the peptide is confirmed by ES-MS. Yield 15%.

12. Peptide synthesis of Compound 12, H-His-Gly-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Lys-Lys-Lys-Lys-Lys-Lys-Lys-Lys-NH$_2$ ([Gly$^8$]hGLP-1(7–36)-(Lys)$_8$-NH$_2$) on TentaGel S-RAM-Lys(Boc)Fmoc.

Dry TentaGel S-RAM-Lys(Boc)Fmoc resin (0.22 mmol/g, 1000 mg) is placed in a polyethylene vessel equipped with a polypropylene filter for filtration and swelled for two hours in DMF (5 ml). The Fmoc group on the first lysine is removed as described above and the synthesis is continued until finishing the peptide sequence as described under "Batchwise peptide synthesis on TentaGel S-Ram-Lys(Boc)Fmoc". After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin according to method a as described above and freeze dried from acetic acid. The crude freeze dried product is purified by preparative HPLC using the procedure described above. The purified product is found to b homogeneous and the purity is found to be better than 98%. The identity of the peptide is confirmed by ES-MS. Yield 4.2%.

13. Peptide synthesis of Compound 13, H-His-Gly-Glu-Gly-Thr-Phe-Thr-Phe-Thr-Ser-Asp-Val-Ser-Ser-Try-Leu-Glu-Gly-Gln-Ala-Ala-Lys-Glu-Phe-Ile-Ala-Trp-Leu-Val-Lys-Gly-Arg-Lys-Lys-Lys-Lys-Lys-Lys-Lys-Lys-Lys-Lys-NH$_2$ ([Gly$^8$]hGLP-1(7–36)-(Lys)$_{10}$-NH$_2$) on TentaGel S-RAM-Lys(Boc)Fmoc.

Dry TentaGel S-RAM-Lys(Boc)Fmoc resin (0.22 mmol/g, 1000 mg) is placed in a polyethylene vessel equipped with a polypropylene filter for filtration and swelled for two hours in DMF (5 ml). The Fmoc group on the first lysine is removed as described above and the synthesis is continued until finishing the peptide sequence as described under "Batchwise peptide synthesis on TentaGel S-Ram-Lys(Boc)Fmoc". After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin according to method a as described above and freeze dried from acetic acid. The crude freeze dried product is purified by preparative HPLC using the procedure described above. The purified product is found to be homogeneous and the purity is found to be better than 95%. The identity of the peptide is confirmed by ES-MS. Yield 2%.

14. Peptide synthesis of Compound 14, H-His-Gly-Glu-Gly-Thr-Phe-Thr-Ser-Asp-Leu-Ser-Lys-Glu-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser-NH$_2$ (H-des Pro$^{36}$, Pro$^{37}$, Pro$^{38}$exendin-4(1–39)-NH$_2$) on TentaGel S-RAM-Fmoc.

Dry TentaGel S-RAM-Fmoc resin (0.23 mmol/g, 1000 g) is placed in a poly-ethylene vessel equipped with a polypropylene filter for filtration and swelled for two hours in DMF (5 ml). The Fmoc group on the resin is removed as described above and the synthesis is continued until finishing the peptide sequence as described under "Batchwise peptide synthesis on TentaGel S-Ram-Fmoc". After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin according to method a as described above and freeze dried from acetic acid. The crude freeze dried product is purified by preparative HPLC using the procedure described above. The purified product is found to by homogeneous and the purity is found to be better than 95%. The identity of the peptide is confirmed by ES-MS. Yield 11%.

15. Peptide synthesis of Compound 15, H-Lys-Lys-Lys-Lys-Lys-Lys-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser-NH$_2$ (H-(Lys)$_6$-des Pro$^{36}$, Pro$^{37}$, Pro$^{38}$exendin-4(1–39)-NH$_2$) on TentaGel S-RAM-Fmoc.

Dry TentaGel S-RAM-Fmoc resin (0.23 mmol/g, 1000 mg) is placed in a poly-ethylene vessel equipped with a polypropylene filter for filtration and swelled for two hours in DMF (5 ml). The Fmoc group on the resin is removed as described above and the synthesis is continued until finishing the peptide sequence as described under "Batchwise peptide synthesis on TentaGel S-Ram-Fmoc". After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin according to method a as described above and freeze dried from acetic acid. The crude freeze dried product is purified by preparative HPLC using the procedure described above. The purified product is found to be homogeneous and the purity is found to be better than 94%. The identity of the peptide is confirmed by ES-MS. Yield 17%.

16. Peptide synthesis of compound 16, H-Asn-Glu-Glu-Glu-Glu-Glu-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser-NH$_2$ (H-Asn-(Glu)$_5$-des Pro$^{36}$, Pro$^{37}$, Pro$^{38}$exendin-4(1–39)-NH$^2$) on TentaGel S-RAM-Fmoc.

Dry TentaGel S-RAM-Fmoc resin (0.23 mmol/g, 1000 mg) is placed in a poly-ethylene vessel equipped with a polypropylene filter for filtration and swelled for two hours in DMF (5 ml). The Fmoc group on the resin is removed as described above and the synthesis is continued until finishing the peptide sequence as described under "Batchwise peptide synthesis on TentaGel S-Ram-Fmoc". After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin according to method a as described above and freeze dried from acetic acid. The crude freeze dried product is purified by preparative HPLC using the procedure described above. The purified product is found to be homogeneous and the purity is found to be better than 90%. The identity of the peptide is confirmed by ES-MS. Yield 9%.

17. Peptide synthesis of Compound 17, Compound 3, H-(Lys)$_6$-His-Gly-Glu-Gly-Thr-Phe-Thr-Ser-Asp-Leu-Ser- Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser-(Lys)$_6$-NH$_2$ (H-(Lys)$_6$-des Pro$^{36}$, Pro$^{37}$, Pro$^{38}$exendin-4 (1–39)-(Lys)$_6$-NH$_2$) on TentaGel S-RAM-Lys(Boc)Fmoc.

Dry TentaGel S-RAM-Lys(Boc)Fmoc resin (0.22 mmol/g, 1000 mg) is placed in a polyethylene vessel equipped with a polypropylene filter for filtration and swelled for two hours in DMF (5 ml). The Fmoc group on the first lysine is removed as described above and the synthesis is continued until finishing the peptide sequence as described under "Batchwise peptide synthesis on TentaGel S-Ram-Lys(Boc) Fmoc". After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin according to method a as described above and freeze dried from acetic acid. The crude freeze dried product is purified by preparative HPLC using the procedure described above. The purified product is found to be homogeneous and the purity is found to be better than 90%. The identity of the peptide is confirmed by ES-MS. Yield 10%.

18. Peptide synthesis of Compound 18, H-Asn-Glu-Glu-Glu-Glu-Glu-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser-(Lys)$_6$-NH$_2$ (H-Asn-(Glu)$_5$-des Pro$^{36}$, Pro$^{37}$, Pro$^{38}$exendin-4(1–39)-(Lys)$_6$-NH$_2$) on TentaGel S-RAM-Lys(Boc)Fmoc.

Dry TentaGel S-RAM-Lys(Boc)Fmoc resin (0.22 mmol/g, 1000 mg) is placed in a polyethylene vessel equipped with a polypropylene filter for filtration and swelled for two hours in DMF (5 ml). The Fmoc group on the first lysine is removed as described above and the synthesis is continued until finishing the peptide sequence as described under "Batchwise peptide synthesis on TentaGel S-Ram-Lys(Boc) Fmoc". After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin according to method a as described above and freeze dried from acetic acid. The crude freeze dried product is purified by preparative HPLC using the procedure described above. The purified product is found to be homogeneous and the purity is found to be better than 92%. The identity of the peptide is confirmed by ES-MS. Yield 14%.

19. Peptide synthesis of Compound 19, H-His-Gly-Glu-Gly-Thr-Phe-Thr-Phe-Thr-Ser-Asp-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser-(Lys)$_6$-NH$_2$ (des Pro$^{36}$, Pro$^{37}$, Pro$^{38}$exendin-4(1–39)-(Lys)$_6$-NH$_2$) on TentaGel S-RAM-Lys(Boc)Fmoc.

Dry TentaGel S-RAM-Lys(Boc)Fmoc resin (0.22 mmol/g, 1000 mg) is placed in a polyethylene vessel equipped with a polypropylene filter for filtration and swelled for two hours in DMF (5 ml). The Fmoc group on the first lysine is removed as described above and the synthesis is continued until finishing the peptide sequence as described under "Batchwise peptide synthesis on TentaGel S-Ram-Lys(Boc) Fmoc". After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin according to method a as described above and freeze dried from acetic acid. The crude freeze dried product is purified by preparative HPLC using the procedure described above. The purified product is found to be homogeneous and the purity is found to be better than 97%. The identity of the peptide is confirmed by ES-MS. Yield 19%.

20. Recombinant preparation of Compound 2

Construction of the pYES0010 Expression Vector

Figure 6:
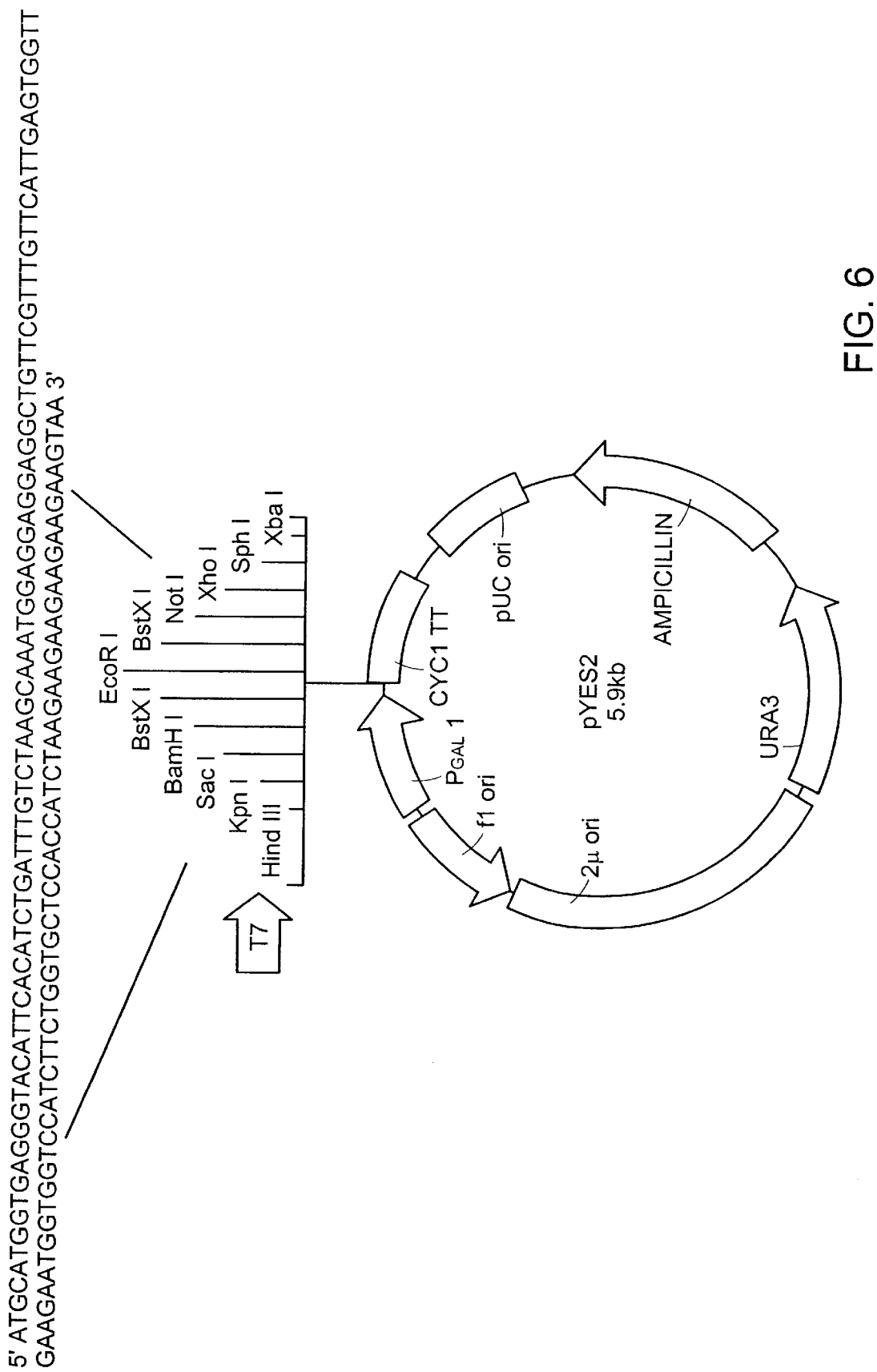
FIG. 6 shows a synthetic cDNA constructed for heterlog expression of Compound 2 in yeast. The new construct was designated pYES0010, cf. Example 20.

A synthetic cDNA was constructed for heterolog expression in yeast. The protein sequence encoding Compound 2 was back translated using a *Saccharomyces cerevisiae* condon usage table (Saccharomyces Genome Database). To enable translation of the synthetic cDNA an additional ATG start codon was added to the 5' end and a TAA stop codon was added to the 3' end. The construct was inserted into HindIII and The EcoRI site of the pYES2 shuttle vector comprising an ampicilline resistance gene, and the new construct was designated pYES0010, cf. FIG. 6. pYES0010 was subsequently transformed into *E. coli* and subjected to ampicillin selection pressure. Positive clones were selected and sequenced.

Transformation into Yeast

In order to make transform the pYES0010 into the yeast haploid INVScl:MATa hes3delta1 leu2 trip1–289 ura3–52. Yeast were grown in YPD medium (1% yeast extract, 2% peptone, 2% glucose, and 0.004% adenine sulfate) at 30 C to saturation. 1 ml of culture was harvested for transformations. 2 μl of 10 mg/ml carrier DNA was added and 1 μg of pYES0010 was added and mixed: 0.5 ml (45% PEG4000, 1M Li OAc, 0.5M EDTA and 1M Tris-HCl (pH 7.5) was added and mixed. Finally 20 μl 1M DTT was added and the mixture was incubated for 16 h at room temperature. After incubation the cells were heat shocked at 42 C for 10 min and plated selective plates (6.7% yeast nitrogen base, 2% glucose, 20 μg/ml adenine, 20 μg/ml arginine, 29 μg/ml isoleucine, 20 μg/ml histidine, 60 μg/ml leucine, 20 μg/ml lysine, 20 μg/ml tryptophan, 20 μg/ml methionine 50 μg/ml phenylalanine 150 μg/ml valine, 30 μg/ml Tyrosine and 2.5% agar. Plates were incubated at 30 C for 3 to 5 days until transformants appear.

Expression and Purification of Compound 2

Transformants were cultivated in selective media (6.7% Yeast nitrogen base, 2% glucose, 20 μg/ml adenine, 20 μg/ml arginine, 29 μg/ml isoleucine, 20 μg/ml histidine, 60 μg/ml leucine, 20 μg/ml lysine, 20 μg/ml Tryptophan, 20 μg/ml methionine 50 μg/ml phenylalanine 150 μg/ml valine, 30 μg/ml Tyrosine) for 1.5 days. The cells were harvested and resuspended in galactose induction medium (6.7% Yeast nitrogen base, 4% galactose, 20 μg/ml adenine, 20 μg/ml arginine, 29 μg/ml isoleucine, 20 μg/ml histidine, 60 μg/ml leucine, 20 μg/ml lysine, 20 μg/ml Tryptophan, 20 μg/ml methionine 50 μg/ml phenylalanine 150 μg/ml valine, 30 μg/ml Tyrosine for 1 day. The cells were harvested and homogenized in 10 mM Tris-HCl pH 7.5 containing protease inhibitors (Roche). The lysate was clarified centrifugation at 20,000×g for 30 min. The supernatant was loaded onto a Superdex 12 HR 10/30 column (Amersham Pharmacia Biotech) equilibrated with 10 mM Tris-HCl pH 7.5. The column was eluted in 50 Mm ammonia bicarbonate buffer pH 8.0. Samples containing recombinant Compound 2 were pooled. The N-terminal methionine was removed by methionine aminopeptidase and the samples were further purified on a HPLC Column.

HPLC Settings for Compound 2 Purification

| | |
|---|---|
| HPLC column: | Kromasil RP C8; K 100-10-C8 nr. CER 2230. compound |
| Temp: | 22 C. |
| Flow rate: | 35 ml/min |
| HPLC solvents: | |
| A: | 0.10% trifluoroacetic acid in water |
| B: | 0.10% trifluoroacetic acid in acetonitrile:water 90:10. |

Compound 2 was eluted from the HPLC column with 0.10% trifluoroacetic acid in 20% to 80% Acetonitrile in 40 min. particles was used with the instrument. A SHT200D block heater from Stuart Scientific was used for heating of the peptide/enzyme solutions during the stability experiments. The degradation of the test compounds was studied at 37° C. in 50 mM phosphate buffer solutions of pH 7.4 containing leucine aminopeptidase (25 U/ml) or carboxypeptidase A (1 U/ml) or 100 mM ammoniumbicarbonate buffer of pH 8.0 containing dipeptidyl aminopeptidase IV (0.5 U/ml). Experiments were initiated by addition of an aliquot (100 µl) of a stock solution (1 mg/ml) of the peptide in water to 900 µl preheated enzyme solution in an Eppendorf microvial giving an initial concentration of 0.1 mg/ml (~1.7·10−5–1.8·10−5 M) of the peptide. The peptide/enzyme solution was kept at 37° C. and at appropriate time intervals samples of 100 µl were withdrawn from the peptide/enzyme solution and mixed thoroughly with 20 µl 25% TFA in acetonitrile in order to stop the enzymatic degradation process. The inactivated samples were transferred to autosampler vials and analysed for content of intact test compound by HPLC as described below. Half-lives (t½) for the test compounds in enzyme solutions were calculated from plots of natural logarithm to the residual concentration (i.e. HPLC peak heights) against time using the formula:

$$t\tfrac{1}{2} = 1/k_{obs} \cdot ln(2),$$

where $k_{obs}$ is the apparent first-order rate constant for the observed degradation.

HPLC Analysis

Samples from the stability experiments performed as described above were analysed by gradient HPLC analysis using the instrumentation described above and the following experimental conditions.

| | |
|---|---|
| Compound 2 | 12.25 mg |
| Sodiumdihydrogenphosphate | 1.380 g |
| Parahydroxybenzoate | 0.1 g |
| Aqua ad injectabile | 100 ml |

The experimental results obtained from the individual stability experiments are shown in Table 1 below. It appears from the table that the half life of the compounds of the invention is considerably extended in solution with all enzymes tested.

21. Injection formulations of peptide

Fixed dose formulations of peptide for intra venous injection are prepared by dissolving the peptide in sterile, isotonic saline, and storing the resulting solution in glass ampoules filled with inert gas under sterile conditions. Each dose of the peptide is stored dry in ampoules or capped vials filled with inert gas. Multi-dose formulations of peptide for intra venous injection are prepared by dissolving the peptide in sterile, isotonic saline, storing the resulting solution in capped vials, if necessary adding preservative (for instance 0.1% parahydroxybenzoate, 1% benzyl alcohol or 0.1% chlorocresole). Example of multi-dose peptide formulation:

| | |
|---|---|
| Column temperature: | 30° C. |
| Injection volume: | 10 µl |
| Mobile phase A: | 0.1% TFA in water |
| Mobile phase B: | 0.085% TFA in acetonitrile (ACN) |
| Gradient: | 32–52% B in 21 min |
| Detection: | UV at 215 nm |

22. Stability Experiments

In vitro stability studies with the present peptides and peptide conjugates in the presence of selected proteolytic enzymes are applied as a tool for evaluating the protection of said peptides against proteolysis in vivo. The aim of the experiments performed was to measure and compare the in vitro stability of Compounds 4, 5, 6 and 7 to that of the prior art compounds Compound(iii) H-(Gly$^8$)-hGLP-1(7–36)-NH$_2$ and hGLP-1(7–36)-NH$_2$ in solutions of one or more of the enzymes leucine aminopeptidase, carboxypeptidase A and dipeptidyl aminopeptidase IV at 37° C.

Materials and Apparatus for in Vitro Stability

Water used was of highest quality obtained from a Milli-Q water treatment system (Millipore, Bedford, Mass., U.S.A.). Acetonitrile (ACN) was of super gradient quality obtained from Labscan Ltd. (Dublin, Ireland). Trifluoracetic acid (TFA) 99.9% dihydrogen phosphate (NaH$_2$PO$_4$), sodium hydroxide (NaOH) and all other chemicals used were of analytical grade. Leucine aminopeptidase (EC 3.4.11.1), Carboxypeptidase A (EC 3.4.17.1) and Dipeptidyl peptidase (Dipeptidyl aminopeptidase IV, EC 3.4.14.5) were all obtained from Sigma (St. Louis, Mo., U.S.A.). Gradient HPLC analysis was done using a Hewlett Packard HP 1100 HPLC system consisting of a HP 1100 Binary Pump, a HP 1100 Autosampler, A HP 1100 Column Thermostat and a HP 1100 Variable Wavelength Detector. Hewlett Packard Chemstation for LC software (Rev. A.06.01) was used for instrument control and data acquisition. A Vydac 238TP54 (150× 4.6 mm I.D.) column packed with 5 µm, C18, 300 Å

TABLE 1

Test Compound

| Compound No. | Name | Enzyme Solution Enzyme | Conc. | Half-life ($t_{1/2}$) |
|---|---|---|---|---|
| Compound 5 | H-(Gly$^8$)-hGLP-1(7-36)-Lys(Palm)-Lys$_6$-NH$_2$ | LAP | 25 U/ml | >3 days |
| | | CPA | 1 U/ml | >2 days |
| | | DPP IV | 0.5 U/ml | 440 min |
| Compound 7 | H-(Gly$^8$, Lys$^{26}$(Palm))-hGLP-1(7-36)-Lys$_6$-NH$_2$ | LAP | 25 U/ml | 1150 min |
| | | CPA | 1 U/ml | 1058 min |
| | | DPP IV | 0.5 U/ml | 526 min |
| Compound 6 | H-(Gly$^8$, Lys$^{34}$(Palm))-hGLP-1(7-36)-Lys$_6$-NH$_2$ | LAP | 25 U/ml | ~1.5 day |
| | | CPA | 1 U/ml | >1 day |
| | | DPP IV | 0.5 U/ml | 177 min |
| GLP-1 | H-hGLP-1(7-36)-NH$_2$ | LAP | 25 U/ml | 152 min |
| | | CPA | 1 U/ml | 48 min |
| | | DPP IV | 0.5 U/ml | 2.0 min |
| Compound 4 | H-(Gly$^8$)-hGLP-1(7-36)-Lys$_6$-NH$_2$ | LAP | 25 U/ml | ~1.5 day |
| | | CPA | 1 U/ml | 145 min |
| | | DPP IV | 0.5 U/ml | 292 min |

TABLE 1-continued

| Test Compound | | Enzyme Solution | | Half-life |
|---|---|---|---|---|
| Compound No. | Name | Enzyme | Conc. | ($t_{1/2}$) |
| Compound (iii) | H-(Gly$^8$)-hGLP-1(7-36)-NH$_2$ | LAP | 25 U/ml | 693 min |
| | | CPA | 1 U/ml | 127 min |
| | | DPP IV | 0.5 U/ml | 56 min |

LAP: Leucine aminopeptidase, CPA: Carboxypeptidase A, DPP IV: Dipeptidyl aminopeptidase IV 23. In vitro Stability Studies of Compound (iii) and Compound 4 in Rat Plasma The degradation of the two test compounds and in heparin stabilised rat (Sprague-Dawley) plasma was followed by the combination of solid phase extraction and LC-MS. The degradation was followed for 720 minutes in plasma. The half-life of Compound (iii) was found to be 238 min. in rat plasma. This finding was compared with the half-life of Compound 4, which was found to be 466 min. in rat plasma.

Materials and Methods

Blank rat plasma in sodium heparin (5000 units/mL) were obtained from Harlan Sera Lab Ltd. (Loughborough, UK). Test Substances and Solutions The test substances used in the study are listed in the table below. For the in vitro experiments a stock solution of 100 µg/ml milli-Q g/ml water was used (corresponding to 26.0 µM Compound (iii) H-(Gly$^8$)-GLP-1-NH$_2$ or 17.8 µM Compound 4).

| Substance Name | Batch No. | Average Mw. | Peptide Content |
|---|---|---|---|
| Compound (iii) | ZP 7,73-1F | 3284 g/mol | 85% |
| Compound 4 | ZP 7,69-1C | 4053 g/mol | 72% |

The LC-MS analysis was performed on an HP 1100 instrument consisting of an on-line degasser, a quaternary gradient pump, an auto sampler, a column oven, Hewlett Packard (Wilmington. Del., U.S.A.) in combination with a Quattro Ultima mass spectrometer from Micromass (Altrincham, UK). Both the LC and MS were controlled by MassLynx 3.3 software. The LC separations prior to MS detection were performed on a Vydac 218MS52 (2.1×250 mm) column (Hesperia, Calif., U.S.A.).

The initial plasma volume was 1000 µl (37° C.). From the initial plasma volume, 100 µl was transferred to a 0.75 ml HPLC vial (used as blank), mixed with 560 µl extraction solution (MeCN:0.18 M ammonium carbonate pH 9.5 (6:94 v/v), 4 C) and extracted by Solid Phase Extraction using ASPEC XL4 Robot. A volume of 100 µl stock solution was added to the remaining 900 µl plasma, mixed thoroughly and incubated at 37 C (corresponding to an initial concentration of 10 µg of the test compounds/ml). At each time point (0.2, 60, 120, 180, 240, 360, 480, 662 and 720 min., respectively) 100 µl of the drug containing plasma was collected, mixed with 560 µl ice cold extraction solution and immediately extracted by SPE as described above. The extracted plasma samples were analysed by LC-MS.

The LC-MS analysis were performed on an HP 1100 series LC in combination with a Quattro Ultima II triple quadrupole MS instrument.

The samples were kept at 18°C. in the autosampler tray prior to injection of 10 µl. The separations were performed at 30° C. on a Vydac 218MS52 (2.1×250 mm) LC column using a linear gradient from 15 to 50% B within 14 min. at a flow rate of 250 µl/min. 0.1% formic acid in water was used as mobile phase A and 0.1% formic acid in MeCN as mobile phase B. Compound 4 and Compound (iii) were detected by single ion recording (SIR) using the 6 H+(m/z=676.7) and 4 H+(m/z=822.1) ion species, respectively. The cone voltage for the analysis of compound (iii) and Compound 4 was set to 100 and 70 V, respectively. The in vitro stability of Compound (iii) and Compound 4 have been investigated in rat plasma by LC-MS. The degradation of the two compounds were followed for 720 min. and the results were plotted as the natural logarithm of the peak area vs. time. The degradation rates ($k_{obs}$) of the compounds were found as the slope after linear regression, and the half-life (T½) was found as ln $2/k_{obs}$. The results from the experiment are listed below.

Degradation Study over 720 minutes in Rat Plasma

| Compound | T½ (min) | $k_{obs}$ (min$^{-1}$) | r$^2$ |
|---|---|---|---|
| Compound (iii) | 238.4 | 0.0029 | 0.9785 |
| Compound 4 | 466.1 | 0.0015 | 0.8596 |

The conclusion of the experiment is therefore that the provision of a C-terminal Lys$_6$ peptide conjugation to the (Gly$^8$) hGLP-1(7–36) sequence results in a two fold increased stability in rat plasma.

24. Single Dose Effect of oral and parenteral administration of Compound 5 on Blood Glucose Levels in Diabetic ob/ob Mice.

The compounds of the invention possess blood glucose lowering properties. This was examined using Compound 5 to test the effect on blood glucose (BG) levels in the ob/ob mutant mice after intraperitoneal (i.p.) and peroral (p.o.) administration. Compound 5 reduced BG levels in diabetic mice in a dose of 110 µg/mouse when administered i.p. Likewise p.o. administration of Compound 5 elicited a similar decrease in BG levels in a dose of 1100 µg/mouse, but not at lower doses.

Experimental

Forty female diabetic ob/ob mice (Umeå strain, Bomholtgaard), which are obese due to a dominant mutant leptin (Tomita, T., Doull, V., Pollock, H. G., and Krizsan, D. 1992. Pancreatic islets of obese hyperglycemic mice (ob/ob). Pancreas 7: 367–75) were housed (3 mice/cage) under controlled ambient conditions following a 12:12-h light: dark cycle and fed standard Altromin no 1324 diet with free access to tap water. At arrival the animals were 8 weeks of age. The mice were allowed 2 weeks of acclimatization before experiments were initiated. At the time of experiment the mice were 13 weeks old with a body weight of 41.8±3.2 g (mean±SD; n=42). Handling of the mice one and three days before the experiment was performed in order to reduce stress-induced BG excursions. On the day of the experiment, blood was taken from the tip of the tail 2–3 hours after the light was turned on. A single drop of blood (<5 µl) was dropped on the glucose strip for analysis and measured by an Elite Autoanalyser, Bayer, Denmark. Whole blood glucose (BG) concentration was analysed by the immobilised glucose oxidase method. Blood glucose levels varied between normoglycaemia and severe hyperglycaemia (range: 3.6–15.6 mM; mean±SD: 9.4±3.3 mM: n=42). Six animals with BG <5.8 mM were excluded from the study (total n=36). The remaining animals were stratified based on their BG levels in order to ensure that the mean BG was similar among groups. One hour after the initial control blood sampling, drugs were administered and BG was measured at t=60 min, t=120 min, t=240 min, t=480 min.

Peptides and Other Materials

Compound 5 (batch nr. ZP 3.12 fraction 1–2. Purification) was synthesised by the Department of Chemistry, Zealand Pharmaceuticals. The peptide was dissolved in sterile isotonic NaCl shortly before dosing and given in a volume of 0.2 ml. The same solutions were used for both p.o. and i.p. administration. For each animal, a data log sheet was filled out at the time of each blood sampling.

Drug Administration

Animals were administered with Compound 5, and the maximum dose was 1100 μg/mouse and the lowest dose was 1.1 μg/mouse, As a negative control, saline was administered p.o. and as positive control the test compound was given i.p. in a dose of 110 μg/mouse.

During control conditions, BG levels in non-fasted ob/ob mice were similar in all groups (individual group data not shown), but within groups, there was a great scatter on BG levels (BG range for all animals: 5.8–15.6 mM). Therefore, to correct for the varying degree of hyperglycemia, results are expressed as the relative difference from baseline (% control). Intraperitoneal administration of 110 μg Compound 5 produced a sustained decrease in BG that reached nadir at 1–2 hrs after administration of the compound. No changes were observed in saline treated animals. In most groups (5/6), BG increased between 4 and 8 hrs after drug administration. Compound 5 reduced the BG levels in a dose of 110 μg/mouse when administered i.p. in diabetic ob/ob mice (data not shown). The antidiabetic effect was observed after 60 minutes and was maximal 2–4 h after administration of the compound. Furthermore, a long-lasting effect (>8 hours) suggests that Compound 5 has a longer duration of action than the notoriously short-acting native GLP-1 (Bailey, C. J. & Flatt, P. R. 1987. Glucagon-like peptide-1 and the entero-insular axis in obese hyperglycaemic (ob/ob) mice. Life Sci, 40, 521–5). The dose 1100 μg/mouse p.o. elicited a similar decrease in BG as observed in animals treated with 110 μg i.p.

We have shown that Compound 5 effectively lowers BG levels in diabetic ob/ob mice following i.p. administration of 110 μg/mouse the compound. A similar effect is seen after 1100 μg/mouse of Compound 5 when given by the oral route. This suggests that the compound is absorbed from the gastrointestinal tract.

25. In vivo Studies with

Compound 1 (des Pro$^{36}$-exendin-4(1–39)-NH$_2$ (SEQ ID NO:101)),

Compound 2 (des Pro$^{36}$-exendin-4(1–39)-Lys$_6$-NH$_2$ (SEQ ID NO:93)),

Compound (iii) (Gly$^8$-GLP1-(7–36) (Human)-NH$_2$ (SEQ ID NO:87)),

Compound 4 (Gly$^8$-GLP1-(7–36) (Human)-Lys$_6$-NH$_2$ (SEQ ID NO:88)) and

Compound 5 (Gly$^8$Lys$^{37}$(palmitoyl)-GLP1-(7–36)(Human)-Lys$_7$-NH$_2$(SEQ ID NO:89))

Various concentrations of each peptide are administered orally and intraperitoneally to ob/ob mice to determine if these compounds affect blood glucose levels. The experimental conditions used were the same as described in Example 24.

Peptides and Other Materials

Des Pro$^{36}$-exendin-1(1–39)-NH$_2$ (Compound 1, SEQ ID NO:101) and the same peptide, but with an additional sequence, Lys$_6$, attached at the C-terminal, des Pro$^{36}$-exendin-4(1–39)-Lys$_6$-NH$_2$ (Compound 2, SEQ ID N0:93), Gly$^8$-GLP1-(7–36)(Human)-NH$_2$ (Compound (ii), SEQ ID NO:87)and the same peptide, but with an additional sequence, Lys$_6$, attached at the C-terminal, Gly$^8$-GLP1-(7–36)(Human)-Lys$_6$-NH$_2$ Compound 4, SEQ ID NO:88) and Gly$^8$Lys$^{37}$(palmitoyl)-GLP1-(7–36)(Human)-Lys$_7$-NH$_2$ Compound 5, SEQ ID NO:89) are synthesized using methods described above. Solutions are prepared on the morning of dosing, immediately before the animals are administered. The same solutions are used for both peroral and interperitoneal administration. All peptides are dissolved in sterile isotonic NaCl and given in a volume of 0.2 ml. All experiments are carried out in the same mice to compare the active doses of the peptides shown in Table 2. Blood sampling is performed as described above and the animals are administered with the doses shown in Table 3. As negative control, saline is administered perorally. Results are shown in Table 4.

TABLE 2

| Number | Compound |
| --- | --- |
| Compound 1 | des Pro$^{36}$-exendin-4(1-39)-NH$_2$ (SEQ ID NO:101) |
| Compound 2 | des Pro$^{36}$-exendin-4(1-39)-Lys$_6$-NH2 (SEQ ID NO:93) |
| Compound (ii) | Gly$^8$-GLP1-(7-36)(Human)-NH2 (SEQ ID NO:87) |
| Compound 4 | Gly$^8$-GLP1-(7-36)(Human)-Lys$_6$-NH2 (SEQ ID NO:88) |
| Compound 5 | Gly$^8$Lys$^{37}$(palmitoyl)-GLP1-(7-36)(Human)-Lys$_7$-NH$_2$ (SEQ ID NO:89) |

TABLE 3

| Compound | Group 1 Dose peroral μg/ mouse | Group 2 Dose peroral μg/ mouse | Group 3 Dose peroral μg/ mouse | Group 4 Dose peroral μg/ mouse | Group 5 Dose peroral μl/ mouse Isotonic saline | Group 6 Dose i.p μg/ mouse |
| --- | --- | --- | --- | --- | --- | --- |
| Compound 1 | 400 | 40 | 4 | 0.4 | 200 μl | 40 |
| Compound 2 | 1000 | 100 | 10 | 1 | 200 μl | 100 |
| Compound (ii) | 1000 | 100 | 10 | 1 | 200 μl | 100 |
| Compound 4 | 1000 | 100 | 10 | 1 | 200 μl | 100 |
| Compound 5 | 1000 | 100 | 10 | 1 | 200 μl | 100 |

Group data were summarised as the mean ±SEM of the individual results in each treatment group. In order to analyse the effects of the compounds, the absolute and the relative (% of t=0) difference from baseline was calculated for each time point.

TABLE 4

| | 0 | 1 hour | 2 hours | 4 hours |
| --- | --- | --- | --- | --- |
| Compound 1—saline | 100 | 103 | 107 | 92 |
| Compound 1—400 μg po | 100 | 93 | 88 | 93 |
| Compound 1—40 μg po | 100 | 89 | 89 | 91 |
| Compound 1—4 μg po | 100 | 105 | 88 | 91 |
| Compound 1—0.4 μg po | 100 | 106 | 103 | 100 |
| Compound 1—40 μg ip | 100 | 68 | 69 | 74 |
| Compound 2—saline | 100 | 100 | 112 | 114 |
| Compound 2—1000 μg po | 100 | 67 | 69 | 64 |
| Compound 2—100 μg po | 100 | 78 | 71 | 72 |
| Compound 2—10 μg po | 100 | 86 | 72 | 72 |
| Compound 2—1 μg po | 100 | 112 | 101 | 96 |
| Compound 2—100 μg ip | 100 | 75 | 67 | 63 |
| Compound (ii)—saline | 100 | 95 | 87 | 100 |
| Compound (ii)—1000 μg po | 100 | 87 | 105 | 94 |
| Compound (ii)—100 μg po | 100 | 118 | 111 | 92 |

TABLE 4-continued

| | 0 | 1 hour | 2 hours | 4 hours |
|---|---|---|---|---|
| Compound (ii)—10 μg po | 100 | 101 | 94 | 104 |
| Compound (ii)—1 μg po | 100 | 94 | 89 | 96 |
| Compound (ii)—100 μg ip | 100 | 70 | 60 | 81 |
| Compound 4—saline | 100 | 102 | 94 | 79 |
| Compound 4—1000 μg po | 100 | 128 | 72 | 78 |
| Compound 4—100 μg po | 100 | 72 | 70 | 58 |
| Compound 4—10 μg po | 100 | 98 | 95 | 81 |
| Compound 4—1 μg po | 100 | 99 | 89 | 84 |
| Compound 4—100 μg ip | 100 | 83 | 58 | 56 |
| Compound 5—saline | 100 | 90 | 86 | 103 |
| Compound 5—1000 μg po | 100 | 73 | 75 | 67 |
| Compound 5—100 μg po | 100 | 97 | 140 | 107 |
| Compound 5—10 μg po | 100 | 90 | 120 | 126 |
| Compound 5—1 μg po | 100 | 111 | 133 | 114 |
| Compound 5—100 μg ip | 100 | 63 | 50 | 52 |

Figure 2:
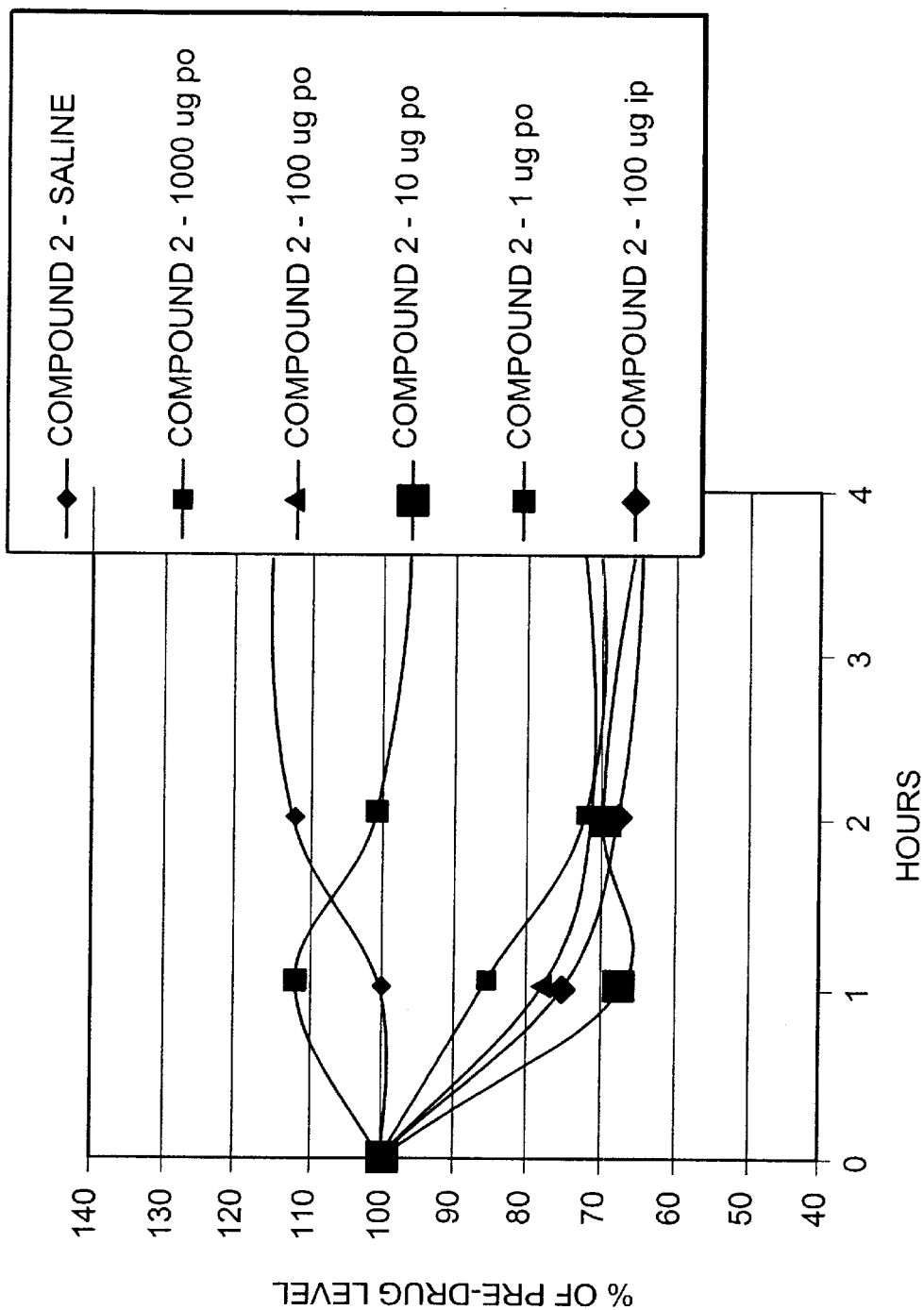
FIG. 2 shows the effect of Compound 2 (SEQ ID NO:93) (des PRO$^{36}$-exendin-4(1–39)-Lys$_6$-NH$_2$ on the blood glucose levels of mice, cf. Example 25.
Figure 3:
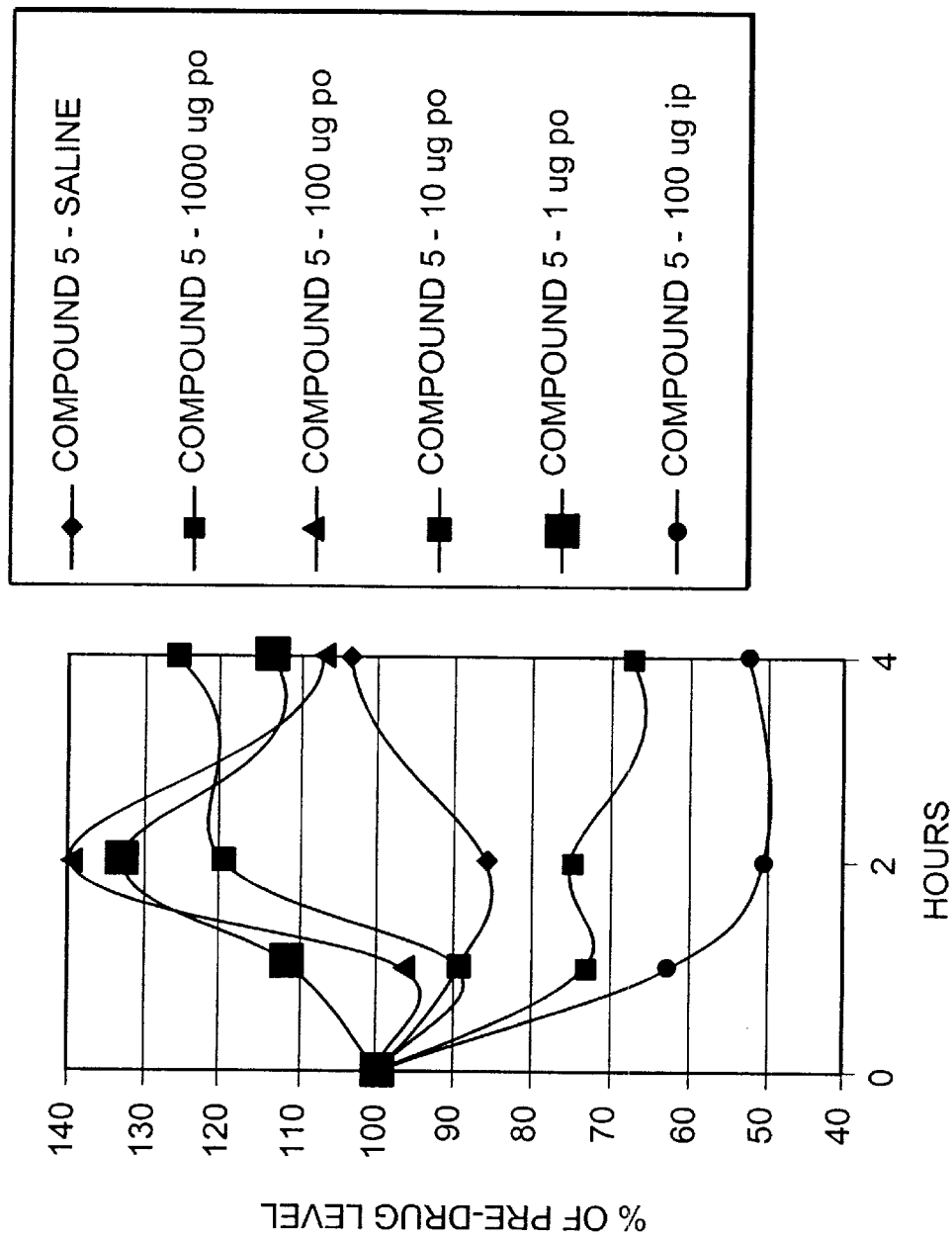
FIG. 3 shows the effect of Compound 5 (SEQ ID NO:89) (Gly$^8$, Lys$^{37}$ (palmitoyl)-GLP1-(7–36)(Human)-(Lys)$_7$-NH$_2$ on the blood glucose levels of mice, cf. Example 25.

The results obtained are shown in Table 4 and in FIGS. 1–3.

These results show that all tested compounds have an effect in lowering blood glucose levels. The effect is most pronounced when Compound 1 is given intraperitoneally whereas the effect of 1000 μg po of Compound 2 is comparable to the effect of 100 μg ip of Compound 2. The potency of Compound 1 (des $Pro^{36}$-exendin-4(1–39)-$NH_2$, SEQ ID NO:101) and Compound 2 (des $Pro^{36}$exendin-4 (1–39)-$Lys_6$-$NH_2$, SEQ ID NO:93) when given intraperitoneally is shown to be very similar to exendin-4(1–39)-$NH_2$ (Compound (i)) itself (data not given) administered in the same way.

For Compound 1. des $Pro^{36}$-exendin-4(1–39)-$NH_2$ (SEQ ID NO:101), there is no effect in lowering blood glucose levels up to a dose of 400 μg/mouse when the compound is administered perorally, whereas for the same compound with the addition of the Lys6 fragment there is activity seen at a dose of 10 μg/mouse. This indicates that the minimum effective oral dose of the des $Pro^{36}$-exendin-4(1–39)-$Lys_6$-NH2 (SEQ ID NO:93) is at least 40 times lower than for des $Pro^{36}$-exendin-4(1–39)-$NH_2$ (SEQ ID NO:101).

These results show that the attachment of the sequence Z has no significant effect on the potency of the various peptides when administered interperitoneally while significantly enhancing the potency of the compound when administered perorally.

26. Bioavailability of Compound 4 and Compound (iii) after gastro-intestinal delivery in duodenum in conscious rats.

Various peptide based GLP-1 analogues have been developed for parenteral use, but none of these substances has been pharmacologically effective after oral administration [Holst, J. J.: Enteroglucagon. *Annu Rev Physiol,* 59:257–271, 1997]. It was decided to examine the absorption of the test compound from the duodenum in conscious rats. Compound (iii) ($Gly^8$)hGLP-1(7–36)-$NH_2$ was used as reference.

Chemicals and Reagents

Blank rat plasma in sodium heparin (5000 units/mL) were obtained from Harlan Sera Lab Ltd. (Loughborough, UK). OASIS™ HLB solid phase extraction columns, 1 cc, 30 mg sorbet, were obtained from Waters (Milford, Mass., U.S.A.) and ISOLUTE C18 (EC), 1 cc, SPE columns were obtained from IST (Mid Glamorgan, U.K.). The LC/MS analysis was performed on a HP 1100 instrument consisting of an on-line degasser, a binary gradient pump, an auto sampler, a column oven, Hewlett Packard (Wilmington, Del., U.S.A.) in combination with a Quattro Ultima mass spectrometer from Micromass (Altrincham, UK) both the LC and MS were controlled by MassLynx 3.3 software. The LC separations prior to MS detection were performed on a Vydac 218MS52 (2.1×250 mm) column (Hesperia, Calif., U.S.A.).

Drugs and Dose Levels

Compound 4 (batch No. ZP 7.97-5-F, 4053 g/mol) and Compound (iii) (batch No. ZP 7.73-2-G, 3854 g/mol) were synthesised in-house using the Fmoc strategy. The identification was performed by mass spectrometry and the purity of both batches was determined by RP-HPLC to 97 and 99.7% for the test compounds, respectively. The peptide content of the batches were 72% and 80% for ZP 7.97-5-F and ZP 7.73-2-G, respectively. The peptides were dissolved in pyrogen free isotonic saline and doses of 1.000 or 10.000 nmol/kg administered through the intra duodenal catheter in a volume of 100 μl.

Animals

Fourteen Sprague-Dawley rats weighing 250 to 350 g. were used for the experiment. The rats were anaesthetised with Hypnorm®-Dormicum® s.c. and a catheter was inserted into the femoral artery for arterial blood sampling. An additional catheter was inserted into the duodenum via an incision in the ventricle. Before the experiment was started, the rats were allowed to recover for one week after the operation. The operated rats were conscious at the day of the experiment. In order to establish whether the intra duodenal catheters were situated in the duodenum, an autopsy was performed on the rats immediately after the experiment.

Sample Treatment

Blood samples were collected at t=–5, 5, 10, 15, 20, 40, and 60 min. The blood as collected in EDTA containing ice-chilled tubes and immediately centrifuged at 4 C for 5 min (4.000×g). Plasma (250 μl) was transferred to ice-chilled 0.75 ml PLC vials containing 250 μl extraction solution (MeCN: 0.18 M Ammonium Carbonate pH 9.5, 10:90 v/v). The plasma samples were stored at –20 C until SPE and LC/MS analysis.

Solid Phase Extraction

The drug containing plasma samples (400 μl) were loaded onto solid phase extraction columns preconditioned with 950 μl MeCN followed by 950 μl water. The columns were washed with 950 μl 2% TFA in water followed by an equal volume of 2% TFA in MeCN:water (20:78 v/v). The analytes were eluted with 500 μl 2% TFA in MeCN:water (60:38 v/v) and analysed by LC/MS.

LC/MS

The samples were kept at 18° C. in the auto sampler tray prior to injection of 20 to 50 μl onto the LC column (Vydac 218MS52 (2.1×250 mm). The separations were performed at 30° C. using a flow rate of 250 μl/min and a gradient according to Table 1. Both the test compound and the reference drug were detected by sine) ion recording (SIR) using the m/z=676.7 and the m/z=1095.2 and 821.8 ion species, respectively. All instrument conditions were controlled by MassLynx software ver. 3.3 software.

| Compound | Gradient |
| --- | --- |
| Compound 4 | Initial: 15% B, 0–14 min; 15–50% B, 14–15 min; 50–15% B and 15–20 min 15% B. |
| Compound (iii) | Initial: 25% B, 1–1.5 min; 25–30% B, 1.5–10 min; 30–40% B, 10–10.5 min; 40–90% B, 11.5–12 min; 90–25% B, and 12–17 min 25% B. |

The gradient used for the analysis of the test compounds using 0.1% formic acid in water or MeCN as Mobile phase A or B, respectively.

The plasma samples were analysed as described under materials and methods. The bioavailability of Compound 4 was examined in doses of 1.000 (n=4) and 10.000 (n=5) nmol/k, whereas Compound (iii) was only studied in a dose of 10.000 (n=5) nmol/kg. At all the investigated time points the concentration of Compound (iii) was below the detection limit (approx. 0.5 nM), the exact bioavailability could therefore not be estimated. In contrast, Compound 4 was detected in the plasma samples from two out of four rats after intra duodenal administration of 1.000 nmol/kg and in four out of five rats following administration of 10.000 nmol/kg.

27. In vivo pharmacokinetics of Compound 1, Compound 2, Compound 4, and Compound (iii) after i.v. administration to rabbits and pigs We have shown an increased in vitro stability of the GLP-1 agonist Compound 4 when compared to the reference drug Compound (iii) in rat plasma. In order to establish whether this effect is sustained in vivo, the pharmacokinetic parameters of the two compounds are examined in rabbits. Using the same experimental conditions these parameters were also measured for Compounds 1 and 2 in rabbits and using similar conditions in pigs.

Chemicals and Reagents

Blank rabbit plasma in sodium heparin (5000 units/mL) were obtained from Harlan Sera Lab Ltd. (Loughborough, UK). OASIS™ HLB solid phase extraction columns, 1 cc. 30 mg sorbent, were obtained from Waters (Milford, Mass., U.S.A.) and ISOLUTE C18 (EC), 1 cc, SPE columns were obtained from IST (Mid Glamorgan, U.K.). The LC/MS analysis was performed on a HP 1100 instrument consisting of an on-line degasser, a binary gradient pump, an auto sampler, a column oven, Hewlett Packard (Wilmington, Del., U.S.A.) in combination with a Quattro Ultimo mass spectrometer from Micromass (Altrincham, UK) both the LC and MS were controlled by MassLynx 3.3 software. The LC separations prior to MS detection were performed on a Vydac 218MS52 (2.1×250 mm) column (Hesperia, Calif., U.S.A.).

Drugs and Dose Levels

Compound 4 (batch No. ZP 7.97-5-F, 4053 g/mol) and Compound (iii) (batch No. ZP 7.73-2-G, 3854 g/mol) were synthesised in-house using the Fmoc strategy. The identification was performed by mass spectrometry and the purity of both batches were determined by RP-HPLC to 97 and 99.7% for the test compounds, respectively. The peptide content of the batches were 72% and 80% for ZP 7.97-5-F and ZP 7.73-2-G, respectively. The peptides were dissolved in pyrogen free isotonic saline and both peptides were administered i.v. to rabbits and rats using a dose of 1000 nmol/kg.

Rabbits

Fifteen New Zealand White rabbits weighing 2.5 to 3.0 kg were used for the experiment. On the day of the experiment, the rabbits were anaesthetised with Hypnorm® i.m. followed by Dormicum® i.v., Catheters were inserted into the femoral vein and artery for i.v. administration of drugs and arterial blood sampling. The rabbits stayed unconscious throughout the experiment.

Sample Treatment

Blood samples were collected at t–1, 3, 5, 10, 15, 20, 30, 40, 60, 90, 120, 150, 180, and 240 min. The blood was collected in EDTA containing ice-chilled tubes and immediately centrifuged at 4 C for 5 min (20.000×g). Plasma (250 µl) was transferred to ice-chilled 0.75 ml PLC vials containing 250 µl extraction solution (MeCN: 0.18 M Ammonium Carbonate pH 9.5, 10:90 v/v). The plasma samples were stored at −20 C until SPE and LC/MS analysis.

Solid Phase Extraction

The drug containing plasma samples (400 µl) are loaded onto OASIS™ HLB (Compound 4) or ISOLUTE™ (Compound (iii)) solid phase extraction columns preconditioned with 950 µl MeCN followed by 950 µl water. The columns are washed with 950 µl 2% TFA in water followed by an equal volume of 2% TFA in MeCN:water (20:78 v/v). The analytes are eluted with 500 µl 2% TFA in MeCN:water (60:38 v/v) and analysed by LC/MS.

LC/MS

The samples were kept at 18 C in the auto sampler tray prior to injection of 20 to 50 µl onto the LC column (Vydac 218MS52 (2.1×250 mm). The separations were performed at 30° C. using a flow rate of 250 µl/min and a gradient according to the table below. Both the test compound and the reference drug are detected by single ion recording (SIR) using the m/z=676.7 and the m/z=1095.2 and 821.8 ion species, respectively. All instrument conditions were controlled by MassLynx software ver. 3.3 software.

| Compound | Gradient |
| --- | --- |
| Compound 4 | Initial: 15% B, 0–14 min; 15–50% B, 14–15 min; 50–15% B and 15–20 min 15% B. |
| Compound (iii) | Initial: 25% B, 1–1.5 min; 25–30% B, 1.5–10 min; 30–40% B, 10–10.5 min; 40–90% B, 11.5–12 min; 90–25% B, and 12–17 min 25% B. |

The gradient used for the analysis of the test compounds using 0.1% formic acid in water or MeCN as Mobile phase A or B, respectively.

Figure 4:
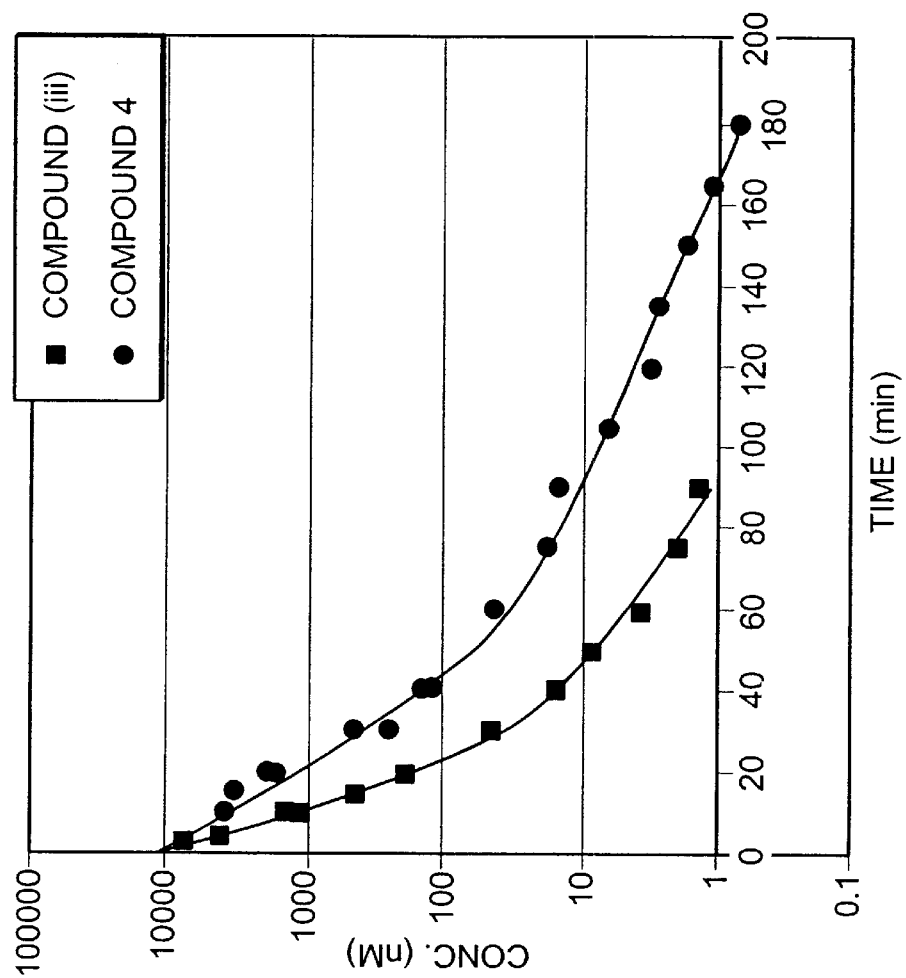
FIG. 4 shows in vivo degradation kinetics in rabbits after i.v. injection of 1 μm/kg of Compound 4 and Compound (iii), cf. Example 27.

The plasma samples were analysed as described under materials and methods and the plasma concentration ($C_{pl}$) plotted versus time in a semi log diagram. The plasma concentration were followed for three hours in rabbits, whereas the limited blood volume of rats restricted the blood sampling in this specie to one hour. The $C_{pl}$ vs. time curves from the individual rabbits were fitted to a two-compartment open model (figure not shown) using $1/y^2$ weighted least squares in WinNonlin 3.1 (Pharsight Corp. (Mountain View, Calif.)). The pharmacokinetic constants obtained from the data analysis are listed in Table 5 and the degradation kinetics in rabbit after i.v. injection of 1 µmol/kg of Compound 4 and Compound (iii), respectively, is shown in FIG. 4.

TABLE 5

In vivo kinetics in rabbits and pigs**

| Parameter | Comp. (iii) (n = 7) Mean | Comp. 4 (n = 8) Mean | Comp. 1 (n = 5) Mean | Comp. 2 (n = 5) Mean | Comp. 2** (n = 2) Mean |
|---|---|---|---|---|---|
| $T_{1/2}$, α min | 2.3 | 6.8 | 4.4 | 11 | 16 |
| $T_{1/2}$, β min | 10.8 | 28.0 | 23 | 69 | 252 |

Table 5: The pharmacokinetic constants were obtained from rabbits when the $C_{pl}$ vs. time curves was fitted mathematically. The compounds were administered iv in a concentration of 1000 nmol/kg. $T_{1/2}$ values are given in minutes (min) for the a and P phase. Statistics: two-tailed t-test assuming samples with unequal variances showed p<0.001 for all measured parameters. In conclusion the T½ value for Compound 4 is approximately three times the value for the reference Compound (iii) and, likewise, the T½ value for Compound 2 is approximately three times the value calculated for Compound 1 which represents the unconjugated equivalent.

28. Glucose tolerance test of Compounds 2, 14–16, 18 and 19 compared to Compound (i)

Male diabetic db/db mice (M & B, Bomholdtgaard, Ll. Skensved, Denmark) are used. This well-described mouse model has inherited malfunctions of the glucose metabolism due to a mutation in the lepton receptor. Like human patients with uncontrolled non-insulin demanding diabetes mellitus (NIDDM), homozygous db/db mice experience polydipsia, polyuria and glycosuria and gain weight during their first 3 months of life despite their hyperglycaemic stage. However, in this model the hyperglycaemia is associated with progressive pancreatic islet atrophy with possible ketosis and death at 6–8 months of age. Thus, attention should be paid to the progression and status of their disease state. Therefore, preferably only db/db mice less than 16 weeks old should be used for drug testing og GLP-1 analogues. All animals are acclimatised for at least one week and handled day for two days prior to the first oral glucose tolerance test (OGTT). Furthermore, to reduce stress-induced glucose excursions, the animals should be subjected to at least one OGTT without compound as described below prior to the experiment. Due to the great scatter of glucose tolerance among diabetic mice, the animals are stratified by an OGTT prior to their first use.

Peptides

Peptides are dissolved in 0.1 M phosphate-buffered saline (PBS) with 0.1% bovine albumin where pH is adjusted to 7.4 by adding 5 M NaOH. All solutions are prepared fresh on the morning immediately before the experiment. Vehicle treated animals are given PBS with 0.1% albumin alone.

Glucose Tolerance Test and Dosing

Before the oral glucose tolerance test, the animals are fasted for 17 hours (from 4 p.m. until 9 a.m. the following morning). Beginning at 9.00 a.m. blood is taken from the tail tip (t=−15 min) and blood glucose is measured. The whole blood glucose (mM) concentration is analysed by the immobilised glucose oxidase method using a drop of blood (<5 μl, Elite Autoanalyser, Bayer, Denmark) following the manufacturer's manual. Animals with severe diabetes (>10 mM) are excluded. Immediately after the initial blood sample, the animals receive an intraperitoneal (i.p.) injection of vehicle or a dose of antidiabetic compound. Injection volume is 200 μl/50 g body weight in all groups. Fifteen minutes after i.p. administration of the substance an oral dose of 1 g/kg glucose (Sigma, St. Louis) dissolved in water (200 μl/50 g body weight) is given, and the animals are returned to their home cages (t=0). Blood glucose levels are measured at t=30 min, t=60 min, t=120 min and t=240 min. The animals are fasted during the observation period. For each animal a data log sheet was filled in at the time of each blood sampling.

Calculations and Statistics

In order to analyse the effects of the compounds, the absolute and the relative difference from baseline (t=0) are calculated for each time point. The area under the curve for the whole experiment (AUC 0–240 min) is determined using the trapezoid method. On the day of stratification, the mice are distributed in order to ensure that the glucose tolerances are similar in all groups. However, to correct for the progression of the diabetes with time, a vehicle treated control group is tested on each day of experiment and the response to drugs are expressed relative to response observed in vehicle-treated time-control animals.

Figure 5:
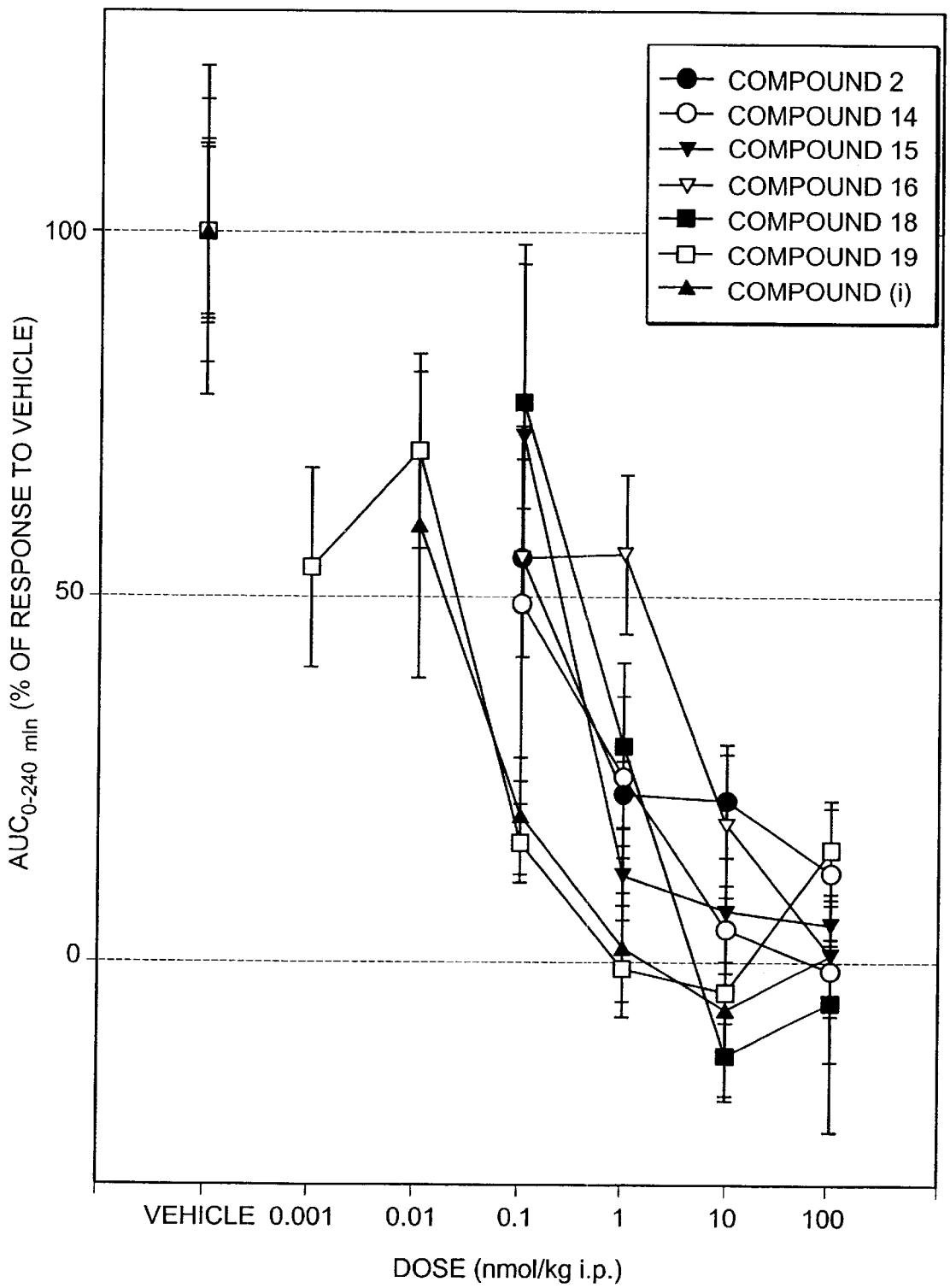
FIG. 5 is a plot of AUC (area under the curve) values (mean±SEM) for Compounds, 2,14–16, 18 and 19 in an oral glucose tolerance test (OGTT), cf. Example 28.

Dose-response curves for each substance are plotted, cf. FIG. 5, and the effect of drug relative to responses obtained during treatment with vehicle are analysed using an ANCOVA analysis (analysis of covariance). Treatment (drug or vehicle) is considered the independent variable, AUC 0–240 min expressed as percent response in vehicle-treated time-control mice is the dependent variable, and drug dose is defined as covariate. Post-hoc analysis is performed using Fisher's Least Significant test. Differences are considered significant at the 0.05 level. Statistical analyses were performed using Statistica version 5.5 for Windows NT, StatSoft, Tulsa, Okla., U.S.A. The dose response curves shown in FIG. 5 clearly shows that all tested compounds exhibit a glucose lowering effect comparable to that of the reference drug.

29. Effects of Compound 2 and Compound (i) on OGGT in db/db mice

Figure 7:
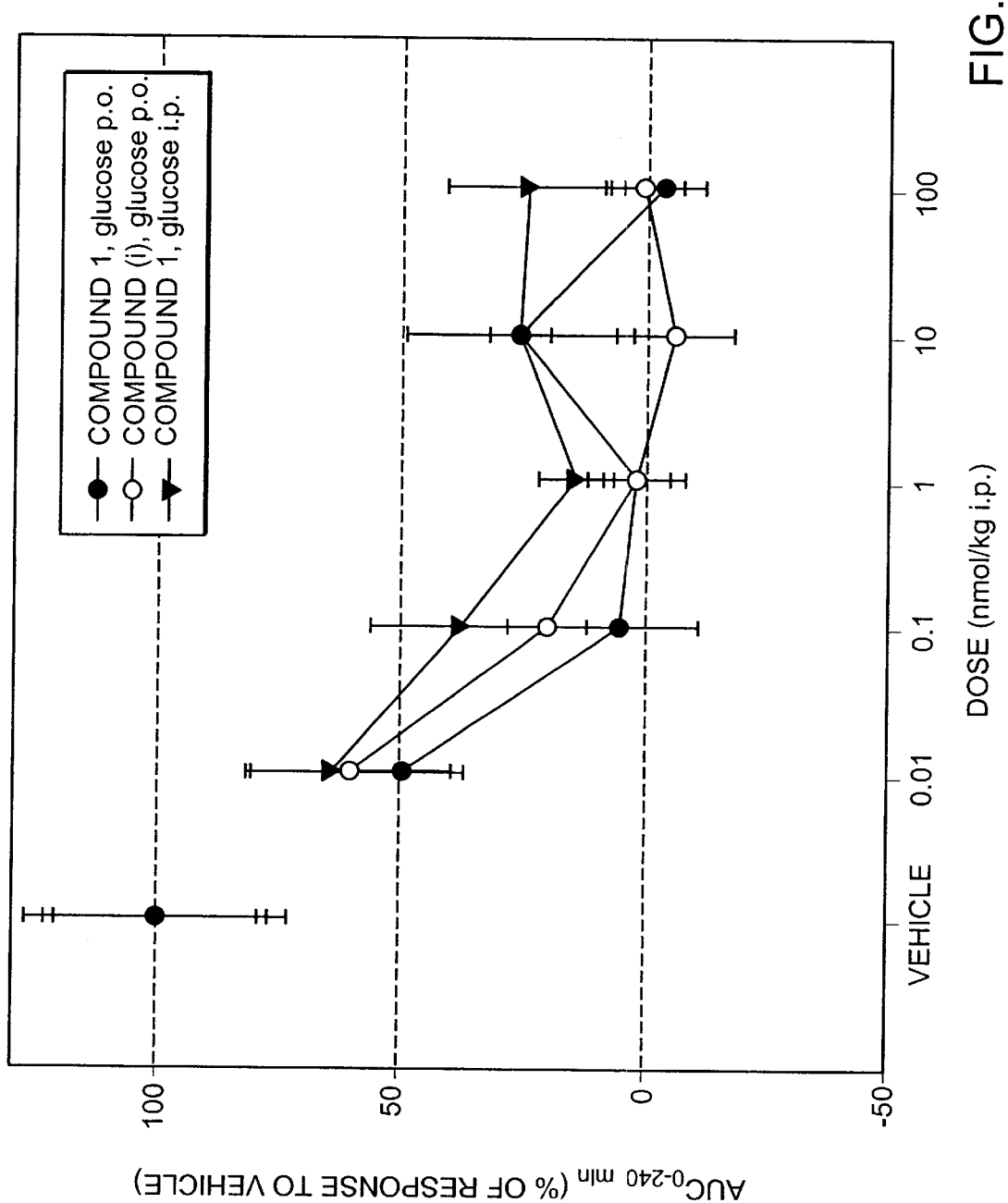
FIG. 7 is a plot of dose-response on GTT in db/db mice based on relative AUC$_{0-240\ min}$ values (mean±SEM) for Compound 2 and Compound (i), cf. Example 29.

FIG. 7 is a plot of AUC for Compound 2 and Compound (i) in an OGTT performed using the same experimental conditions as described in Example 28. The figure shows that the blood glucose lowering effect of Compound 2 is the same as the effect of the prior art compound (iii).

Figure 8:
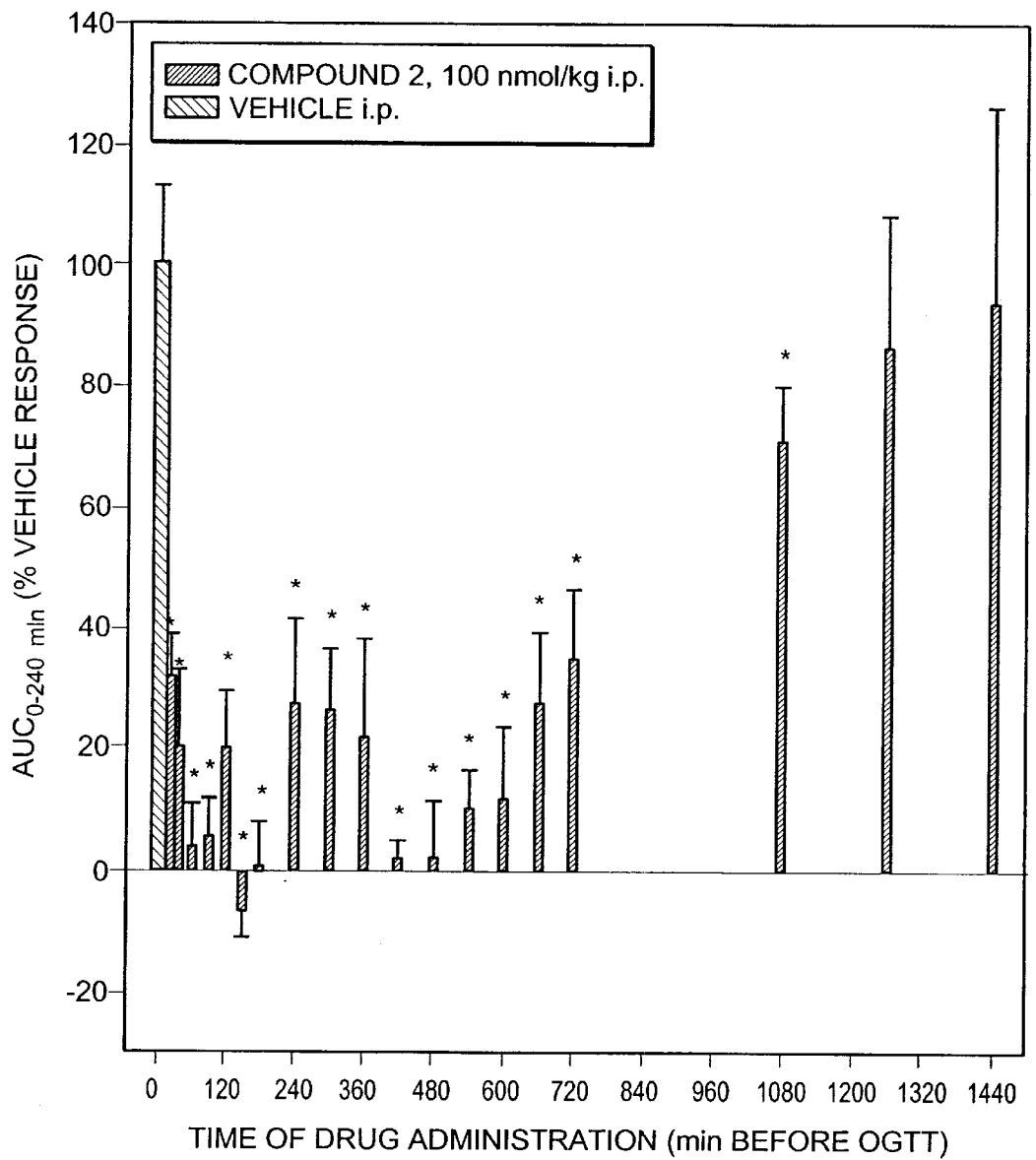
FIG. 8 shows the effects of a maximal dose of Compound 2, i.e. 100 nmol/kg i.p., on the oral glucose tolerance test (OGTT) when administered up to 24 hours before the OGTT.

30. Long term effects of Compound 2, 100 nmol/kg i.p. on the oral glucose tolerance test. (OGTT) when administered up to 24 hours before the OGTT This experiment uses the maximal dose of 100 nmol/kg i.p. in db/db mice and otherwise, the same experimental conditions as described in Example 28 are used. Results are shown in FIG. 8 and the conclusion of the experiment is that the duration of action of Compound 2 is up to 18 hours in db/db mice.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. Various references are cited herein, the disclosure of which are incorporated by reference in their entireties.

What is claimed is:

1. A peptide consisting of any one of the following sequences:

a) H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-(Lys)$_6$-NH$_2$ (des-Pro$^{36}$-exendin-4(1–39)-Lys$_6$-NH$_2$) (SEQ ID NO:93), b) H-Lys$_6$-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-(Lys)$_6$-NH$_2$ (H-Lys$_6$-des Pro$^{36}$exendin-4(1–39)-Lys$_6$-NH$_2$) (SEQ ID NO: 149), c) H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Trp-Leu-Lys-Asn-Gly-Gly-Pro-Ser-Ser-Gly-Ala-Ser-NH$_2$ (H-des Pro$^{36}$,Pro$^{37}$,Pro$^{38}$exendin-4(1–39)-NH$_2$) (SEQ ID NO: 132), d) H-Lys-Lys-Lys-Lys-Lys-Lys-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser-NH$_2$ (H-(Lys)$_6$-des Pro$^{36}$,Pro$^{37}$,Pro$^{38}$exendin-4(1–39)-NH$_2$), (SEQ ID NO: 134), e) H-Asn-Glu-Glu-Glu-Glu-Glu-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser-NH$_2$ (H-Asn-(Glu)$_5$-des Pro$^{36}$,Pro$^{37}$, Pro$^{38}$exendin-4(1–39)-NH$^2$) (SEQ ID NO: 137), f) H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser-(Lys)$_6$-NH$_2$ (des Pro$^{36}$, Pro$^{37}$,Pro$^{38}$exendin-4(1–39)-(Lys)$_6$-NH$_2$) (SEQ ID NO: 133), g) H-(Lys)$_6$-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser-(Lys)$_6$-NH$_2$ (H-(Lys)$_6$-des Pro$^{36}$,Pro$^{37}$, Pro$^{38}$exendin-4(1–39)-(Lys)$_6$-NH$_2$) (SEQ ID NO: 135), h) H-Asp-Glu-Glu-Glu-Glu-Glu-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser-(Lys)$_6$-NH$_2$ (H-Asn-(Glu)$_5$-des Pro$^{36}$,Pro$^{37}$,Pro$^{38}$exendin-4(1–39)-(Lys)$_6$-NH$_2$) (SEQ ID NO: 136);

or a pharmaceutically acceptable salt thereof.

2. A composition comprising the peptide of claim 1 and a physiologically acceptable carrier.

\* \* \* \* \*

UNITED STATES PATENT AND TRADEMARK OFFICE
CERTIFICATE OF CORRECTION

PATENT NO. : 6,528,486 B1  Page 1 of 1
APPLICATION NO. : 09/614847
DATED : March 4, 2003
INVENTOR(S) : Larsen et al.

It is certified that error appears in the above-identified patent and that said Letters Patent is hereby corrected as shown below:

Claim 1, part c, replace "H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Trp-Leu-Lys-Asn-Gly-Gly-Pro-Ser-Ser-Gly-Ala-Ser-$NH_2$ (H-des $Pro^{36}$, $Pro^{37}$, $Pro^{38}$exendin-4(1-39)-$NH_2$) (SEQ ID NO: 132),"

with --H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser-$NH_2$ (H-des $Pro^{36}$, $Pro^{37}$, $Pro^{38}$exendin-4(1-39)-$NH_2$) (SEQ ID NO: 132),--

Signed and Sealed this
Seventeenth Day of May, 2011

David J. Kappos
*Director of the United States Patent and Trademark Office*

UNITED STATES PATENT AND TRADEMARK OFFICE
CERTIFICATE OF CORRECTION

PATENT NO.      : 6,528,486 B1                           Page 1 of 1
APPLICATION NO. : 09/614847
DATED           : March 4, 2003
INVENTOR(S)     : Larsen et al.

It is certified that error appears in the above-identified patent and that said Letters Patent is hereby corrected as shown below:

Column 117, lines 24-28 (Claim 1, part c) replace "H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Trp-Leu-Lys-Asn-Gly-Gly-Pro-Ser-Ser-Gly-Ala-Ser-$NH_2$ (H-des $Pro^{36}$, $Pro^{37}$, $Pro^{38}$exendin-4(1-39)-$NH_2$) (SEQ ID NO: 132),"

with --H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser-$NH_2$ (H-des $Pro^{36}$, $Pro^{37}$, $Pro^{38}$exendin-4(1-39)-$NH_2$) (SEQ ID NO: 132),--

This certificate supersedes the Certificate of Correction issued May 17, 2011.

Signed and Sealed this
Twenty-first Day of June, 2011

David J. Kappos
*Director of the United States Patent and Trademark Office*